(12) United States Patent
Sadamasa et al.

(10) Patent No.: US 9,289,236 B2
(45) Date of Patent: Mar. 22, 2016

(54) MUCOSA SEPARATION APPARATUS, AND METHOD FOR MUCOSA SEPARATION

(75) Inventors: Akihito Sadamasa, Hirosaki (JP); Yasuo Miyano, Tokyo (JP); Yutaka Yanuma, Tokyo (JP); Ichiro Takahashi, Tokyo (JP); Kenji Shibaki, Tokyo (JP); Tsutomu Nakamura, Tokyo (JP); Tsuyoshi Nakagawa, Tokyo (JP); Yasuhito Kura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1431 days.

(21) Appl. No.: 11/944,821

(22) Filed: Nov. 26, 2007

(65) Prior Publication Data

US 2008/0125803 A1 May 29, 2008

Related U.S. Application Data

(63) Continuation of application No. PCT/JP2006/310904, filed on May 31, 2006.

(30) Foreign Application Priority Data

| May 31, 2005 | (JP) | 2005-159400 |
| May 31, 2005 | (JP) | 2005-159401 |
| May 31, 2005 | (JP) | 2005-160296 |
| Jun. 1, 2005 | (JP) | 2005-161232 |
| Jun. 7, 2005 | (JP) | 2005-166922 |

(51) Int. Cl.
*A61B 17/00* (2006.01)
*A61B 17/34* (2006.01)
(Continued)

(52) U.S. Cl.
CPC ............ *A61B 17/3478* (2013.01); *A61B 10/06* (2013.01); *A61B 1/018* (2013.01);
(Continued)

(58) Field of Classification Search
CPC ............ A61M 25/10; A61M 25/0133; A61M 25/0144; A61M 25/0147; A61M 2025/015; A61M 25/0155; A61B 19/24; A61B 2017/00296; A61B 2017/003; A61B 2017/00318; A61B 2017/00323; A61B 2017/00327; A61B 2017/00331; A61B 2017/22061; A61B 2017/22071
USPC ................... 606/190–192, 194; 604/523, 528
See application file for complete search history.

(56) References Cited

U.S. PATENT DOCUMENTS 5,454,788 A * 10/1995 Walker et al. ............... 604/99.04
5,531,686 A * 7/1996 Lundquist et al. ......... 604/95.04
(Continued)

FOREIGN PATENT DOCUMENTS

| CN | 2689888 Y | 4/2005 |
| EP | 1 570 778 | 9/2005 |

(Continued)

OTHER PUBLICATIONS

Office Action issued by the Chinese Patent Office on Feb. 20, 2009 in connection with corresponding Chinese Patent Application No. 200680018735.0.

(Continued)

*Primary Examiner* — Katherine Rodjom
(74) *Attorney, Agent, or Firm* — Ostrolenk Faber LLP

(57) ABSTRACT

This mucosa separation apparatus includes a first insertion portion inserted to the interior of a subject, an expansion portion disposed on a head portion of the first insertion portion, and which expands by infusion of a fluid, a passage formed within the first insertion portion and connected to the expansion portion, for supplying the fluid to the expansion portion, and a curving portion which makes a head portion of an instrument inserted to the interior of the subject curve with respect to a part of the instrument which is closer to a base portion of the instrument than the head portion thereof.

3 Claims, 79 Drawing Sheets

(51) Int. Cl.
*A61B 10/06* (2006.01)
*A61B 1/018* (2006.01)
*A61B 1/273* (2006.01)
*A61B 18/14* (2006.01)
*A61B 19/00* (2006.01)
*A61B 17/22* (2006.01)
*A61B 17/32* (2006.01)

(52) U.S. Cl.
CPC .......... *A61B 1/273* (2013.01); *A61B 18/1492* (2013.01); *A61B 19/24* (2013.01); *A61B 2017/003* (2013.01); *A61B 2017/00269* (2013.01); *A61B 2017/00296* (2013.01); *A61B 2017/22051* (2013.01); *A61B 2017/320048* (2013.01); *A61B 2019/462* (2013.01)

(56) References Cited

U.S. PATENT DOCUMENTS

| | | | | |
|---|---|---|---|---|
| 5,814,016 | A | * | 9/1998 | Valley et al. ............... 604/96.01 |
| 6,231,518 | B1 | | 5/2001 | Grabek et al. |
| 2001/0049497 | A1 | | 12/2001 | Kalloo et al. ............ 604/164.01 |
| 2003/0135091 | A1 | | 7/2003 | Nakazawa et al. |
| 2004/0133075 | A1 | | 7/2004 | Motoki et al. ................ 600/131 |
| 2005/0165437 | A1 | | 7/2005 | Takimoto ..................... 606/190 |
| 2005/0222517 | A1 | * | 10/2005 | Tiesma et al. ................ 600/549 |

FOREIGN PATENT DOCUMENTS

| | | |
|---|---|---|
| JP | S61-179141 | 8/1986 |
| JP | 3036470 | 2/1997 |
| JP | UM-B-3036470 | 4/1997 |
| JP | 10-328306 | 12/1998 |
| JP | 11-505141 | 5/1999 |
| JP | 11-151292 | 6/1999 |
| JP | 11-508790 | 8/1999 |
| JP | 2001-212078 | 8/2001 |
| JP | 2001-292959 | 10/2001 |
| JP | 2003-299663 | 10/2003 |
| JP | 2003-305001 | 10/2003 |
| JP | 2003-310545 | 11/2003 |
| JP | 200486208 | 3/2004 |
| JP | 2005-7161 | 1/2005 |
| JP | 2005-177135 | 7/2005 |
| WO | WO 96/35470 | 11/1996 |
| WO | WO 97/01988 | 1/1997 |
| WO | WO 02/089655 | 11/2002 |
| WO | WO 03/101519 | 12/2003 |

OTHER PUBLICATIONS

Translation of the Office Action issued by the Chinese Patent Office on Feb. 20, 2009 in connection with corresponding Chinese Patent Application No. 200680018735.0.
Ono, Hiroyuki et al. "Knack for EMR Using an IT knife Over Early Stage Cancer", Alimentary Tract Endoscope, Alimentary Tract Endoscope Editing Committee, Tokyo Igaku-sya Co., Ltd., Nov. 2002, vol. 14, No. 11, pp. 1737-1740 (w/ English Translation).
PCT International Search Report and Written Opinion dated Aug. 8, 2006 issued in PCT International Appln. No. PCT/JP2006/310904 filed May 31, 2006.
Office Action issued by the Japanese Patent Office on Feb. 8, 2011 in connection with corresponding Japanese Patent Application No. 2005-166922.
Translation of the Office Action issued by the Japanese Patent Office on Feb. 8, 2011 in connection with corresponding Japanese Patent Application No. 2005-166922.
Office Action issued by the Japanese Patent Office on Feb. 8, 2011 in connection with corresponding Japanese Patent Application No. 2005-161232.
Translation of the Office Action issued by the Japanese Patent Office on Feb. 8, 2011 in connection with corresponding Japanese Patent Application No. 2005-161232.
Office Action issued by the Japanese Patent Office on Dec. 20, 2010 in commection with corresponding Japanese Patent Application No. 2005-160296.
Translation of the Office Action issued by the Japanese Patent Office on Dec. 20, 2010 in connection with corresponding Japanese Patent Application No. 2005-160296.
Office Action issued by the Japanese Patent Office on Jan. 11, 2011 in connection with corresponding Japanese Patent Application No. 2005-159400.
Translation of the Office Action issued by the Japanese Patent Office on Jan. 11, 2011 in connection with corresponding Japanese Patent Application No. 2005-159400.
Office Action issued by the Japanese Patent Office on Jan. 25, 2011 in connection with corresponding Japanese Patent Application No. 2005-159401.
Translation of the Office Action issued by the Japanese Patent Office on Jan. 25, 2011 in connection with corresponding Japanese Patent Application No. 2005-159401.
Translation of the Office Action issued by the Japanese Patent Office on Aug. 8, 2011 in connection with corresponding Japanese Patent Application No. 2005-166922.
Search Report issued by European Patent Office on Feb. 19, 2014 in connection with corresponding European application No. EP 06 756 824.6.

* cited by examiner 172 176 174   170   170   129   127   142   125

| OUTER DIAMETER OF HEAD PORTION OF CATHETER | FLEXIBLE LIMIT TARGET VALUE (INSERTION AVAILABLE FORCE) | SOLID LIMIT TARGET VALUE (PIERCING FORCE) |
|---|---|---|
| 0.8mm | 1.7N | 2.5N |
| 0.9mm | 1.9N | 2.8N |
| 1.0mm | 2.1N | 3.1N |
| 1.1mm | 2.4N | 3.5N |
| 1.2mm | 2.6N | 3.8N |
| 1.3mm | 2.8N | 4.1N |

MUCOSA SEPARATION APPARATUS, AND METHOD FOR MUCOSA SEPARATION

PRIORITY CLAIM

This application is continuation application of a PCT Application No. PCT/JP2006/310904, filed on May 31, 2006, entitled "MUCOSA SEPARATION APPARATUS, AND METHOD FOR MUCOSA SEPARATION" whose priority is claimed on Japanese Patent Application No. 2005-159400 filed May 31, 2005, Japanese Patent Application No. 2005-159401 filed May 31, 2005, Japanese Patent Application No. 2005-160296 filed May 31, 2005, Japanese Patent Application No. 2005-161232 filed Jun. 1, 2005, and Japanese Patent Application No. 2005-166922 filed Jun. 7, 2005, the content of which is incorporated herein by reference.

BACKGROUND OF THE INVENTION

1. Field of the Invention

The present invention relates to a mucosa separation apparatus for removing a diseased part of an alimentary tract using an endoscope, and a method for mucosa separation using the apparatus.

2. Description of Related Art

Endoscopic Mucosal Resection (EMR), which means resection of a disease using an endoscope, is as common treatment procedure over a diseased part of the alimentary tract. As the "method for incision and separation", a method in which a well-conditioned mucosa positioned around the diseased part is incised using a high-frequency cutting instrument such as a high-frequency knife, and thereafter a submucosal layer is removed by separating the submucosal layer from a body is disclosed (for example, refer to "Knack for EMR Using an IT knife Over Early Stage Cancer", Hiroyuki Ono, and three others, Alimentary Tract Endoscope, Alimentary Tract Endoscope Editing Committee, Tokyo Igaku-sya Co., Ltd., November, 2002, Volume 14, Number 11, pages 1737-1740).

Further, it is suggested that the high-frequency knife is used for different procedures (refer to U.S. Patent Publication No. 2001/0049497A1).

SUMMARY OF THE INVENTION

The mucosa separation apparatus according to an aspect of the present invention includes: a first insertion portion inserted into the interior of a subject; an expansion portion disposed on a head portion of the first insertion portion, and which expands by infusion of a fluid; a passage formed within the first insertion portion and connected to the expansion portion, for supplying the fluid to the expansion portion; and a curving portion which makes a head portion of an instrument inserted to the interior of the subject curve with respect to a part of the instrument which is closer to a base portion of the instrument than the head portion thereof.

In the mucosa separation apparatus of the present invention, the curving portion may include: a wire inserted into the interior of the first insertion portion, one end of which is connected to the head portion of the first insertion portion; and an operation section disposed on a base portion of the first insertion portion, and connected with the other end of the wire. The head portion of the first insertion portion may be curved by moving the operation section.

In the mucosa separation apparatus of the present invention, a first flexible portion which is more flexible than a part of the first insertion portion which is closer to a base portion of the first insertion portion than the head portion thereof, may be disposed on the head portion of the first insertion portion. When a force having a predetermined strength acts on the first flexible portion, the first flexible portion may be curved before the part of the first insertion portion which is close to the base portion thereof.

In the mucosa separation apparatus of the present invention, a first curving support member having a characteristic of being more flexible only in a particular direction, and which supports the curving motion of the head portion of the first insertion portion, may be disposed on the head portion. The first curving support member may be arranged so as to bring the particular direction in line with the direction in which the head portion of the first insertion portion is allowed to curve.

In the mucosa separation apparatus of the present invention, the operation section may be rotatable, and may include a rotation transmission section which transmits the rotation force generated by rotating the operation section to the wire. At least the head portion of the first insertion portion may rotate around an axis of the head portion thereof.

In the mucosa separation apparatus of the present invention, a channel into which a high-frequency cutting instrument is inserted may be formed within the first insertion portion in the area of one end of the first insertion portion through the other end thereof.

In the mucosa separation apparatus of the present invention, indicators which indicate insertion quantity of the head portion of the first insertion portion into the mucosa, may be disposed on a part of the first insertion portion which is closer to the base portion than the expansion portion.

The mucosa separation apparatus of the present invention may further include a second insertion portion inserted into the interior of the subject, which supports the insertion of the first insertion portion into the mucosa. The curving portion may be disposed on a head portion of the second insertion portion.

In the mucosa separation apparatus of the present invention, the curving portion may include: a wire which is inserted into the interior of the second insertion portion, one end of which is connected to the head portion of the second insertion portion; and an operation section which is disposed on the base portion of the second insertion portion, and which is connected with the other end of the wire. The head portion of the second insertion portion may be curved by moving the operation section.

In the mucosa separation apparatus of the present invention, a second flexible portion which is more flexible than a part of the second insertion portion which is closer to a base portion of the second insertion portion than the head portion thereof, may be disposed on the head portion of the second insertion portion. When a force having a predetermined strength acts on the second flexible portion, the second flexible portion may be curved before the part of the second insertion portion which is close to the base portion thereof.

In the mucosa separation apparatus of the present invention, a second curving support member having a characteristic of being more flexible only in a particular direction, and which supports the curving motion of the head portion of the second insertion portion, may be disposed on the head portion. The second curving support member may be arranged so as to bring the particular direction in line with the direction in which the head portion of the second insertion portion is allowed to curve.

In the mucosa separation apparatus of the present invention, a spherical shape portion may be disposed on a tip of the second insertion portion.

In the mucosa separation apparatus of the present invention, indicators which indicate insertion quantity of the head portion of the second insertion portion into the mucosa, may be disposed on the part of the second insertion portion which is closer to the base portion of the second insertion portion than the head portion thereof.

In the mucosa separation apparatus of the present invention, a third flexible portion which deforms when a force having a value between a flexible limit and a solid limit acts on the third flexible portion, may be disposed on the head portion of the first insertion portion.

In the mucosa separation apparatus of the present invention, a third flexible portion may be disposed on the top end of the head portion of the first insertion portion.

In the mucosa separation apparatus of the present invention, the curving rigidity of the third flexible portion may be uniformly distributed along the longitudinal direction of the first insertion portion so that the third flexible portion is curved so as to form an uniform arc when the third flexible portion deforms.

In the mucosa separation apparatus of the present invention, the third flexible portion may have a characteristic of being more flexible in a particular direction.

The mucosa separation apparatus of the present invention may include an insertion support instrument which supports the insertion of the first insertion into the subject. The curving portion may be disposed on a tip of the insertion support instrument.

In the mucosa separation apparatus of the present invention, when the curving portion is pushed onto a wall surface of a hollow organ of the subject, the curving portion may deform in response to the reaction force from the wall surface, and may allow changing of the insertion angle of the first insertion portion into a hollow organ.

In the mucosa separation apparatus of the present invention, a fourth flexible portion which deforms in response to the reaction force from the wall surface of a hollow organ of the subject, and which allows changing of the insertion angle of the first insertion portion into the hollow organ when the curving portion is pushed onto the wall surface, may be disposed on the curving portion.

In the mucosa separation apparatus of the present invention, a guide portion which guides the first insertion portion in a predetermined direction with respect to the fourth flexible portion may be disposed on the fourth flexible portion.

In the mucosa separation apparatus of the present invention, the insertion support instrument may be used along an insertion portion of an endoscope. Further, the insertion support instrument may include an external channel separately from a channel of the endoscope, and a connection portion for connecting the insertion support instrument with the insertion portion of the endoscope may be disposed on the curving portion.

In the mucosa separation apparatus of the present invention, the insertion support instrument may include a support portion for supporting the curving portion with respect to the insertion portion. The external diameter of the curving portion and the external diameter of the support portion may be such that each of the curving portion and the support portion is insertable into a channel of an endoscope.

The method for mucosa separation according to an aspect of the present invention includes the steps of: forming an aperture in mucosa in the vicinity of an affected portion of a hollow organ; piercing the submucosal layer of the hollow organ through the aperture so as to form an insertion hole substantially parallel to the muscularis propria under the submucosal layer; and separating the submucosal layer from the muscularis propria by expanding the inside of the insertion hole.

In the method for mucosa separation of the present invention, the step of piercing may include the steps of: inserting an instrument into the submucosal layer through the aperture; curving a head portion of the instrument; and pushing the instrument into the submucosal layer.

In the step of separating of the method for mucosa separation of the present invention, the insertion hole may be expanded by expanding an expansion portion provided to the instrument within the submucosal layer.

In the step of separating of the method for mucosa separation of the present invention, another instrument may be inserted into the insertion hole instead of the instrument, and the insertion hole may be expanded by expanding an expansion portion provided to the another instrument within the submucosal layer.

In the step of curving of the method for mucosa separation of the present invention, the head portion of the instrument my be actively-curved.

In the method for mucosa separation of the present invention, the head portion of the instrument may be curved using a curving mechanism provided with the instrument.

In the step of curving of the method for mucosa separation of the present invention, the head portion of the instrument may be passively-curved.

In the method for mucosa separation of the present invention, the head portion of the instrument having flexibility may be curved by pushing such head portion onto a wall surface in the vicinity of the affected portion of the hollow organ.

In the method for mucosa separation of the present invention, the insertion support instrument is deformed by pushing the insertion support instrument onto a wall surface in the vicinity of the affected portion of the hollow organ, and the head portion of the instrument may be curved by moving such head portion along the deformed insertion support instrument.

In the method for mucosa separation of the present invention, the head portion of the instrument may be curved using a curving mechanism provided with an insertion portion of an endoscope.

The method for mucosa separation of the present invention may include the step of inflating the mucosa and the submucosal layer before the step of aperture-forming.

In the method for mucosa separation of the present invention, the mucosa and the submucosal layer of the affected portion may be treated while grasping the mucosa and the submucosal layer using grasping forceps.

BRIEF DESCRIPTION OF THE DRAWINGS

FIG. 75 is a chart for explaining a flexible limit and a solid limit which are necessary to set the rigidity of the head portion of the separation balloon insertion device of the fifth embodiment.

FIG. 120 is a view showing a method for mucosa separation of the twelfth embodiment of the present invention, and shows a state where the balloon insertion portion pierces the submucosal layer again after incising the mucosa around the aperture.

FIG. 121 is a view showing a method for mucosa separation of the twelfth embodiment of the present invention, and shows a state where the balloon is expanded within the submucosal layer again after re-piercing the submucosal layer by the balloon insertion portion.

FIG. 122 is a plan view showing the top end surface of the insertion portion of the endoscope of the thirteenth embodiment.

FIG. 123 is a view showing a method for mucosa separation of the thirteenth embodiment of the present invention, and shows a state where the mucosa and the submucosal layer located in the vicinity of the diseased part are grasped using the grasping forceps.

FIG. 124 is a view showing a method for mucosa separation of the thirteenth embodiment of the present invention, and shows a state where the mucosa and the submucosal layer located in the vicinity of the diseased part are grasped using the grasping forceps.

FIG. 125 is a view showing a method for mucosa separation of the thirteenth embodiment of the present invention, and shows a state where the tip of the balloon insertion portion is inserted into the aperture, while the mucosa and the submucosal layer located in the vicinity of the diseased part are grasped by the grasping forceps.

FIG. 126 is a view showing a method for mucosa separation of the thirteenth embodiment of the present invention, and shows a state where the balloon insertion portion pierces the submucosal layer, while the mucosa and the submucosal layer located in the vicinity of the diseased part are grasped by the grasping forceps.

FIG. 127 is a view showing a method for mucosa separation of the thirteenth embodiment of the present invention, and shows a state where the mucosa around the aperture is incised using the high-frequency knife, while the mucosa and the submucosal layer located in the vicinity of the diseased part are grasped by the grasping forceps.

FIG. 128 is a view showing a state where the balloon insertion portion and the grasping forceps are protruded from the tip of the insertion portion of the endoscope of the thirteenth embodiment of the present invention.

FIG. 129 is a view for comparison with FIG. 128, and shows a state where the balloon insertion portion and the grasping forceps are protruded from the tip of the insertion portion of the endoscope having a structure being different from the endoscope of the thirteenth embodiment.

FIG. 130 is a plan view showing the top end surface of the insertion portion of the endoscope of a fourteenth embodiment of the present invention.

FIG. 131 is a view showing a state where the balloon insertion portion and the grasping forceps are protruded from the tip of the insertion portion of the endoscope of the fourteenth embodiment.

DESCRIPTION OF THE PREFERRED EMBODIMENTS

A first embodiment of a mucosa separation apparatus and a method for mucosa separation of the present invention will be explained with reference to FIG. 1 through FIG. 25.

Figure 1:
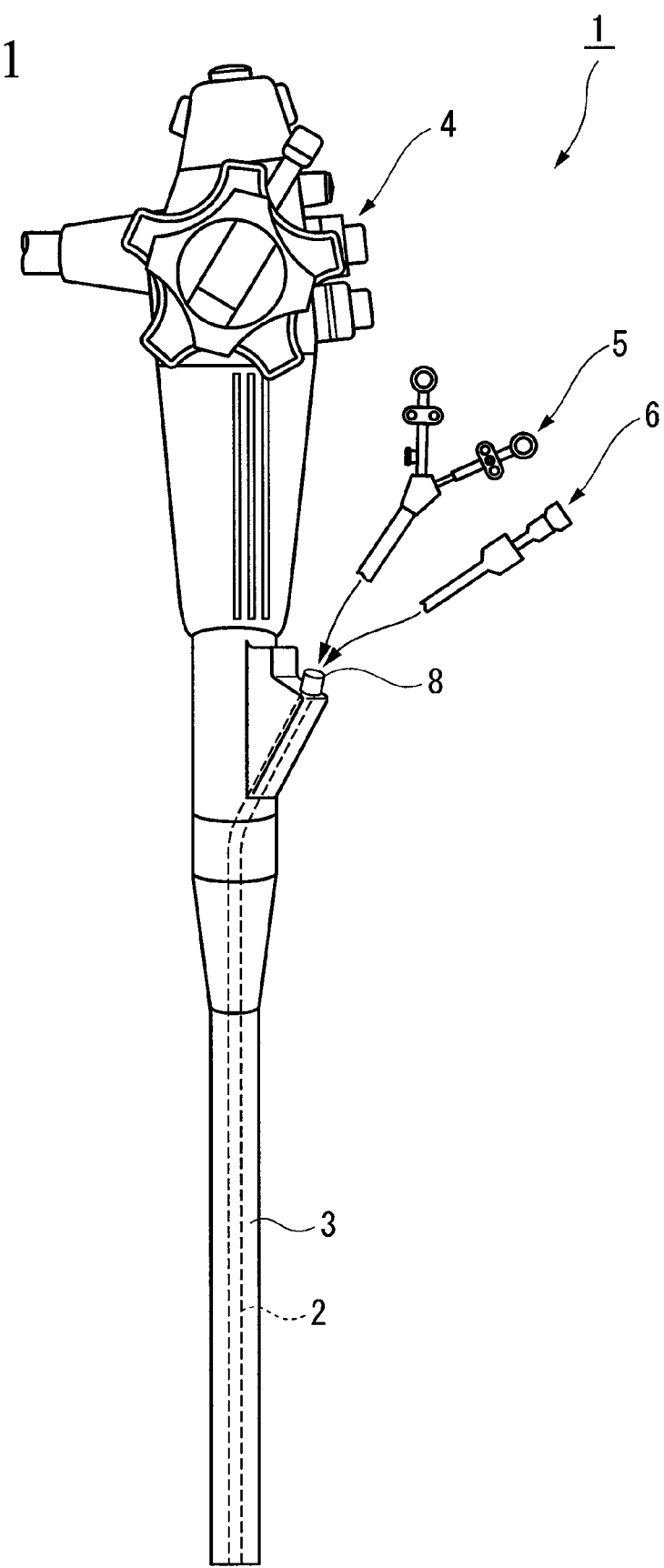
FIG. 1 is a view showing a mucosa separation apparatus of a first embodiment of the present invention, and shows a schematic view of a mucosa separation system including an endoscope, a separation balloon insertion device, and a submucosal local injection needle.

As shown in FIG. 1, a mucosa separation system 1 of this embodiment includes an endoscope 4, a separation balloon insertion device (mucosa separation apparatus) 5, and a submucosal local injection needle 6. A channel 2 is formed within an insertion portion 3 of the endoscope 4. One of the separation balloon insertion device 5 and the submucosal local injection needle 6 is inserted into the channel 2 through a forceps port 8 as appropriate. The aperture of a channel located at the tip of the insertion portion 3 faces forwardly. That is, the endoscope 4 is a straight sight type endoscope.

Figure 2:
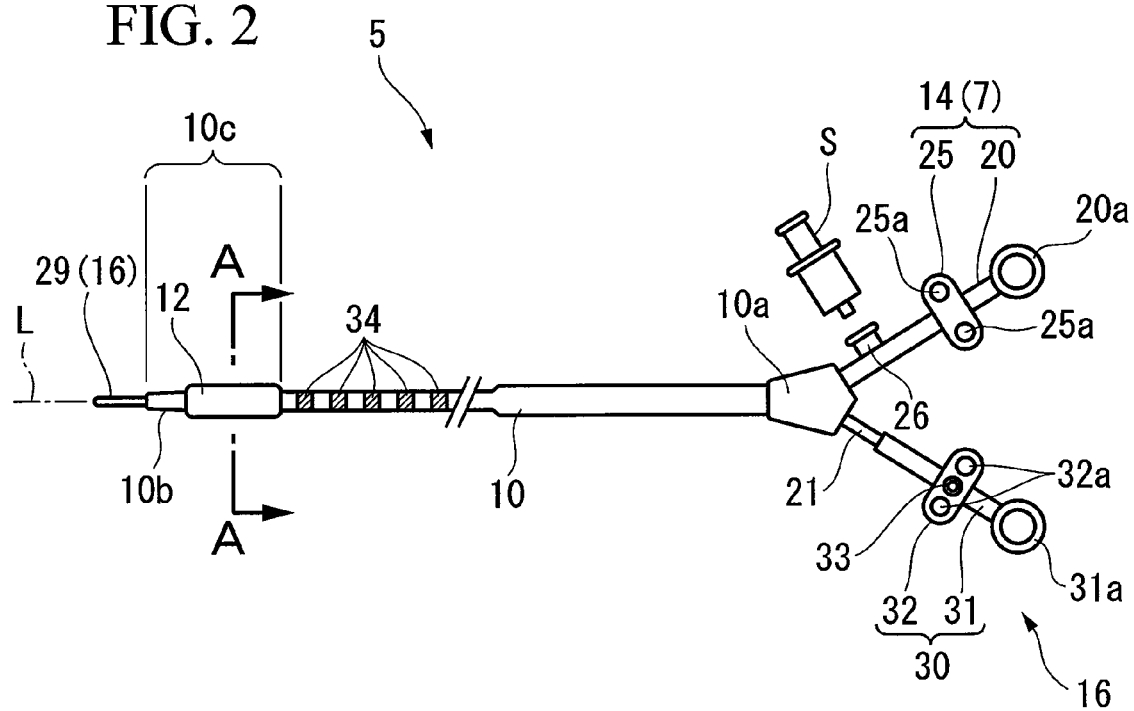
FIG. 2 is a plan view showing the separation balloon insertion device of the first embodiment.

The separation balloon insertion device 5 locally separates a submucosal layer from a muscularis propria, and removes a diseased part of the alimentary tract. As shown in FIG. 2, the separation balloon insertion device 5 includes a balloon insertion portion (first insertion portion) 10 which is flexible, a balloon (expansion portion) 12 disposed on a head portion 10c of the balloon insertion portion 10, and a curving mechanism (curving portion) 7 which curves the head portion 10c of the balloon insertion portion 10.

Figure 3:
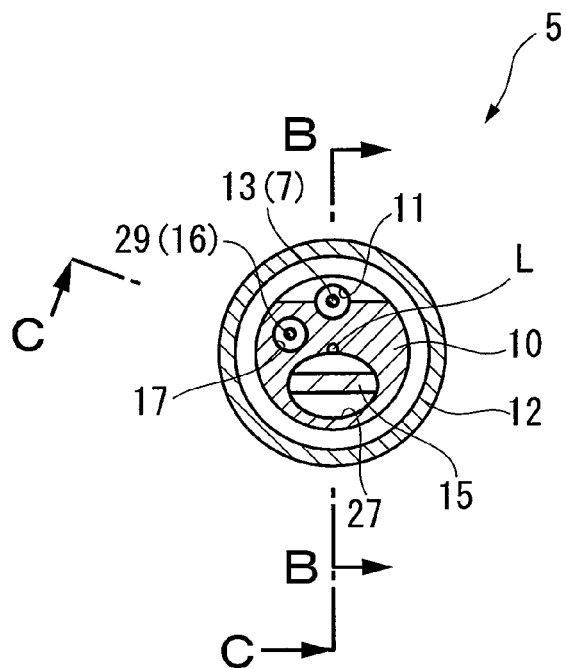
FIG. 3 is a sectional view taken along a line A-A in FIG. 2.

As shown in FIG. 3, the balloon insertion portion 10 has a long tubular body, and a channel 11 is formed within the balloon insertion portion 10 from the terminal of the balloon insertion portion 10 to the tip thereof. The channel 11 is formed at a position which slightly separates from an axis L of the balloon insertion portion 10. The balloon 12 expands by infusion of a fluid such as gas or liquid through the channel 11.

Figure 4:
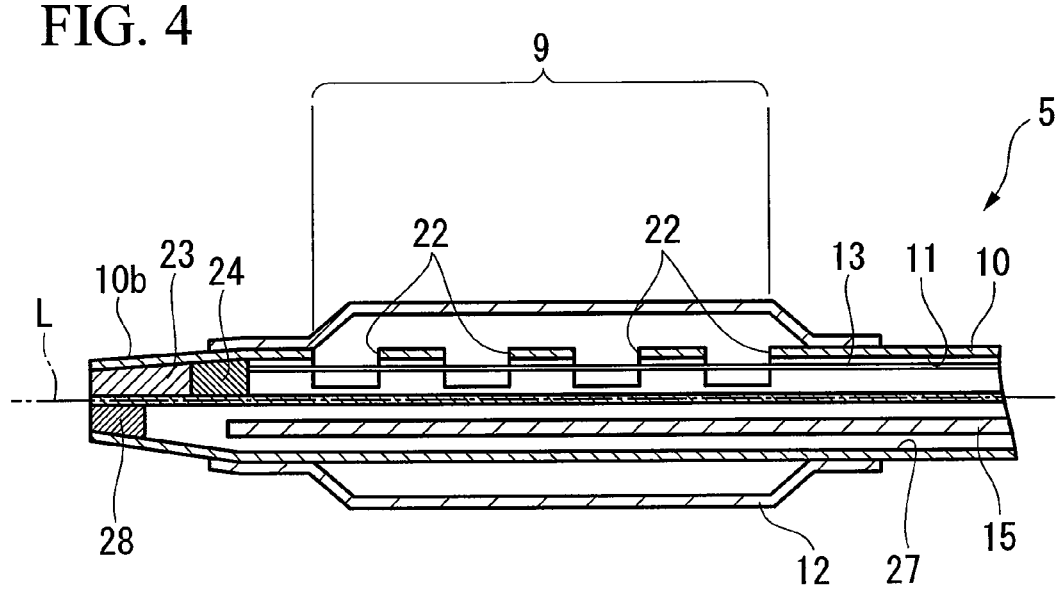
FIG. 4 is a sectional view taken along a line B-B in FIG. 3.

As shown in FIG. 2 through FIG. 4, the curving mechanism 7 includes an operation wire 13, and an operation section 14. The operation wire 13 is inserted into the channel 11. One end of the operation wire 13 is connected to an operation wire fixed portion 24 attached to apart of the head portion 10c in the vicinity of the balloon 12. The operation section 14 is disposed on a base portion of the balloon insertion portion 10.

Figure 5:
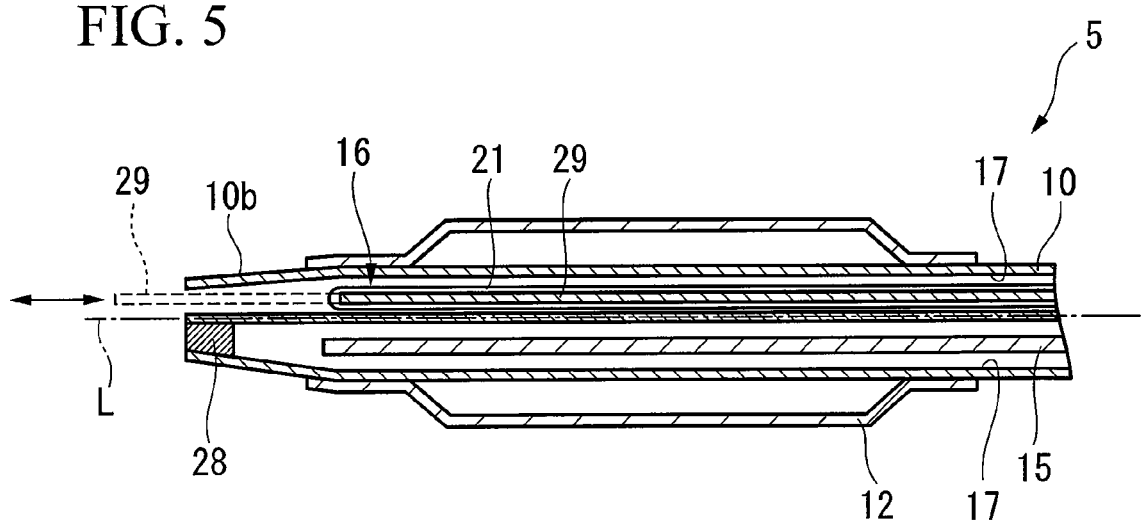
FIG. 5 is a sectional view taken along a line C-C in FIG. 3.

A channel 17 for inserting a high-frequency knife 16 thereinto is formed within the balloon insertion portion 10 along the channel 11. A plate member (first curving support member) 15 is disposed inside the head portion 10c of the balloon insertion portion 10 along the longitudinal direction thereof. The plate member 15 has the sectional characteristic to incline to be flexible in a particular direction. As shown in FIG. 2, a connecting portion 10a is disposed on the base portion of the balloon insertion portion 10. An operation section main body 20 of the operation section 14 and an operation tube 21 of the high-frequency knife 16 are provided to the connection portion 10a so that the operation section main body 20 and the operation tube 21 are separate from each other. As shown in FIG. 4 and FIG. 5, a top end 10b of the balloon insertion portion 10 is formed like a tapered shape so as the diameter thereof gradually reduces toward the top end.

As shown in FIG. 2 and FIG. 3, the balloon 12 is disposed on a part of the balloon insertion portion 10 which is closer to the base portion the balloon insertion portion 10 than the top end 10b so as to cover around the balloon insertion portion 10. As shown in FIG. 4, a number of communication holes 22 which communicate the channel 11 with the inside space of the balloon 12 are formed in the balloon insertion portion 10 covered by the balloon 12. The communication holes 22 are arranged in line along the longitudinal direction of the balloon insertion portion 10. A sealing member 23 which seals the channel 11 is disposed inside the top end 10b, and the operation wire fixed portion 24 is attached to the sealing member 23. Therefore, the fluid which has been supplied into the channel 11 is flowed to the balloon 12 through the communication holes 22 without leakage from the tip of the channel 11.

As shown in FIG. 2, the operation section 14 includes an operation section main body 20, and a sliding portion 25 which is slidable with respect to the operation section main body 20. The other end of the operation wire 13 inserted into the channel 11 is connected to the sliding portion 25. When the operation section 14 is operated, in other words, when the sliding portion 25 is slid forward or backward with respect to the operation section main body 20, the head portion 10c of the balloon insertion portion 10 including the entire balloon 12 is curved with respect to a part of the balloon insertion portion 10 which is closer to the base portion thereof than the head portion 10c. Particular explanation thereof will be given below.

As shown in FIG. 2, a finger hanging ring 20a on which a thumb of an operator can be hanged is attached to the terminal of the operation section main body 20. Two finger hanging holes 25a on which a forefinger and a middle finger of the operator can be respectively hanged are formed in the sliding portion 25. The operator hangs the thumb of one hand on the finger hanging ring 20a, and hangs each of the forefinger and the middle finger of the one hand on the finger hanging holes 25a of the sliding portion 25. Thereby, he/she can easily operate the curving operation of the balloon insertion portion 10 using only one hand. A fill port 26 which communicates with the channel 11 is disposed in the vicinity of the connecting portion 10a of the operation section main body 20. A syringe S performing as a fluid supply source which supplies the fluid for expanding the balloon 12 is connected to the fill port 26.

Figure 6:
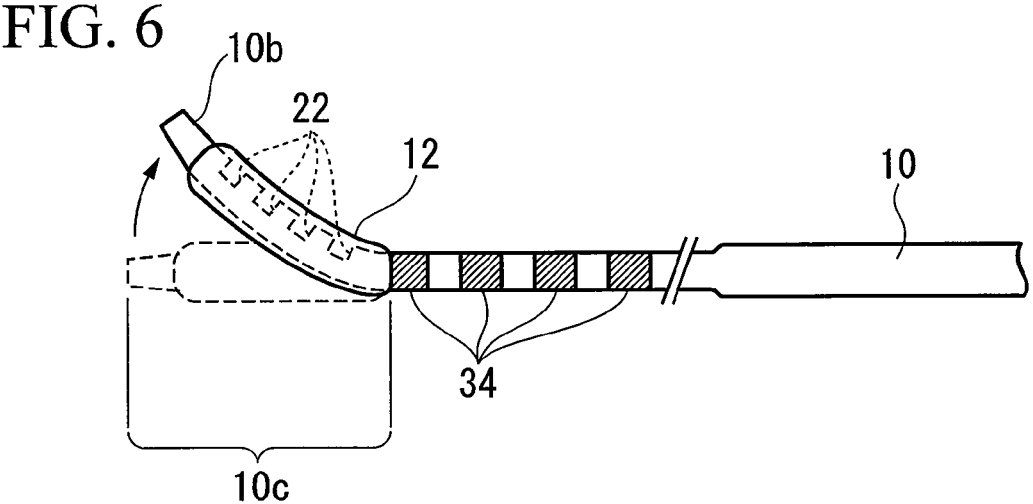
FIG. 6 is a view showing a head portion of the separation balloon insertion device of the first embodiment in a state where such head portion is curved upward.
Figure 7:
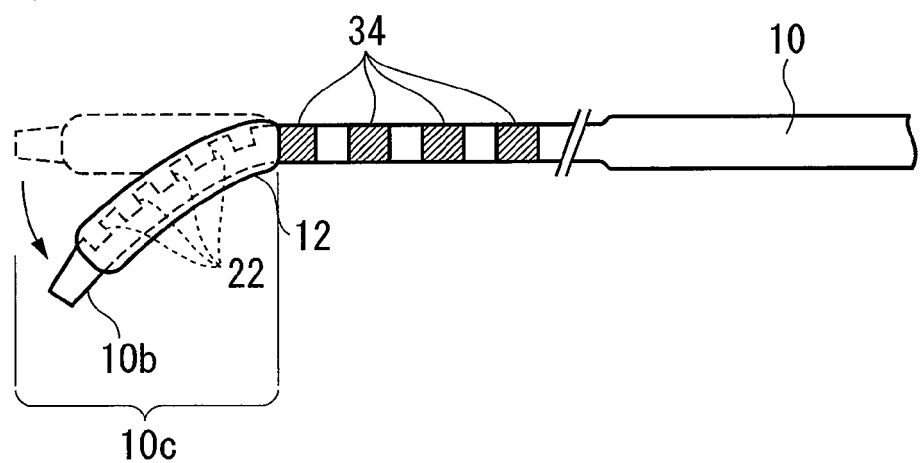
FIG. 7 is a view showing the head portion of the separation balloon insertion device of the first embodiment in a state where such head portion is curved downward.

Since the communication holes 22 are formed in a part of the head portion 10c of the balloon insertion portion 10, the part is more flexible than the other part of the head portion 10c of the balloon insertion portion 10. When a predetermined strength force acts on an area in which the communication holes 22 are formed, the area performs as a first flexible portion 9 which is curved before curving of the other area. Therefore, when the operation section 14 is operated, the head portion 10c of the balloon insertion portion 10 is easily curved centering around the area in which the communication holes 22 are formed. That is, when the sliding portion 25 is pulled toward the terminal of the operation section main body 20, as shown in FIG. 6, the head portion 10c of the balloon insertion portion 10 including the entire balloon 12 is curved so as to turn up a surface of the part on which the communication holes 22 are formed. When the sliding portion 25 is pushed toward the tip of the operation section main body 20, as shown in FIG. 7, the head portion 10c of the balloon insertion portion 10 including the entire balloon 12 is curved so as to turn up an opposite surface of the surface of the part on which the communication holes 22 are formed.

It is preferable that the communication holes 22 be formed in an area which is separate at least 5 millimeters or more away from the tip of the balloon insertion portion 10. Further, it is more preferable that the communication holes 22 be formed in an area which is separate 10-15 millimeters from the tip of the balloon insertion portion 10.

The plate member 15 is made of an elastic material such as metal or plastic. As shown in FIG. 3 and FIG. 4, the plate member 15 is formed like a narrow reed-shape. The plate member 15 has the sectional characteristic to incline to be flexible in the thickness direction thereof, and is disposed on the opposite side of the channel 11 across the axis L so that the thickness direction of the plate member 15 conforms to a direction being from the operation wire 13 to the axis L. In other words, a direction in which the plate member 15 inclines to curve conforms to a direction in which the head portion 10c of the balloon insertion portion 10 must be curved. Therefore, the head portion 10c of the balloon insertion portion 10 inclines to curve in the thickness direction of the plate member 15, and inclines to hardly curve in the width direction of the plate member 15.

A channel 27 for inserting the plate member 15 thereinto is formed within the balloon insertion portion 10. The plate member 15 is inserted into the channel 27 from the tip of the balloon insertion portion 10, and is held inside the channel 27 depending on the frictional force between the plate member 15 and an inside wall surface of the channel 27. A sealing member 28 which seals the channel 27 is disposed within the top end 10b of the balloon insertion portion 10.

As shown in FIG. 2 and FIG. 5, the high-frequency knife 16 includes the operation tube 21, a knife portion 29 formed like a needle, and a knife operation section 30. The operation tube 21 is made of an insulating material, and is connected to the connection portion 10a. One end of the operation tube 21 is inserted into the channel 17 until the one end of the operation tube 21 approaches the vicinity of the top end 10b of the balloon insertion portion 10. The other end of the operation tube 21 is protruded from the connection portion 10a. The knife portion 29 is disposed within the operation tube 21 so as to be allowed to go forwards and backwards.

The knife operation section 30 includes a knife operation section main body 31 connected to the other end of the operation tube 21, and a knife sliding portion 32 connected to the terminal of the knife portion 29 and which is allowed to go forwards and backwards with respect to the knife operation section main body 31. As shown in FIG. 2, a finger hanging ring 31a on which a thumb of the operator can be hanged is attached to the terminal of the knife operation section main body 31. Two finger hanging holes 32a on which a forefinger and a middle finger of the operator can be respectively hanged are formed in the knife sliding portion 32. The operator hangs the thumb of one hand on the finger hanging ring 31a, and hangs each of the forefinger and the middle finger of the one hand on the finger hanging holes 32a of the knife sliding portion 32. Thereby, he/she can easily operate the knife operation section 30 using only one hand. A power supply connection portion 33 for electrically connecting a high-frequency power supply (not shown) to the knife portion 29 is disposed between the two finger hanging holes 32a of the knife sliding portion 32.

Figure 8:
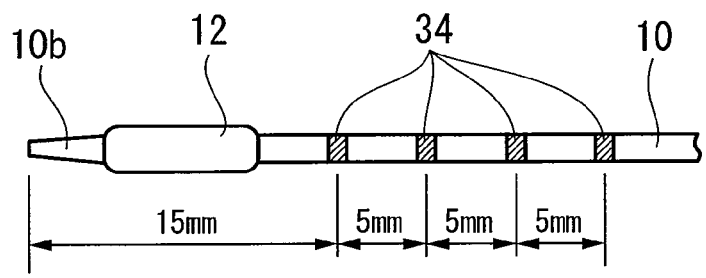
FIG. 8 is a plan view showing indicators provided on an insertion portion of the separation balloon insertion device of the first embodiment.

As shown in FIG. 8, indicators 34 which indicate the insertion quantity of the head portion 10c of the balloon insertion portion 10 into the mucosa, are disposed on an area of the balloon insertion portion 10 which is closer to the base portion thereof than the balloon 12. The indicators 34 are located every 5 millimeters from a point being separate from the top end 10b by 15 millimeters toward the terminal end of the balloon insertion portion 10.

Figure 9:
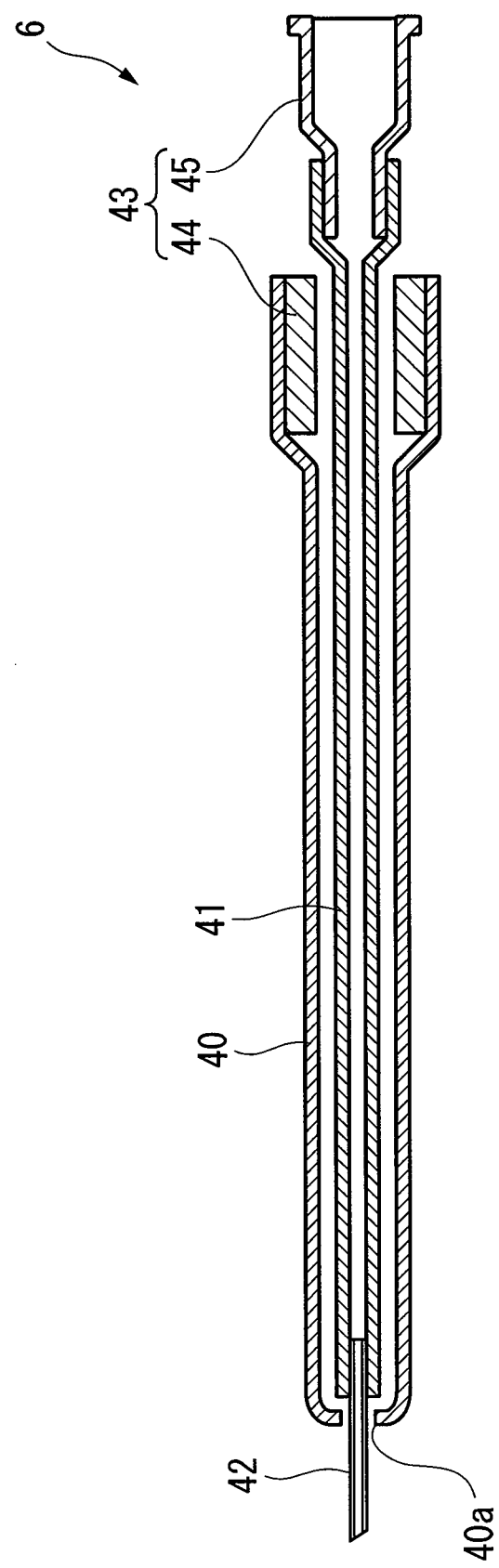
FIG. 9 is a sectional view showing the submucosal local injection needle in which a needle portion protrudes from an outer tube.
Figure 10:
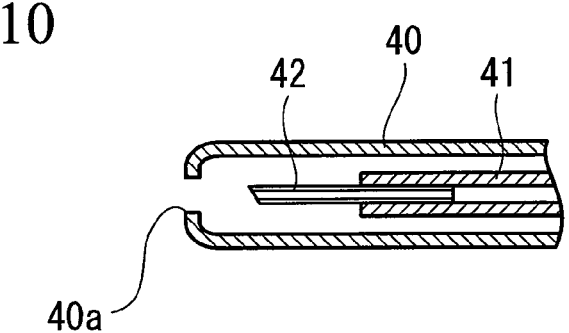
FIG. 10 is a sectional view showing a tip of the submucosal local injection needle which retracts the needle portion into the outer tube.

As shown in FIG. 9 and FIG. 10, the submucosal local injection needle 6 includes an outer tube 40, an inner tube 41 which is allowed to go forwards and backwards inside the outer tube 41, a hollow needle portion 42 attached to the tip of the inner tube 41, and a needle operation section 43 attached to the terminal end of the outer tube 40. A contracted portion is formed in the tip of the outer tube 40, and a small hole 40a through which only the needle portion 42 of the inner tube 41 can be inserted is formed in the center of the contracted portion. The needle operation section 43 includes a needle operation section main body 44, and a sleeve 45 through which fluid for local injection (local injection fluid) is injected. The needle operation section main body 44 is attached to an inside surface of the terminal of the outer tube 40. The sleeve 45 is attached to the terminal end of the inner tube 41. When the sleeve 45 has gone forwards or backwards with respect to the needle operation section main body 44, the needle portion 42 is protruded from and is retracted inside the tip of the outer tube 40.

The method for mucosa separation for removing a diseased part X developing inside an alimentary tract from a submucosal layer W using the mucosa separation system 1 as mentioned above will be explained.

The method for mucosa separation of this embodiment includes a step of inflating the mucosa and the submucosal layer in the vicinity of the diseased part of the alimentary tract, a step of forming an aperture in the mucosa in the vicinity of the diseased part of the alimentary tract, a step of piercing the submucosal layer through the aperture to form an insertion hole substantially parallel to a muscularis propria, a step of separating the submucosal layer from the muscularis propria by expanding the space the inside of the insertion hole, and a step of incising the submucosal layer separated from the muscularis propria to remove the submucosal layer from the alimentary tract. The step of piercing the submucosal layer includes a step of inserting, and a step of angle-adjusting (a step of curving), and a step of length-adjusting (a step of sticking). Each of the steps will be explained.

Figure 11:
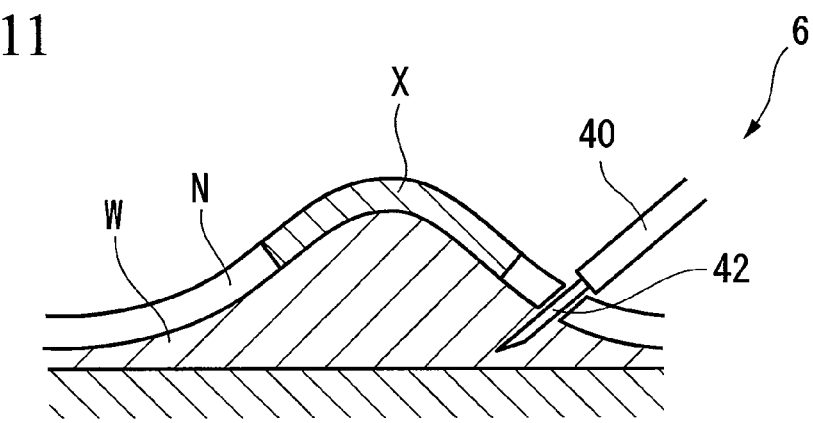
FIG. 11 is a view showing a method for mucosa separation of the first embodiment of the present invention, and shows a state where a diseased part is inflated by injecting a local injection solution into the submucosal layer using the local injection needle.

First, the step of inflating is performed. That is, the endoscope 4 into which the submucosal local injection needle 6 is inserted is inserted into the alimentary tract, and thereafter the tip of the insertion portion 3 is positioned in the vicinity of the diseased part X. While the condition is held, the outer tube 40 of the submucosal local injection needle 6 is protruded from the tip of the insertion portion 3 of the endoscope 4, and the sleeve 45 is moved toward the tip of the needle operation section main body 44, and thereby the needle portion 42 is protruded from the tip of the outer tube 40. As shown in FIG. 11, the needle portion 42 is run through a mucosa N and the submucosal layer W in the vicinity of the diseased part X. After the needle portion 42 is run through, local injection fluid is injected into the submucosal layer W through the inner tube 41 and the needle portion 42. Therefore, the submucosal layer W in the vicinity of the diseased part X is inflated.

After the submucosal layer W in the vicinity of the diseased part X is inflated, the sleeve 45 is moved toward the terminal of the needle operation section main body 44, and thereby the needle portion 42 is retracted into the inner tube 41, and the submucosal local injection needle 6 is drawn out from the channel 2. Note that, the endoscope 4 is not moved, and is held in the position.

Figure 12:
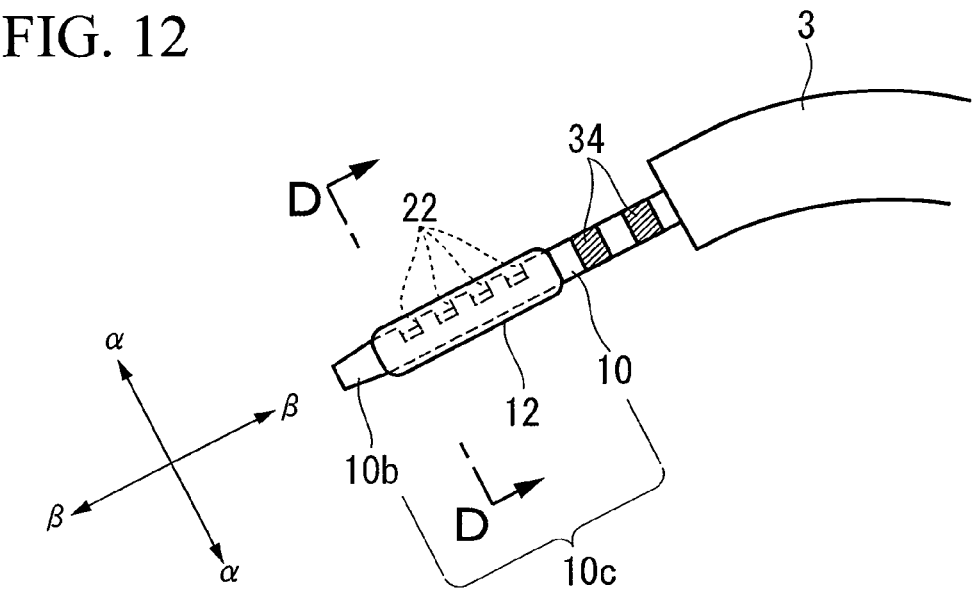
FIG. 12 is a view showing a method for mucosa separation of the first embodiment of the present invention, and shows a state where a balloon insertion portion is protruded from a tip of a insertion portion of the endoscope.

After the step of inflating, the step of aperture-forming is performed. That is, as shown in FIG. 12, the balloon insertion portion 10 of the separation balloon insertion device 5 is inserted into the channel 2, and thereafter the head portion 10c of the balloon insertion portion 10 is protruded from the tip of the insertion portion 3.

Figure 13:
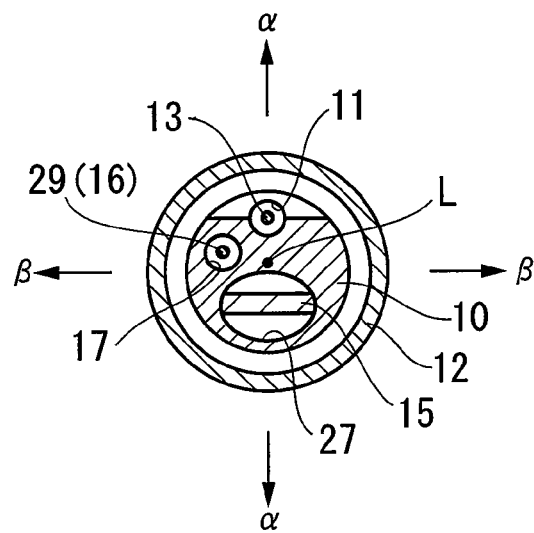
FIG. 13 is a view showing a method for mucosa separation of the first embodiment of the present invention, and shows a sectional view taken along a line D-D in FIG. 12.

Since the plate member 15 is disposed inside the head portion 10c of the balloon insertion portion 10, the head portion 10c of the balloon insertion portion 10 is moved in accordance with a curving angle of the insertion portion 3 while the head portion 10c moves through the channel 2. When the head portion 10c of the balloon insertion portion 10 is protruded from the tip of the insertion portion 3, as shown in FIG. 12 and FIG. 13, a curving direction of the insertion portion 3 (vertical direction) conforms to the thickness direction of the plate member 15 ($\alpha$ direction). The thickness direction of the plate member 15 ($\alpha$ direction), that is a direction in which the plate member 15 inclines to curve conforms to the curving direction of the head portion 10c of the balloon insertion portion 10. Therefore, just the balloon insertion portion 10 of the separation balloon insertion device 5 is inserted into the channel 2, and thereby the curving direction of the head portion 10c of the balloon insertion portion 10 conforms to the curving direction of the insertion portion 3.

Note that, in this embodiment, it is assumed that the area of the balloon insertion portion 10 in which the operation wire 13 and the communication holes 22 are formed is positioned at an upper portion of the insertion portion 3.

Figure 14:
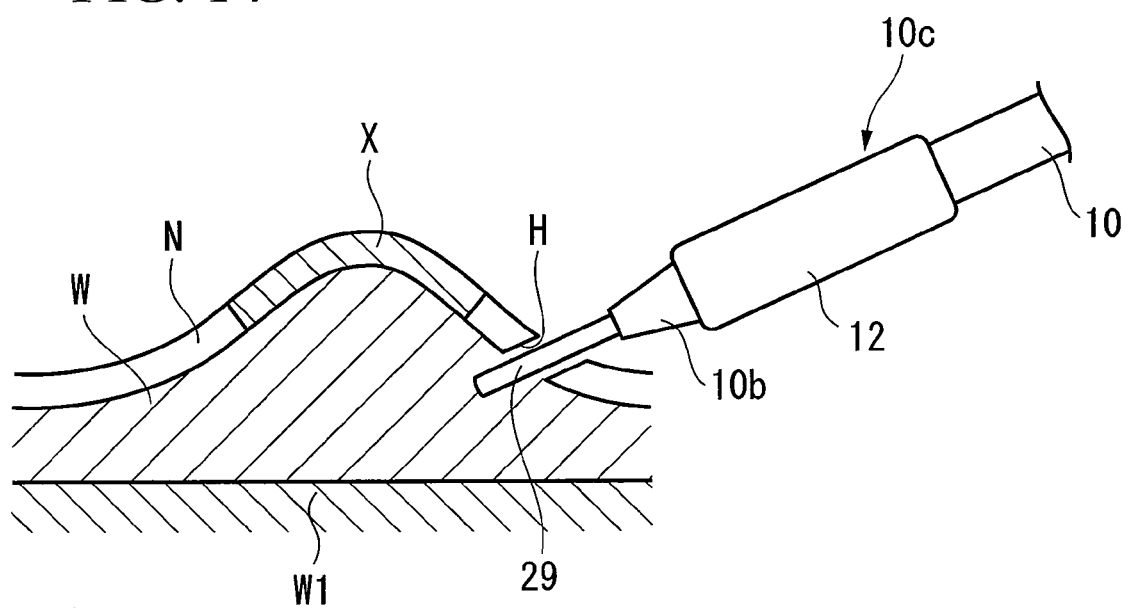
FIG. 14 is a view showing a method for mucosa separation of the first embodiment of the present invention, and shows a state where an aperture is formed in the inflated mucosa using a high-frequency knife after inflating the submucosal layer around the diseased part.

After the head portion 10c of the balloon insertion portion 10 is protruded from the tip of the insertion portion 3, the knife sliding portion 32 is moved toward the tip of the balloon insertion portion 10, and thereby the knife portion 29 is protruded from the operation tube 21, and then it is protruded from the top end 10b of the balloon insertion portion 10. While the condition is held, high-frequency current is supplied to the knife portion 29 from the high-frequency power supply connected to the power supply connection portion 33. As shown in FIG. 14, the knife portion 29 is moved forward, and thereby an aperture H with a predetermined size is formed in the mucosa N in the vicinity of the diseased part X being inflated After the aperture H is formed, supplying of high-frequency current is stopped. The sliding portion 25 is moved toward the tip of the balloon insertion portion 10, and thereby the knife portion 29 is retracted into the operation tube 21.

Figure 15:
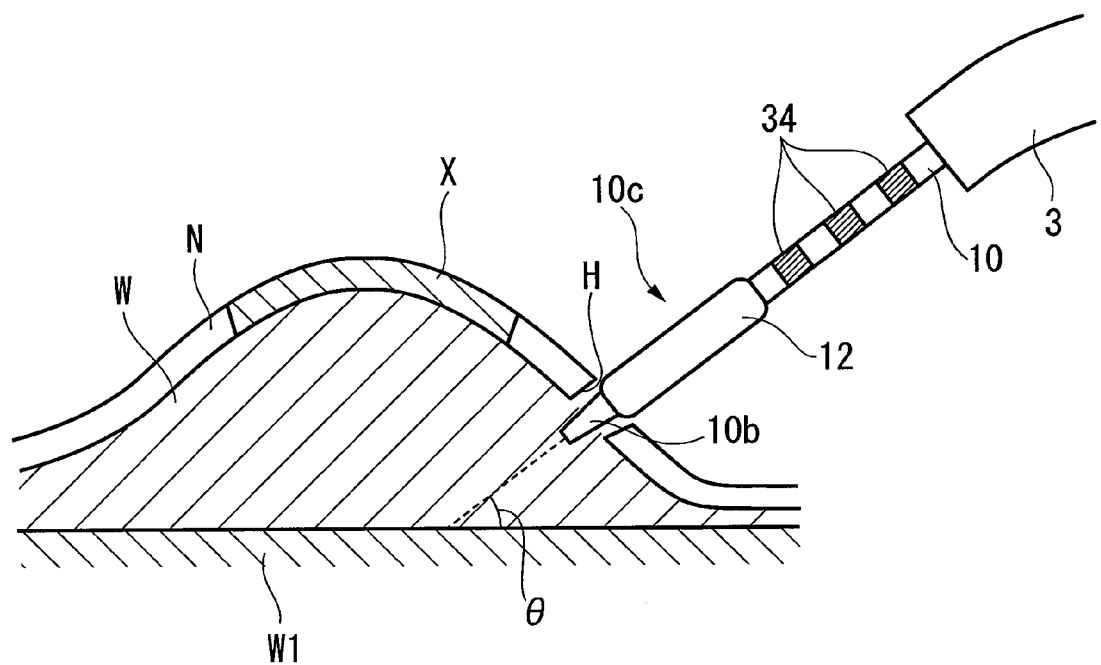
FIG. 15 is a view showing a method for mucosa separation of the first embodiment of the present invention, and shows a state where the tip of the balloon insertion portion is inserted into the aperture after forming the aperture in the mucosa.

After the step of aperture-forming, the step of inserting is performed. That is, as shown in FIG. 15, the top end 10b of the balloon insertion portion 10 is inserted into the submocosa W through the aperture H. At this stage, the head portion 10c of the balloon insertion portion 10 is across a surface of the alimentary tract at an angle θ.

Figure 16:
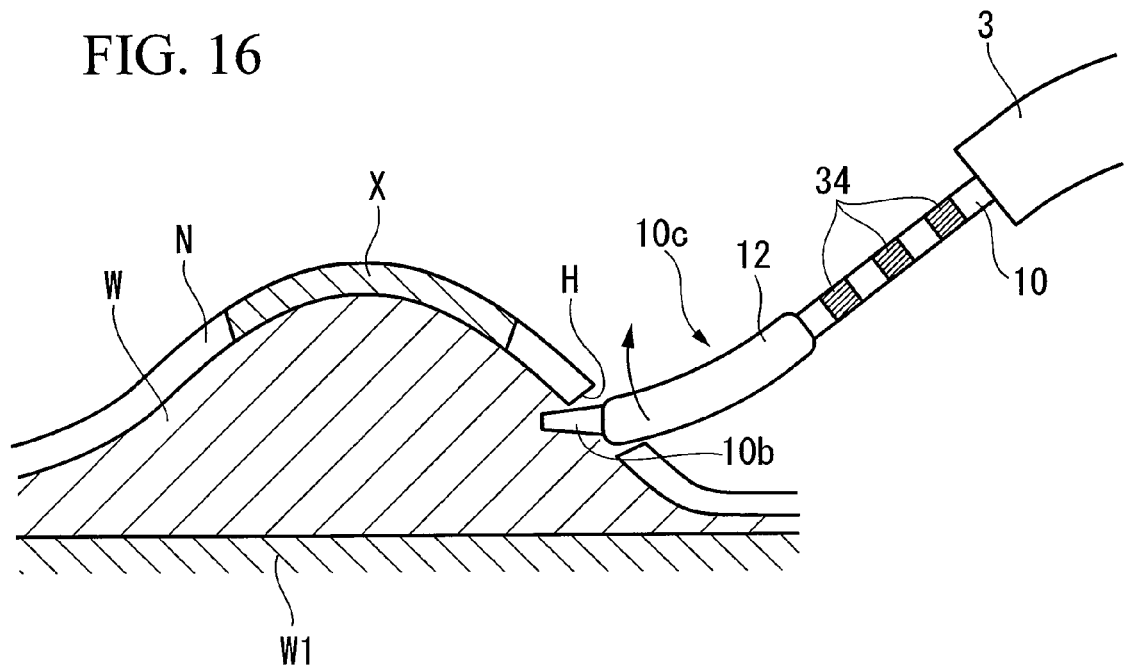
FIG. 16 is a view showing a method for mucosa separation of the first embodiment of the present invention, and shows a state where the head portion of the balloon insertion portion is curved after inserting the tip of the balloon insertion portion into the aperture.

After the step of inserting, the step of angle-adjusting is performed. That is, the sliding portion 25 is moved toward the terminal of the balloon insertion portion 10 with respect to the operation section main body 20, and thereby the operation wire 13 is pulled. Since the one end of the operation wire 13 is connected to the head portion 10c of the balloon insertion portion 10 through the operation wire fixed portion 24, a pull force generated on the operation wire 13 by the pulling operation carries to the head portion 10c of the balloon insertion portion 10. Therefore, a compression force acts on a substantially half part of the balloon insertion portion 10 inside which the operation wire 13 is disposed. In contrast, a pull force acts on a substantially half part of the balloon insertion portion 10 positioned on the opposite side of the operation wire 13 across the axis L. As a result, as shown in FIG. 16, the head portion 10c of the balloon insertion portion 10 including the entire balloon 12 is curved centering around the first flexible portion 9 so that the half part of the balloon insertion portion 10 inside which the operation wire 13 and the communication holes 22 are disposed warps upward of the insertion portion 3.

Otherwise, the sliding portion 25 is moved toward the tip of the balloon insertion portion 10 with respect to the operation section main body 20, and thereby the operation wire 13 is pushed into the channel 11. A pushing force generated on the operation wire 13 by the pushing operation carries to the head portion 10c of the balloon insertion portion 10. Therefore, a pull force acts on the substantially half part of the balloon insertion portion 10 inside which the operation wire 13 is disposed. In contrast, a compression force acts on the substantially half part of the balloon insertion portion 10 positioned on the opposite side of the operation wire 13 across the axis L. As a result, the head portion 10c of the balloon insertion portion 10 including the entire balloon 12 warps downward of the insertion portion 3.

By performing the pulling and pushing operation, the head portion 10c of the balloon insertion portion 10 can be curved so that the head portion 10c of the balloon insertion portion 10 is substantially parallel to the surface of the alimentary tract.

Figure 17:
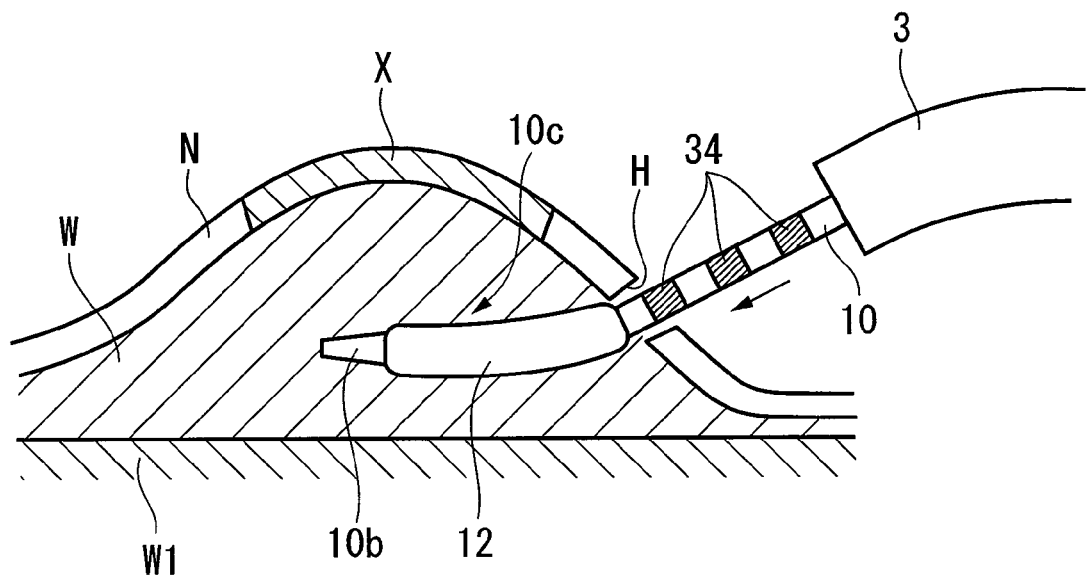
FIG. 17 is a view showing a method for mucosa separation of the first embodiment of the present invention, and shows a state where the balloon insertion portion pierces the submucosal layer after curving the head portion of the balloon insertion portion.
Figure 18:
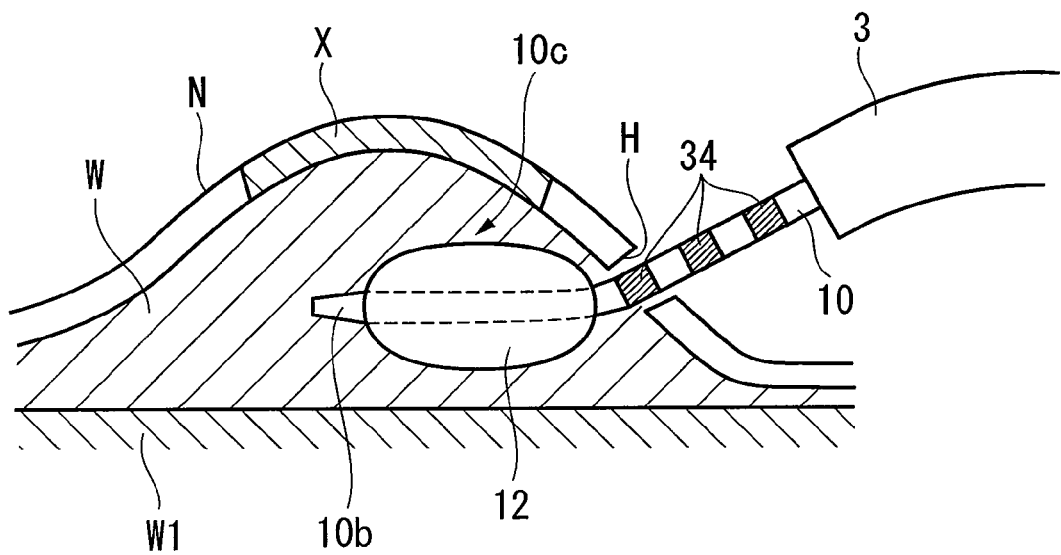
FIG. 18 is a view showing a method for mucosa separation of the first embodiment of the present invention, and shows a state where a balloon is expanded within the submucosal layer after piercing the submucosal layer by the balloon insertion portion.

After the step of angle-adjusting, the step of length-adjusting is performed. That is, as shown in FIG. 17, the balloon insertion portion 10 is moved along a direction being parallel to the surface of the alimentary tract, and thereby the head portion 10c of the balloon insertion portion 10 is pushed into the submucosal layer W through the aperture H, and then the head portion 10c is put in a predetermined position according to the indicators 34 as guides.

Figure 19:
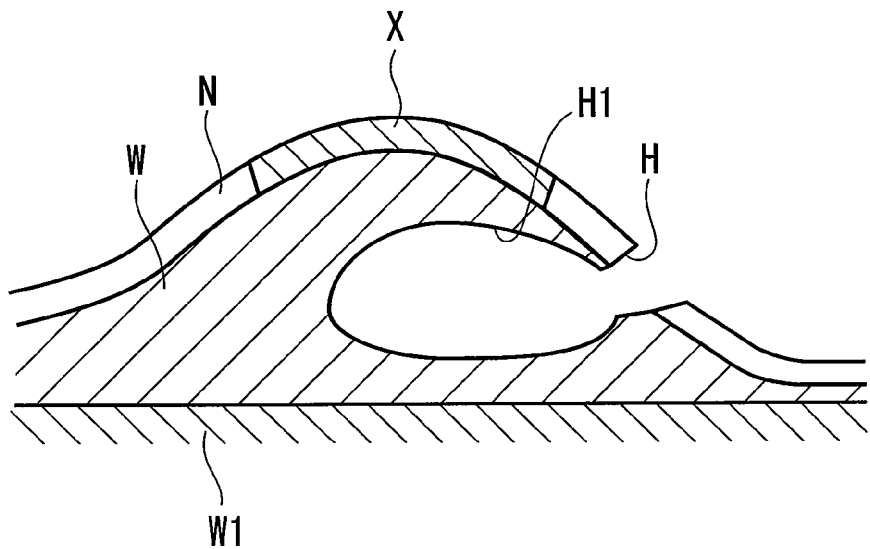
FIG. 19 is a view showing a method for mucosa separation of the first embodiment of the present invention, and shows a state where the balloon insertion portion is retracted from the submucosal layer with the contracted balloon after expanding the balloon within the submucosal layer.

After the step of length-adjusting, the step of separating is performed. That is, a fluid is supplied into the channel 11 through the fill port 26 using a syringe S. The fluid supplied into the channel 11 is supplied to the balloon 12 through the communication holes 22, and thereby the balloon 12 is inflated (shown in FIG. 18). Therefore, a part of the submucosal layer W is separated from a muscularis propria W1 existing under the submucosal layer W. Then, the fluid is discharged from the balloon 12 through the fill port 26, and thereby the balloon 12 deflates to its original shape. As a result, as shown in FIG. 19, a cavity H1 is formed between the muscularis propria W1 and the submucosal layer W separated from the muscularis propria W1.

Figure 20:
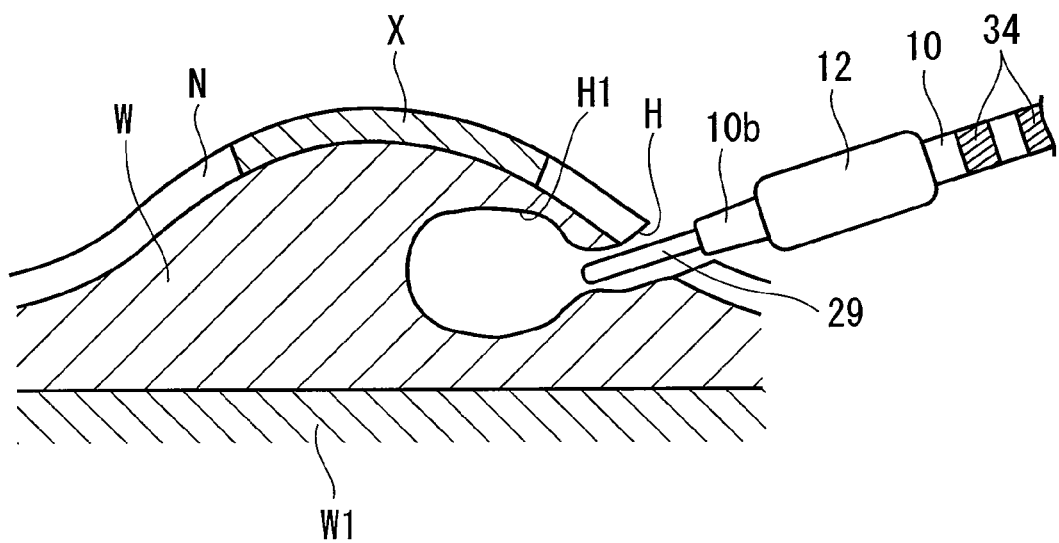
FIG. 20 is a view showing a method for mucosa separation of the first embodiment of the present invention, and shows a state where the high-frequency knife has been inserted into the aperture after retracting the balloon insertion portion from the submucosal layer.
Figure 21:
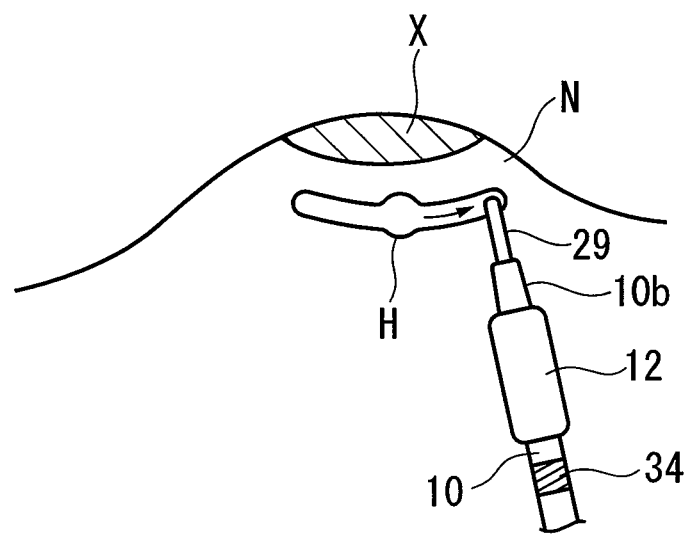
FIG. 21 is a view showing a method for mucosa separation of the first embodiment of the present invention, and shows a state where the mucosa around the aperture is incised using the high-frequency knife after inserting the high-frequency knife into the aperture.

After the step of separating, the step of incising is performed. That is, as shown in FIG. 20, the balloon insertion portion 10 is pulled back from the submucosal layer W until the outside of the aperture H. And then, the knife portion 29 is protruded from the top end 10b of the balloon insertion portion 10, and is inserted into the aperture H. While the condition is held, high-frequency current is supplied to the knife portion 29, and the knife portion 29 is moved around the diseased part X. Therefore, as shown in FIG. 21, the mucosa N around the aperture H is incised. After the mucosa N has been incised with a certain measure of width, supplying of high-frequency current is stopped, and the knife portion 29 is retracted into the operation tube 21.

Figure 22:
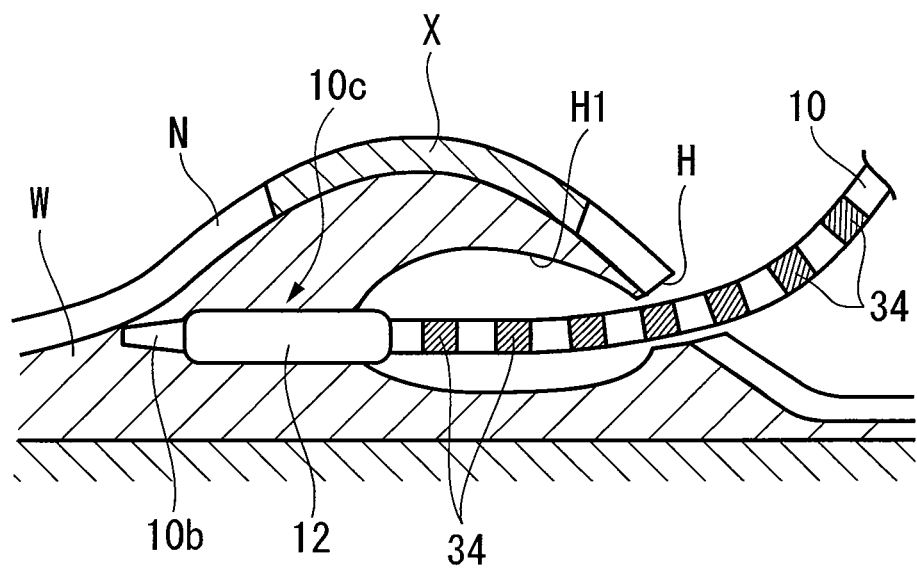
FIG. 22 is a view showing a method for mucosa separation of the first embodiment of the present invention, and shows a state where the balloon insertion portion pierces the submucosal layer again after incising the mucosa around the aperture.
Figure 23:
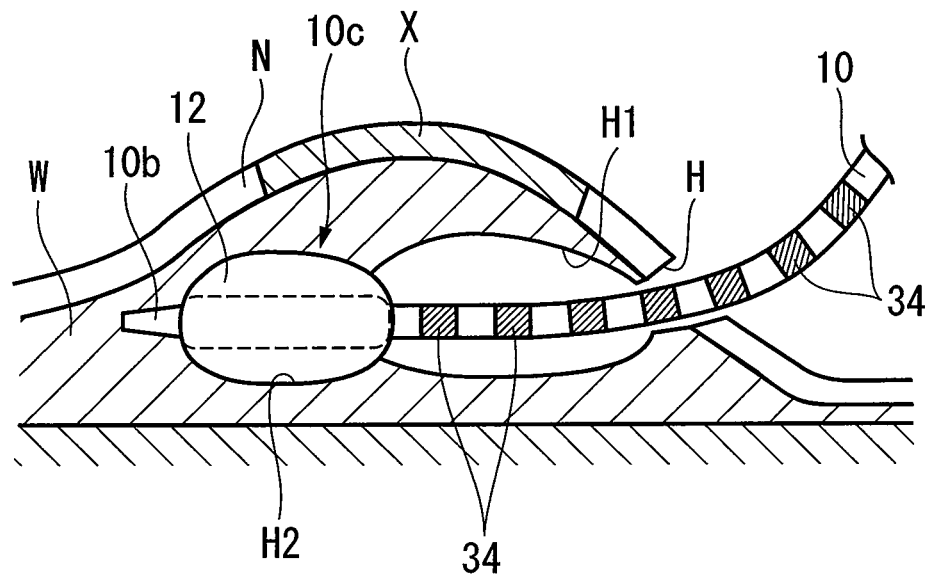
FIG. 23 is a view showing a method for mucosa separation of the first embodiment of the present invention, and shows a state where the balloon is expanded within the submucosal layer again after re-piercing the submucosal layer by the balloon insertion portion.
Figure 24:
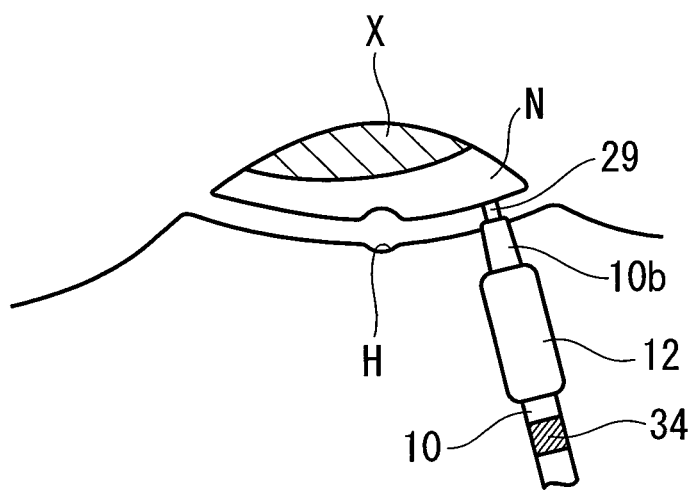
FIG. 24 is a view showing a method for mucosa separation of the first embodiment of the present invention, and shows a state where the mucosa around the aperture is further incised using the high-frequency knife after re-expanding the balloon within the submucosal layer.

If it is impossible to separate the mucosa N including the diseased part X from the submucosal layer W by only the cavity H1 because the diseased part X is so large, the steps of length-adjusting, separating and incising are repeated. That is, as shown in FIG. 22, the head portion 10c of the balloon insertion portion 10 is inserted into the submucosal layer W through the aperture H again, and is put in the predetermined position according to the indicators 34 as guides. Then, as shown in FIG. 23, the balloon 12 is inflated, and thereby the submucosal layer W which has not been separated from the muscularis propria W1 in the first step of separating is separated from the muscularis propria W1, and a new cavity H2 is formed. And then, as shown in FIG. 24, the step of incising is performed again.

Figure 25:
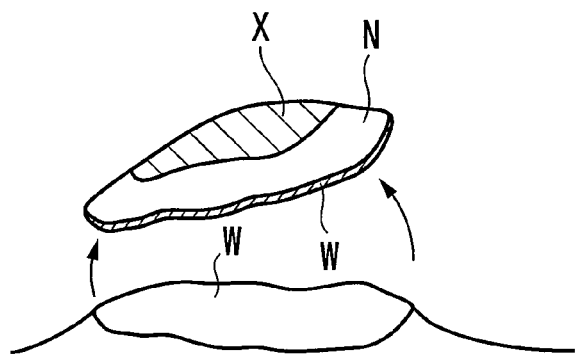
FIG. 25 is a view showing a method for mucosa separation of the first embodiment of the present invention, and shows a state where the mucosa including the diseased part is removed from the alimentary tract after further incising the mucosa around the aperture using the high-frequency knife.

As mentioned above, the steps of length-adjusting, separating and incising are repeated in accordance with the size of the diseased part X. Therefore, as shown in FIG. 25, the submucosal layer W including the diseased part X is removed from the alimentary tract.

According to the mucosa separation apparatus and the method for mucosa separation of this embodiment, the balloon insertion portion 10 is inserted into the submucosal layer W several times, and the balloon 12 is inflated each time. Therefore, it is possible to reliably separate the submucosal layer W from the muscularis propria W1 over a wide area without using the high-frequency knife 16 many times. Further, since the separating of the submucosal layer W can be easily performed by supplying the fluid to the balloon 12, it is possible to shorten the time for the operations. Furthermore, if bleeding from the diseased part X is caused, the part from which there is bleeding is compressed by inflating the balloon 12, and thereby the bleeding can be stopped so quickly. As a result, it is possible to prevent an adventitious disease from being caused at the submucosal layer W of the diseased part X.

The head portion 10c of the balloon insertion portion 10 including the entire balloon 12 is curved, and thereby the head portion 10c becomes substantially parallel to the surface of the alimentary tract. Since the balloon 12 can be inserted into the submucosal layer W while the condition of the head portion 10c is held, the top end 10b of the balloon insertion portion 10 is not pierced to the muscularis propria W1 under the submucosal layer W. Therefore, it is unnecessary for the operator to pay extreme attention about the insertion amount of the head portion 10c of the balloon insertion portion 10. As a result, it is possible to safely perform the procedure regardless of the skill level of the operator, thus it is possible to severely reduce the burden of the operator.

Since the communication holes 22 which perform as the first flexible portion 9 are formed in the head portion 10c of the balloon insertion portion 10, the head portion 10c of the balloon insertion portion 10 can be easily curved. Therefore, if the head portion 10c of the balloon insertion portion 10 is only a little protruded from the channel 2 of the endoscope 4, it is possible to reliably perform the curving operation of the head portion 10c of the balloon insertion portion 10, thus it is possible to reliably perform the procedure in a narrow space within the alimentary tract.

Since the channel 11 is used as a supply passage for supplying the fluid to the balloon 12, and is used as a passage for inserting the operation wire 13, it is possible to reduce the diameter of the balloon insertion portion 10. In addition, since the fluid is effectively supplied to the balloon 12 through the communication holes 22, it is possible to shorten the time of inflating the balloon 12.

Since the plate member 15 is disposed inside the head portion 10c of the balloon insertion portion 10, the curving direction of the head portion 10c of the balloon insertion portion 10 automatically conforms to the curving direction of the insertion portion 3 of the endoscope 4. Accordingly, the head portion 10c of the balloon insertion portion 10 can be operated to curve in substantially the same direction as the curving direction of the insertion portion 3 without adjusting the curving direction of the head portion 10c of the balloon insertion portion 10 separately from the operation of the insertion portion 3. Therefore, the angle of the head portion 10c of the balloon insertion portion 10 with respect to the surface of the alimentary tract can be adjusted easily. As a result, it is possible to shorten the time of the procedure for separating the submucosal layer W from the muscularis propria W1.

Since the channel 17 in which the high-frequency knife 16 is inserted is formed in the balloon insertion portion 10, it is possible to quickly use the high-frequency knife 16 without replacing of the instruments as appropriate. As a result, it is possible to shorten the operation time. Further, it is possible to perform various procedures.

Since the indicators 34 are disposed on the balloon insertion portion 10, it is possible to exactly know the position of the balloon 12 inserted into the submucosal layer W. As a result, it is possible to exactly separate a desired part under the submucosal layer W from the muscularis propria W1.

Next, a second embodiment of a mucosa separation apparatus and a method for mucosa separation of the present invention will be explained with reference to FIG. 26 through FIG. 29. Note that, the same descriptive symbols are used for component elements that are the same as those used in the first embodiment and a description thereof is omitted.

In the separation balloon insertion device 5 of the first embodiment, the operation section 14 is pushed into or pulled out, and thereby the head portion 10c of the balloon insertion portion 10 including the balloon 12 can be curved. In a separation balloon insertion device (mucosa separation apparatus) 50 of the second embodiment, the operation section 14 is rotated, and thereby the head portion 10c of the balloon insertion portion 10 can be rotated around the axis L of the balloon insertion portion 10 in addition to the curving operation of the head portion 10c using the operation section 14.

Figure 26:
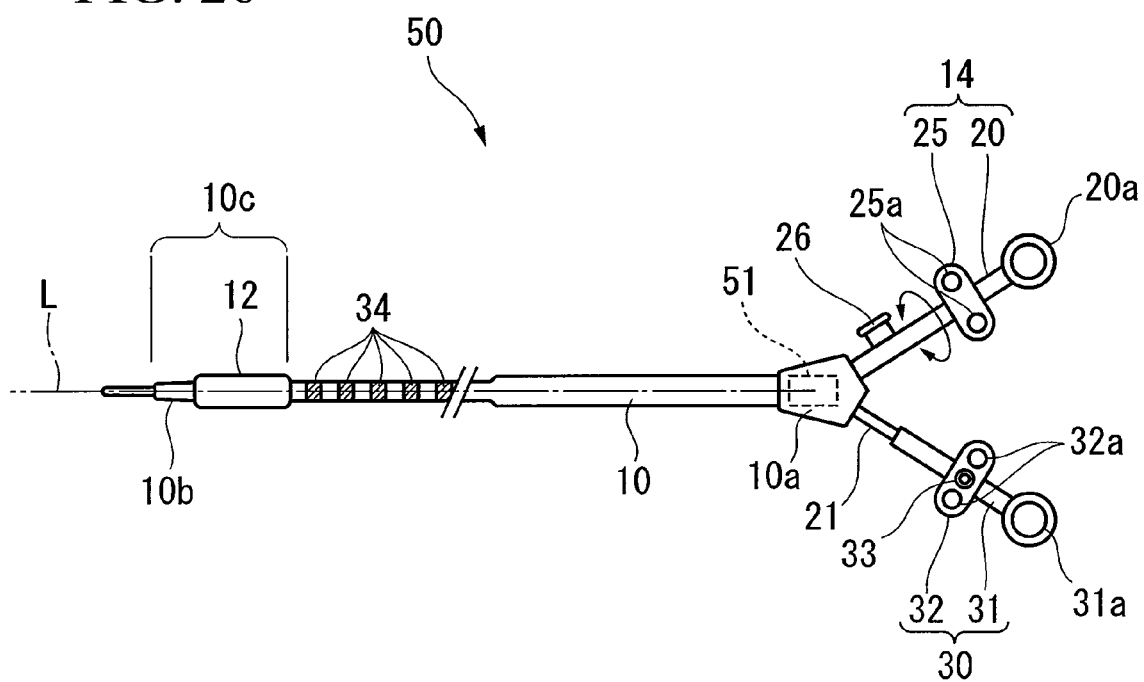
FIG. 26 is a plan view showing a separation balloon insertion device of a second embodiment of the present invention.
Figure 27:
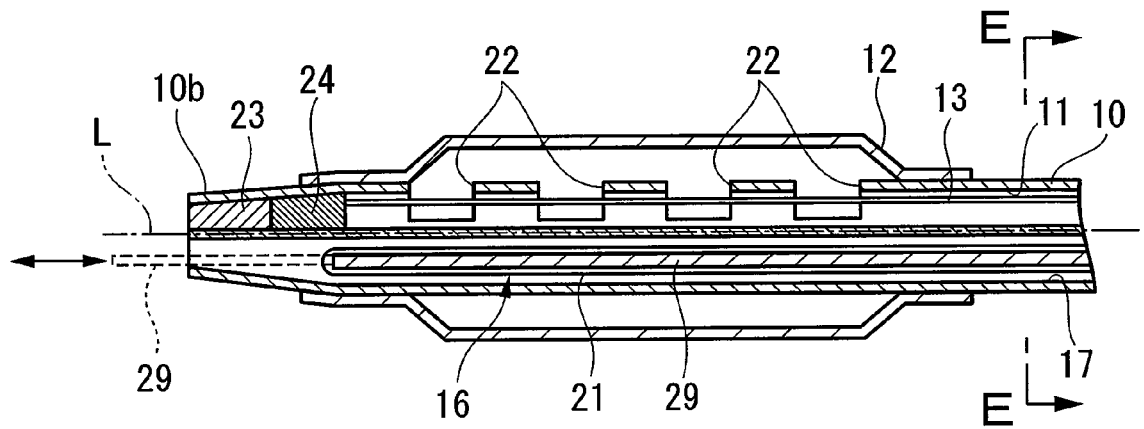
FIG. 27 is a sectional view showing a head portion of the separation balloon insertion device of the second embodiment.
Figure 28:
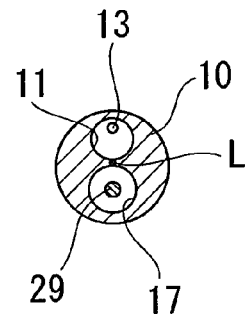
FIG. 28 is a sectional view taken along a line E-E in FIG. 27.

In the balloon insertion portion 10 of the separation balloon insertion device 50 of this embodiment, as shown in FIG. 26 through FIG. 28, the channels 11 and 17 are arranged across the axis L. Further, the operation section main body 20 is rotatably connected to the connection portion 10a. Therefore, the sliding portion 25 rotatably attached to the operation section main body 20 can be also rotated with the operation section main body 20. Furthermore, a rotation transmission portion 51 which transmits a rotation torque (rotation force) from the operation section 14 to the operation wire 13 is disposed on the connection portion 10a. The rotation transmission portion 51 reliably transmits the rotation torque generated by rotating the operation section main body 20 to the operation wire 13.

Note that, it is preferable that the operation wire 13 be a wire having high torque transmissibility, that is, a wire having high torsional rigidity.

The method for mucosa separation for removing a diseased part X developing inside the alimentary tract from the submucosal layer W using the separation balloon insertion device 50 as mentioned above will be explained.

The method for mucosa separation of this embodiment includes the steps of inflating, aperture-forming, angle-adjusting, length-adjusting, separating and incising. Each of the steps will be explained.

Figure 29:
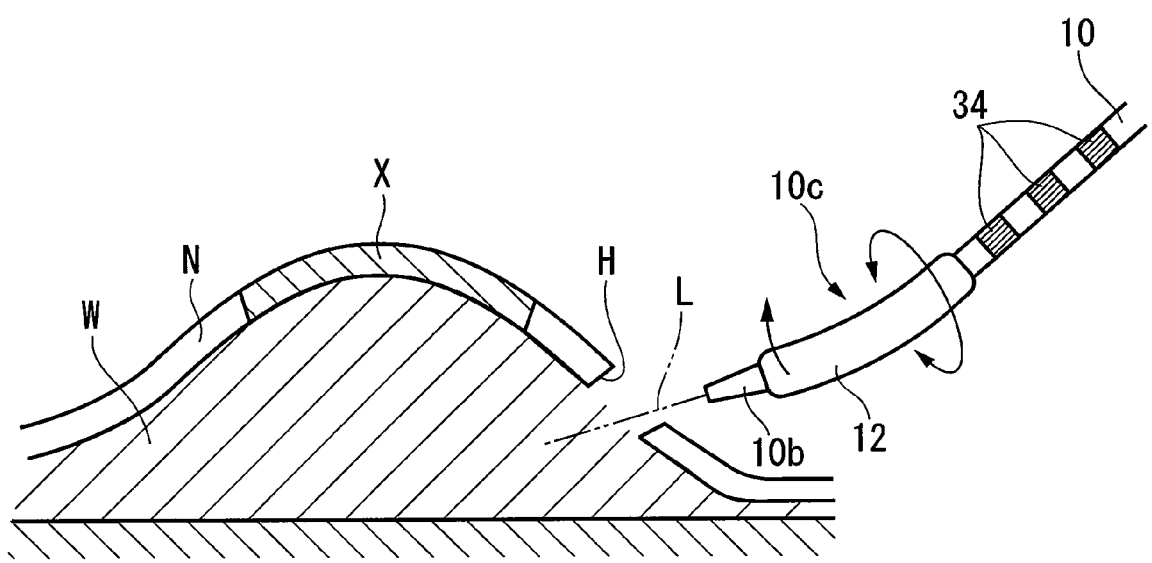
FIG. 29 is a view showing a method for mucosa separation of the second embodiment of the present invention, and shows a state where the head portion of the balloon insertion portion is rotated around an axis thereof in the vicinity of an aperture along with curving the head portion of the balloon insertion portion after forming the aperture in the mucosa.

First, similar to the first embodiment, the steps of inflating and aperture-forming are performed. After that, the step of angle-adjusting is performed. That is, as shown in FIG. 29, the head portion 10c of the balloon insertion portion 10 is positioned in the vicinity of the aperture H. While the condition is held, the sliding portion 25 is moved toward the terminal end of the balloon insertion portion 10 with respect to the operation section main body 20, and thereby the head portion 10c of the balloon insertion portion 10 including the entire balloon 12 is curved. Further, at the same time as the curving operation, the operation section main body 20 and the sliding portion 25 are rotated, and thereby the head portion 10c of the balloon insertion portion 10 including the entire balloon 12 is rotated around the axis L. As mentioned above, the curving operation is performed in combination with the rotation operation, and thereby the head portion 10c of the balloon insertion portion 10 is curved upward. Therefore, the direction of the head portion 10c can be adjusted so as to be parallel to the surface of the alimentary tract.

After the step of angle-adjusting, the step of length-adjusting is performed. That is, the balloon insertion portion 10 is moved along a direction being parallel to the surface of the alimentary tract, and thereby the head portion 10c of the balloon insertion portion 10 is pushed into the submucosal layer W through the aperture H, and is positioned at the predetermined position according to the indicators 34 as guides. After that, similar to the first embodiment, the step of separating and the step of incising are repeated in accordance with the size of the diseased part X. Therefore, the submucosal layer W including the diseased part X is removed from the alimentary tract.

According to the mucosa separation apparatus and the method for mucosa separation of this embodiment, since there is no need to provide the plate member 15 to the balloon insertion portion 10 like the separation balloon insertion device 5 of the first embodiment, it is possible to slightly adjust the balloon insertion portion 10 in the curving direction thereof easily and reliably.

Note that, in the first embodiment, only the top end 10b of the balloon insertion portion 10 is inserted into the aperture H, and thereafter the curving angle of the head portion 10c of the balloon insertion portion 10 is adjusted. However, as the second embodiment, it may be arranged such that the head portion 10c of the balloon insertion portion 10 be inserted into the submucosal layer W after the curving angle of the head portion 10c of the balloon insertion portion 10 is adjusted.

In the above mentioned embodiment, the channel 11 is used as a supply passage for supplying the fluid to the balloon 12, and is used as a passage for inserting the operation wire 13. However, it may be arranged such that the supply passage for supplying the fluid be provided to the balloon insertion portion 10 separately from the passage for inserting the operation wire 13.

In the first and second embodiments, a number of the communication holes 22 which perform as the first flexible portion 9 are formed in the head portion 10c of the balloon insertion portion 10. However, it may be arranged such that a single communication hole 22 be formed in the head portion 10c, and the first flexible portion be provided to the head portion 10c separately from the single communication hole 22. For example, an accordion portion which performs as the first flexible portion may be formed in the head portion 10c of the balloon insertion portion 10. Further, it may be arranged such that two operation wires 13 be provided to the balloon insertion portion 10, and the head portion 10c of the balloon insertion portion 10 be curved in two directions mutually-perpendicular (vertical direction and horizontal direction).

Figure 30:
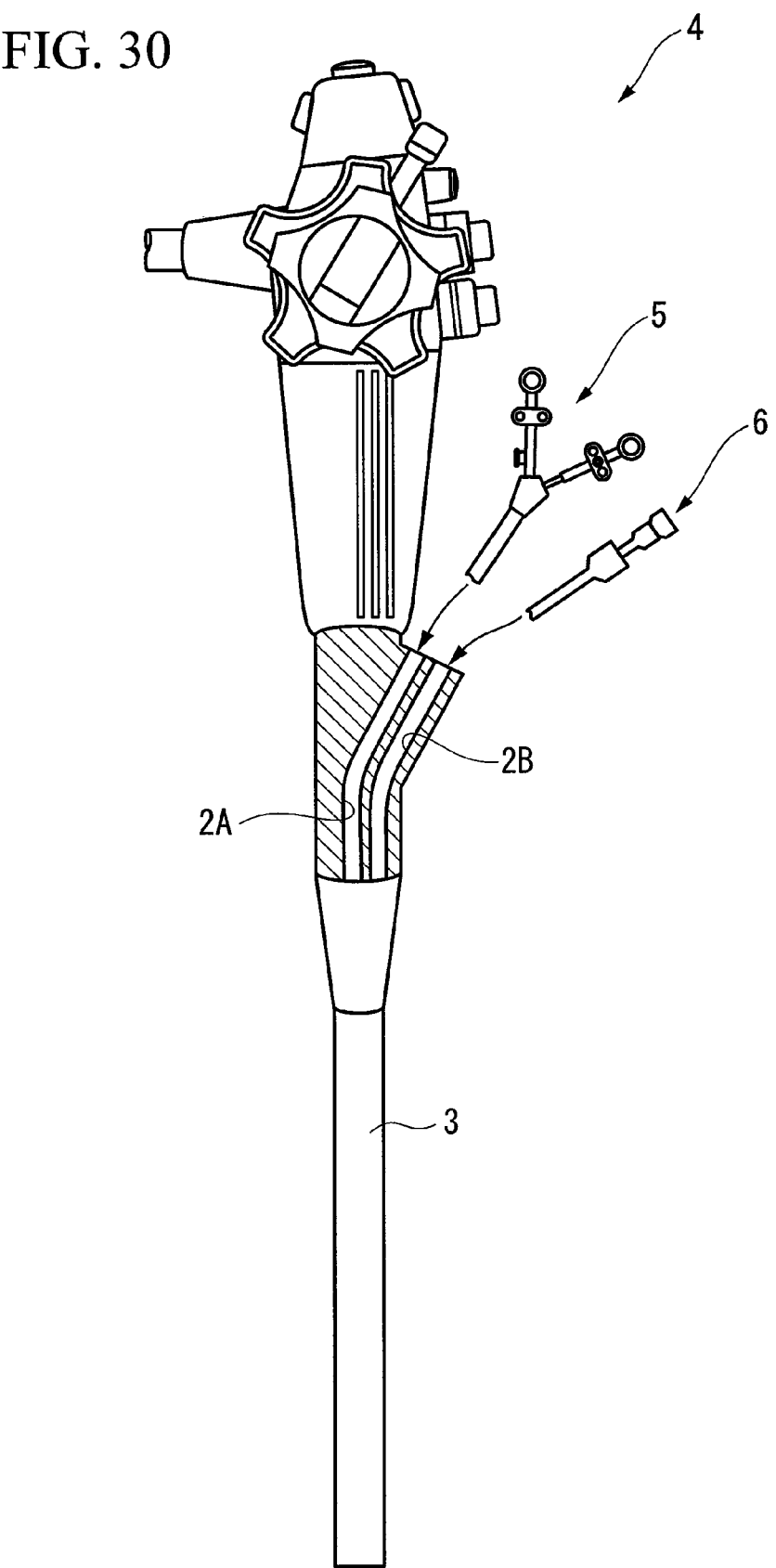
FIG. 30 is a schematic view showing a modification of the mucosa separation system including the mucosa separation apparatus of the present invention.

In the first embodiment, the separation balloon insertion device 5 is applied to the endoscope having the single channel 2. However, as shown in FIG. 30, it may be arranged such that two channels 2A and 2B be formed in the insertion portion 3 of the endoscope 4, the separation balloon insertion device 5 of the first embodiment be inserted into the channel 2A, and the submucosal local injection needle 6 be inserted into the channel 2B. Therefore, since the separation balloon insertion device 5 is inserted inside the alimentary tract together with the submucosal local injection needle 6, it is possible to quickly transfer from the step of inflating the diseased part X to the step of separating without replacing instruments. As a result, it is possible to shorten the operation time which goes from the step of inflating of the diseased part X to the step of separation of the submucosal layer W.

It may be arranged such that grasping forceps be inserted into the channel 2B instead of the submucosal local injection needle 6. In this case, since the separation balloon insertion device 5 is inserted inside the alimentary tract through the channel 2B together with the submucosal local injection needle 6, it is possible to separate the mucosa from the submucosal layer while the diseased part X is grasped by the grasping forceps. Therefore, it is possible to exactly insert the balloon 12 into the submucosal layer W without interference by the diseased part X separated, and it is possible to separate the diseased part X from the submucosal layer W while tightly grasping the diseased part X. As a result, it is possible to exactly perform the procedure.

Next, a third embodiment of a mucosa separation apparatus and a method for mucosa separation of the present invention will be explained with reference to FIG. 31 through FIG. 53. Note that, the same descriptive symbols are used for component elements that are the same as those used in the first embodiment and a description thereof is omitted.

Figure 31:
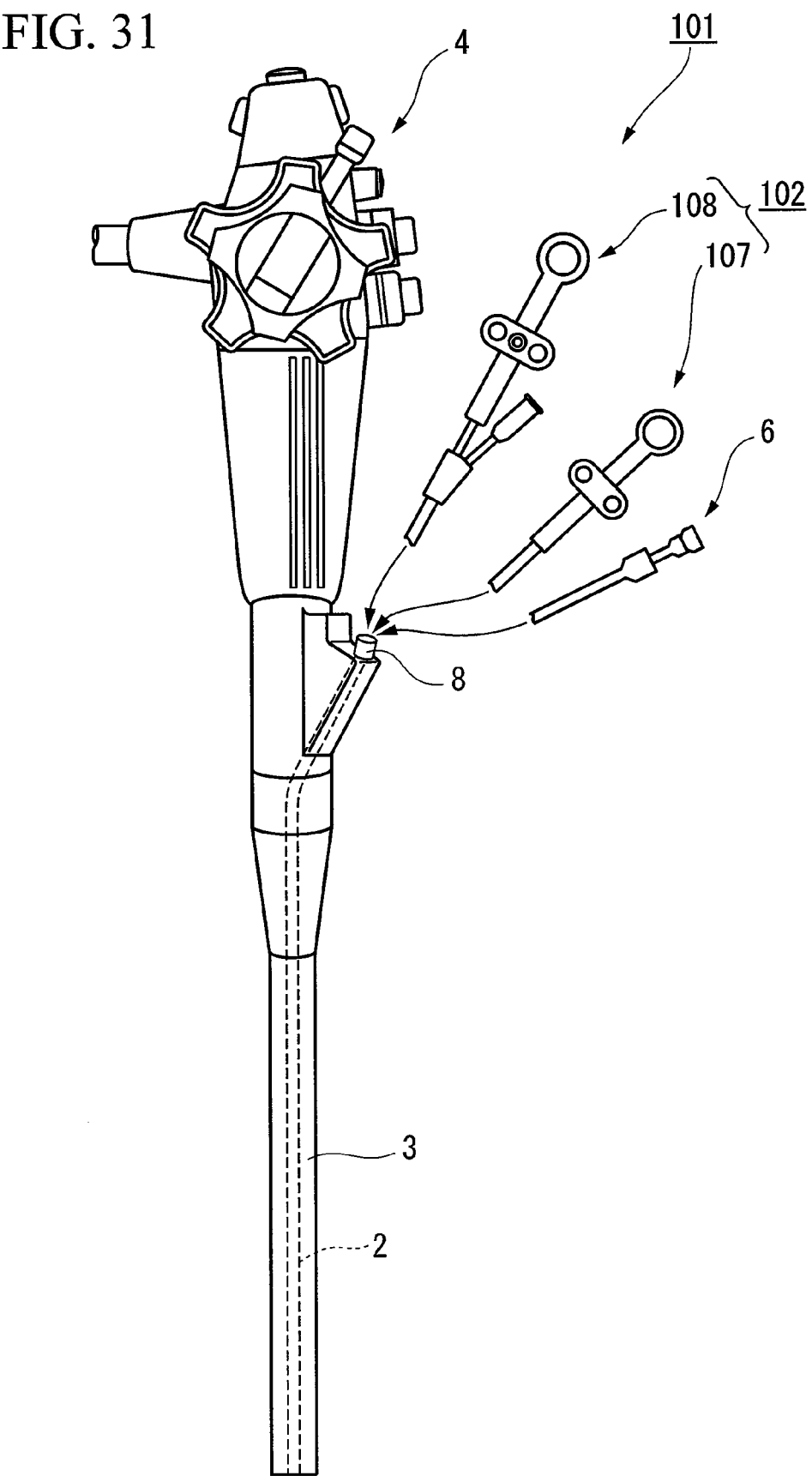
FIG. 31 is a view showing a mucosa separation apparatus of a third embodiment of the present invention, and shows a schematic view of a mucosa separation system including the endoscope, a support device, the separation balloon insertion device, and the submucosal local injection needle.

As shown in FIG. 31, a mucosa separation system 101 of this embodiment includes the endoscope 4, a mucosa separation instrument (mucosa separation apparatus) 102, and the submucosal local injection needle 6. The mucosa separation instrument 102 locally separates the submucosal layer from the muscularis propria, and removes the diseased part of the alimentary tract. The mucosa separation instrument 102 is composed of a support device 107 and a separation balloon insertion device 108. One of the group of the support device 107, the separation balloon insertion device 108 and the submucosal local injection needle 6 is inserted into the channel 2 formed in the insertion portion 3 of the endoscope 4 through the sleeve 8 as appropriate.

Figure 32:
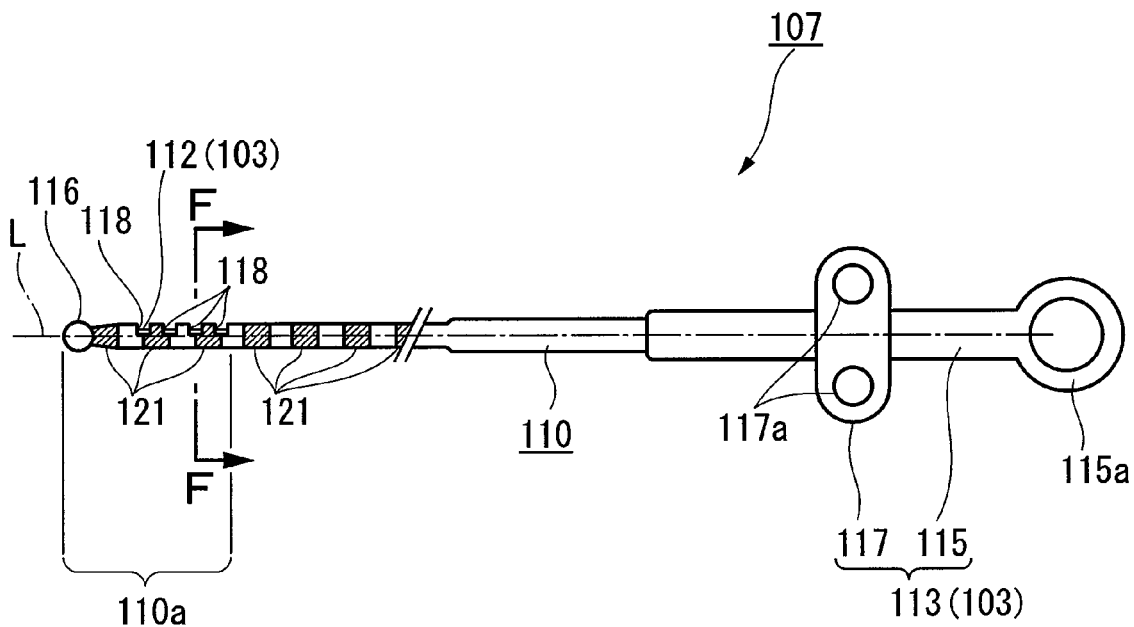
FIG. 32 is a plan view showing the support device of the third embodiment.

The support device 107 pierces the submucosal layer to form an insertion route into which the separation balloon insertion device 108 is inserted. As shown in FIG. 32, the support device 107 includes a support device insertion portion (second insertion portion) 110 which is flexible and a curving mechanism (curving portion) 103 which makes a head portion 110a of the support device insertion portion 110 curve.

Figure 33:
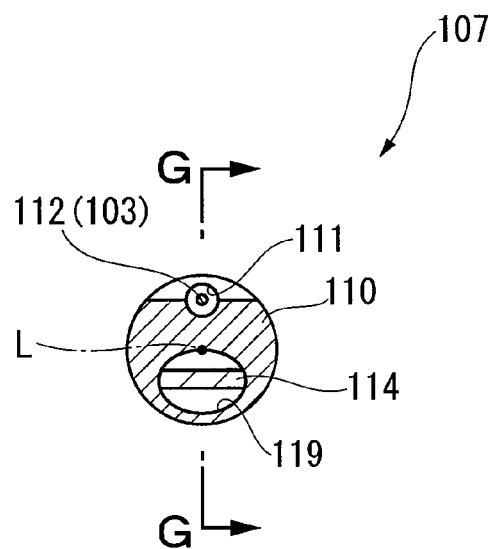
FIG. 33 is a sectional view taken along a line F-F in FIG. 32.

The support device insertion portion 110 has a long tubular body, and a channel 111 is formed within the support device insertion portion 110 from the terminal of the support device insertion portion 110 to the tip thereof. As shown in FIG. 33, the channel 111 is formed at a position which slightly separates from the axis L of the support device insertion portion 110.

Figure 34:
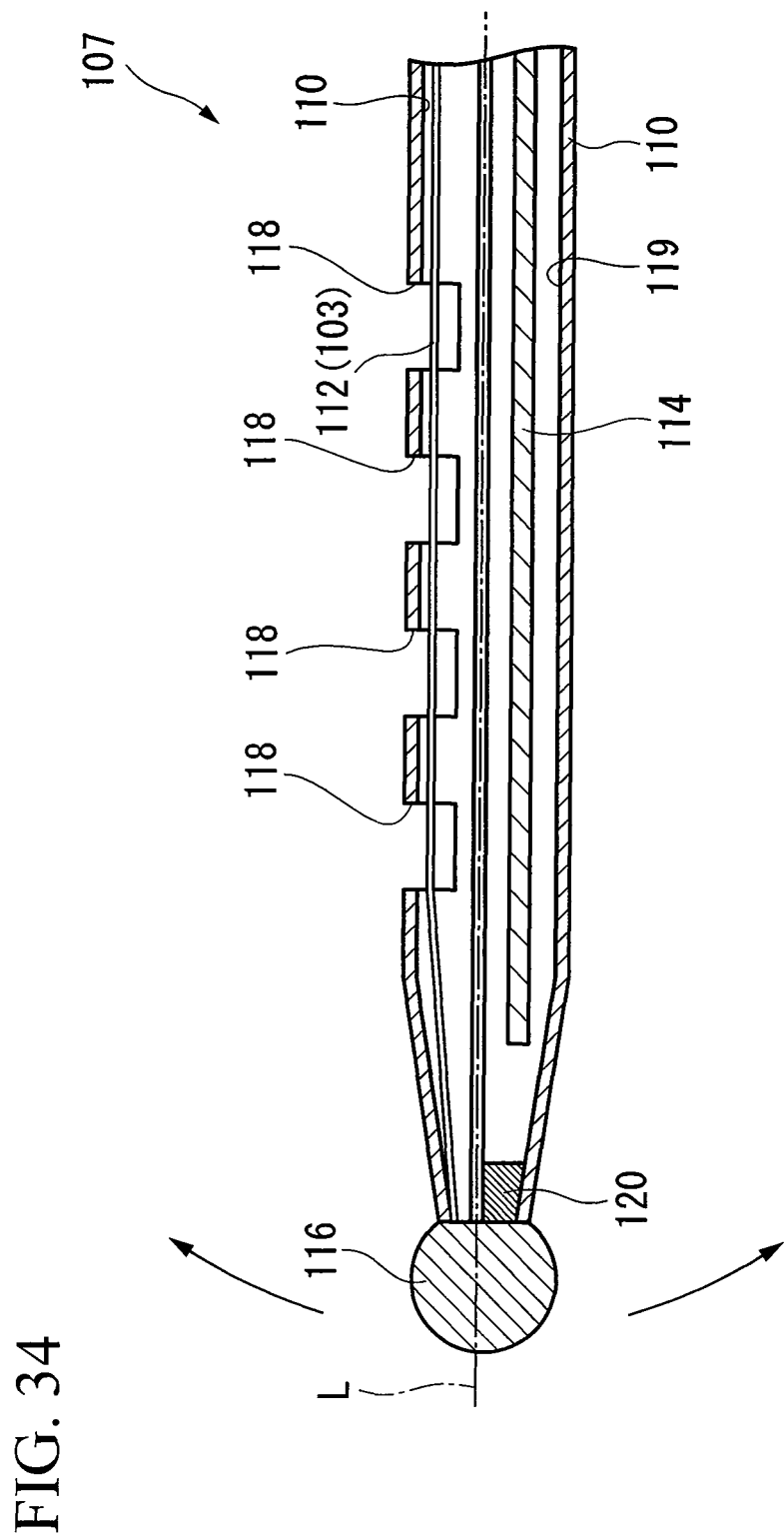
FIG. 34 is a sectional view taken along a line G-G in FIG. 33.

As shown in FIG. 32 through FIG. 34, the curving mechanism 103 includes an operation wire 112 and an operation section 113. The operation wire 112 is inserted into the channel 111. The operation section 113 is disposed on the base portion of the support device insertion portion 110.

As shown in FIG. 33, a plate member (second curving support member) 114 is disposed inside the head portion 110a of the support device insertion portion 110 along the longitudinal direction thereof. The plate member 114 has the sectional characteristic to incline to be flexible in a particular direction.

An operation section main body 115 of the operation section 113 is connected to the base portion of the support device insertion portion 110. A spherical shape portion 116 is attached to the tip of the support device insertion portion 110. One end of the operation wire 112 is connected to the spherical shape portion 116 attached to the tip of the support device insertion portion 110.

As shown in FIG. 34, a number of communication holes 118 which communicate with the channel 111 are formed in a part of the support device insertion portion 110 which is closer to the base portion of the support device insertion portion 110 than the spherical shape portion 116. The communication holes 118 are arranged in line along the longitudinal direction of the support device insertion portion 110.

As shown in FIG. 32, the operation section 113 includes an operation section main body 115, and a sliding portion 117 which is slidable with respect to the operation section main body 115. The other end of the operation wire 112 inserted into the channel 111 is connected to the sliding portion 117. When the operation section 113 is operated, in other words, when the sliding portion 117 is slid forward or backward with respect to the operation section main body 115, the head portion 110a of the support device insertion portion 110 is curved with respect to the part of the support device insertion portion 110 which is closer to the base portion thereof than the head portion 110a. Particular explanation thereof will be given below.

As shown in FIG. 32, a finger hanging ring 115a on which a thumb of an operator can be hanged is attached to the terminal of the operation section main body 115. Two finger hanging holes 117a on which a forefinger and a middle finger of the operator can be respectively hanged are formed in the sliding portion 117. The operator hangs the thumb of one hand on the finger hanging ring 115a, and hangs each of the forefinger and the middle finger of the one hand on the finger hanging holes 117a of the sliding portion 117. Thereby, he/she can easily operate the curving operation of the support device insertion portion 110 using only his one hand.

Since the communication holes 118 are formed in a part of the head portion 110a of the support device insertion portion 110, the part is more flexible than the other part of the head portion 110a. When a predetermined strength force acts on the area in which the communication holes 118 are formed, the area performs as a second flexible portion 105 which is curved before curving of the other area. Therefore, when the operation section 113 is operated, the head portion 110a of the support device insertion portion 110 is easily curved centering around the area in which the communication holes 118 are formed. That is, when the sliding portion 117 is pulled toward the terminal of the operation section main body 115, the head portion 110a of the support device insertion portion 110 is curved so as to turn up a surface of the part on which the communication holes 118 are formed. When the sliding portion 117 is pushed toward the tip of the operation section main body 115, the head portion 110a of the support device insertion portion 110 is curved so as to turn up an opposite surface of the surface of the part on which the communication holes 118 are formed.

The plate member 114 is made of an elastic material such as metal or plastic. As shown in FIG. 33 and FIG. 34, the plate member 114 is formed like a narrow strip piece. The plate member 114 has the sectional characteristic to incline to be flexible in the thickness direction thereof, and is disposed on the opposite side of the channel 111 across the axis L so that the thickness direction of the plate member 114 conforms to a direction being from the operation wire 112 to the axis L. In other words, a direction in which the plate member 114 inclines to curve conforms to a direction in which the head portion 110a of the support device insertion portion 110 must be curved. Therefore, the head portion 110a of the support device insertion portion 110 inclines to curve in the thickness direction of the plate member 114, and inclines to hardly curve in the width direction of the plate member 114.

A channel 119 for inserting the plate member 114 thereinto is formed within the support device insertion portion 110. The plate member 114 is inserted into the channel 119 from the tip of the support device insertion portion 110, and is held inside the channel 119 depending on the frictional force between the plate member 114 and an inside wall surface of the channel 119. A sealing member 120 which seals the channel 119 is disposed within the top end of the support device insertion portion 110.

Figure 35:
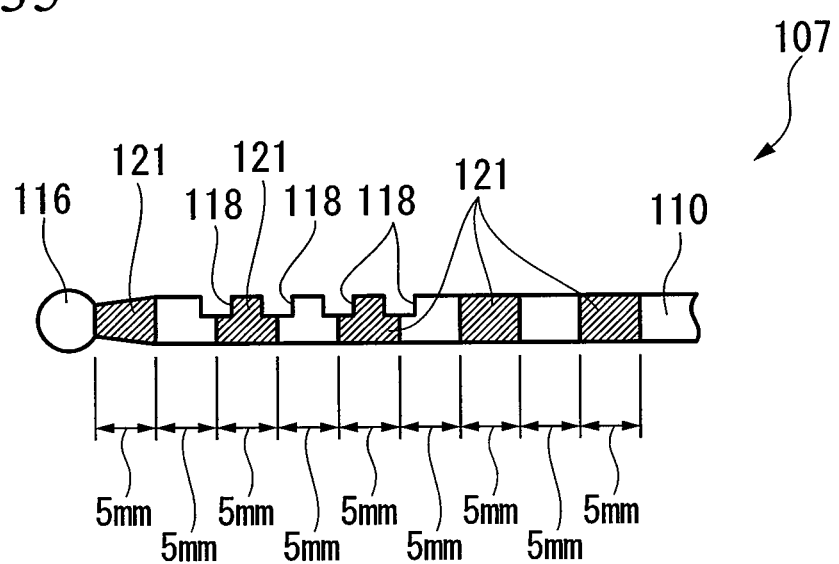
FIG. 35 is a plan view showing indicators provided on an insertion portion of the support device of the third embodiment.
Figure 36:
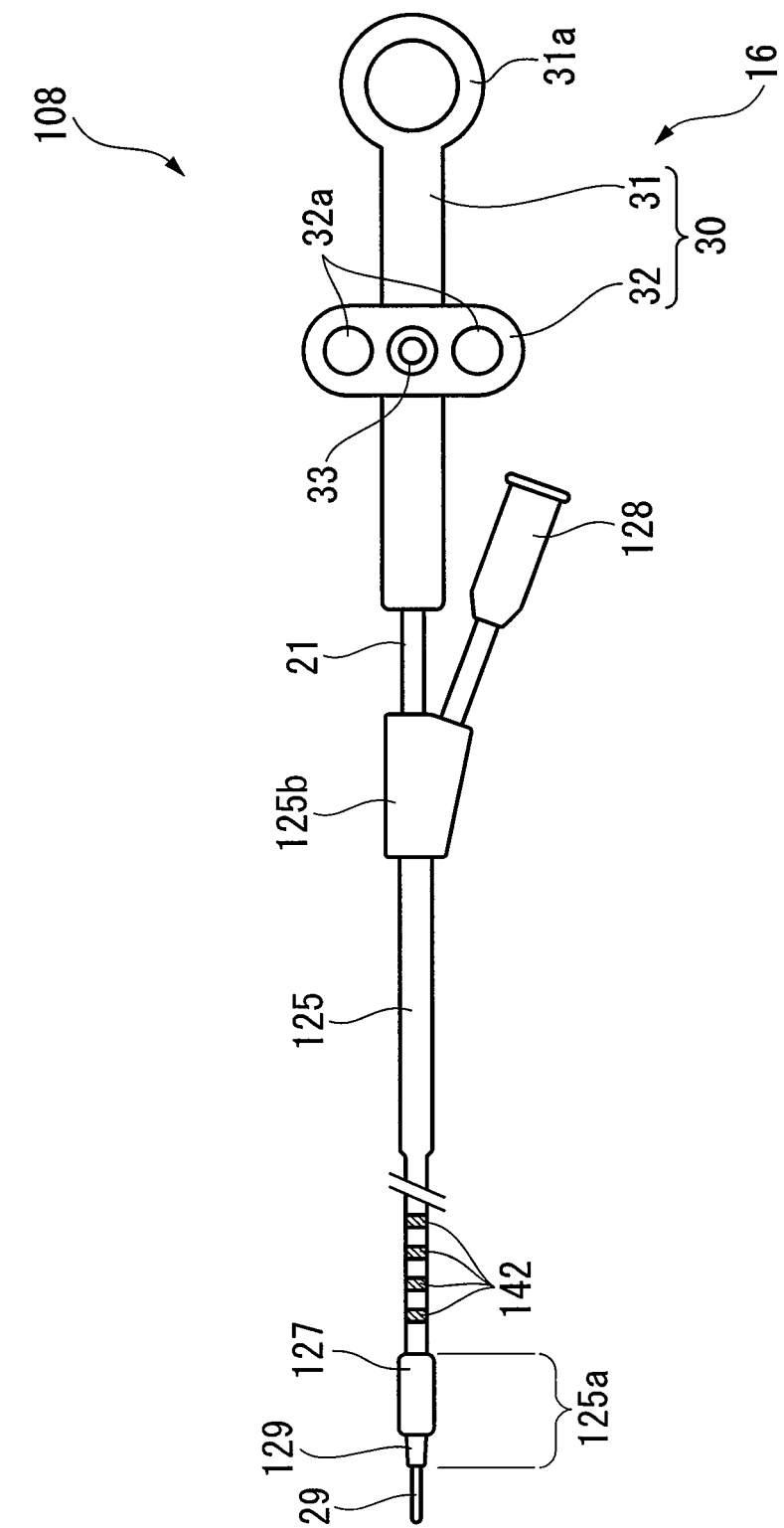
FIG. 36 is a plan view showing the separation balloon insertion device of the third embodiment.

As shown in FIG. 35, indicators 121 which indicate the insertion quantity of the head portion 110a of the support device insertion portion 110 into the mucosa, are disposed on an area of the support device insertion portion 110 which is closer to the base portion thereof than the spherical shape portion 116. The indicators 121 are located every 5 millimeters from the spherical shape portion 116 toward the terminal end of the support device insertion portion 110.

The separation balloon insertion device 108 locally separates the submucosal layer from a muscularis propria, and removes a diseased part of the alimentary tract. As shown in FIG. 36 through FIG. 39, the separation balloon insertion device 108 includes a balloon insertion portion (first insertion portion) 125 which is flexible and a balloon (expansion portion) 127 disposed on a head portion of the balloon insertion portion 125.

The balloon insertion portion 125 has a long tubular body, and a passage 126 is formed within the balloon insertion portion 125 from the terminal of the balloon insertion portion 125 to the tip thereof. The balloon 127 expands by infusion of a fluid such as gas or liquid through the passage 126.

A channel 136 for inserting the high-frequency knife 16 thereinto is formed within the balloon insertion portion 10 along the passage 126.

A connecting portion 125b is disposed on the base portion of the balloon insertion portion 125. The operation tube 21 of the high-frequency knife 16 and a fill port 128 which communicates with the passage 126 are disposed on the connection portion 125b. A syringe (not shown) performing as a fluid supply source which supplies the fluid for expanding the balloon 127 is connected to the fill port 128. A top end 129 of the balloon insertion portion 125 is formed like a tapered shape so as the diameter thereof gradually reduces toward the top end.

Figure 37:
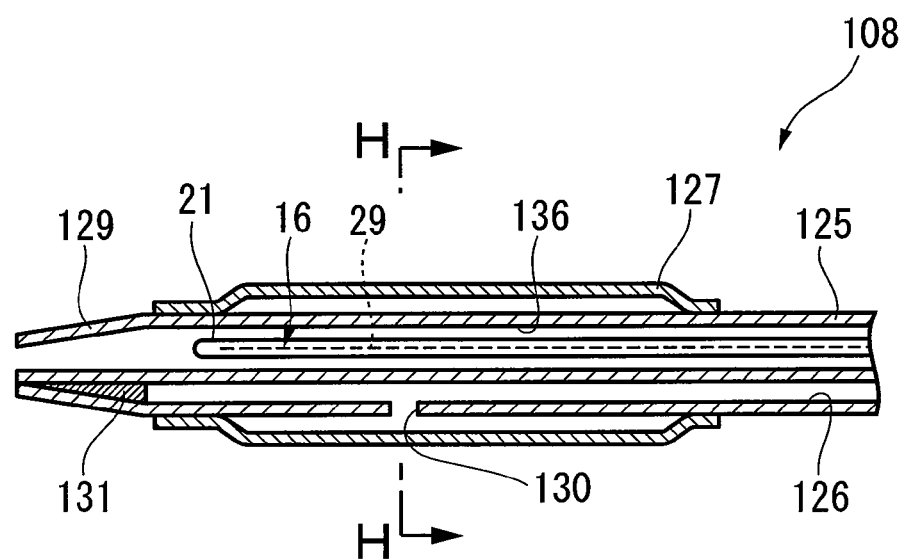
FIG. 37 is a sectional view showing a head portion of the separation balloon insertion device of the third embodiment.
Figure 38:
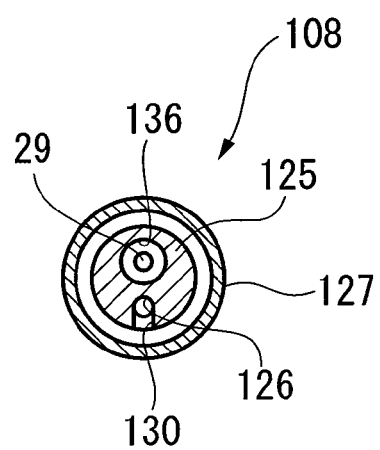
FIG. 38 is a sectional view taken along a line H-H in FIG. 38.

As shown in FIG. 37 and FIG. 38, the balloon 127 is disposed on a part of the balloon insertion portion 125 which is closer to the base portion of the balloon insertion portion 125 than the top end 129 so as to cover around the balloon insertion portion 125. A communication hole 130 which communicates the passage 126 with the inside space of the balloon 127 are formed in the balloon insertion portion 125 covered by the balloon 127. A sealing member 131 which seals the passage 126 is disposed inside the top end 129. Therefore, the fluid which has been supplied into the passage 126 is flowed to the balloon 127 through the communication hole 130 without leakage from the tip of the passage 126.

As shown in FIG. 37, one end of the operation tube 21 of the high-frequency knife 16 is inserted into the channel 136 until the one end of the operation tube 21 approaches the vicinity of the top end 129 of the balloon insertion portion 125. The other end of the operation tube 21 is protruded from the connection portion 125b. The operator hangs the thumb of one hand on the finger hanging ring 31a, and hangs each of the forefinger and the middle finger of the one hand on the finger hanging holes 32a of the knife sliding portion 32.

Figure 39:
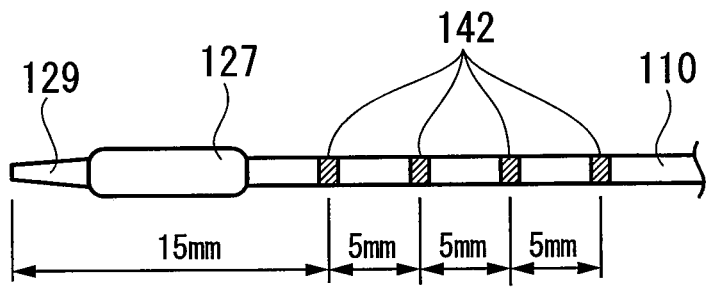
FIG. 39 is a plan view showing indicators provided on an insertion portion of the separation balloon insertion device of the third embodiment.

As shown in FIG. 39, indicators 142 which indicate the insertion quantity of the head portion 125a of the balloon insertion portion 125 into the mucosa are disposed on an area of the balloon insertion portion 125 which is closer to the base portion thereof than the balloon 127. The indicators 142 are located every 5 millimeters from a point being separate from the top end 129 by 15 millimeters toward the terminal end of the balloon insertion portion 125.

The method for mucosa separation for removing a diseased part X developing inside an alimentary tract from a submucosal layer W using the mucosa separation system 101 as mentioned above will be explained.

The method for mucosa separation of this embodiment includes the steps of inflating, aperture-forming, inserting, angle-adjusting, sticking, length-adjusting, separating and incising. Each of the steps will be explained.

Figure 40:
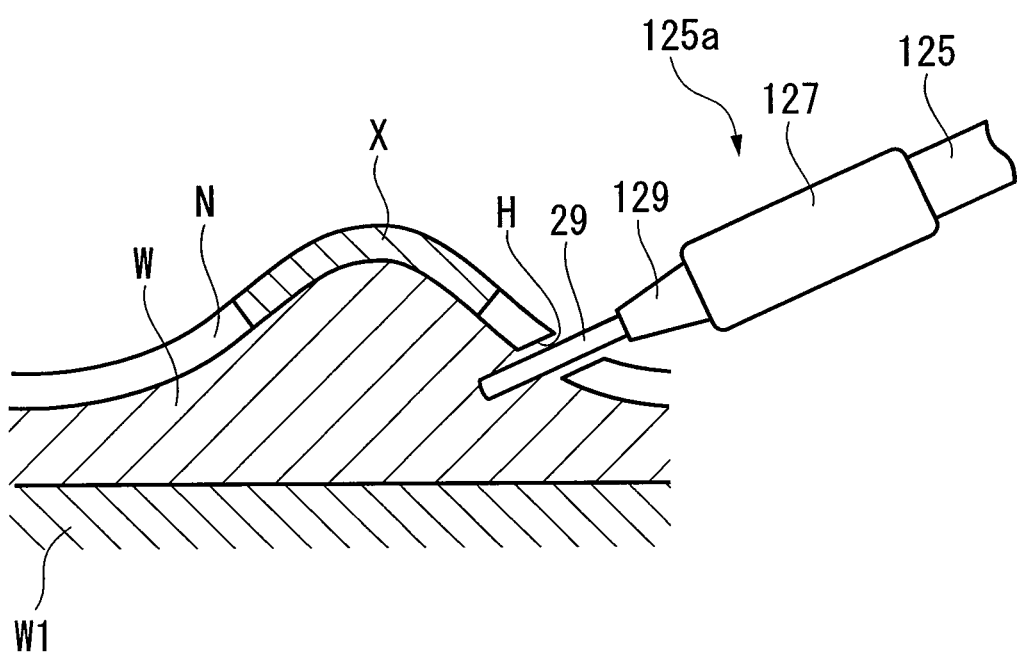
FIG. 40 is a view showing a method for mucosa separation of the third embodiment of the present invention, and shows a state where an aperture is formed in the inflated mucosa using the high-frequency knife after inflating the submucosal layer around the diseased part.

First, similar to the first embodiment, the step of inflating is performed (refer to FIG. 9). After that, the step of aperture-forming is performed. That is, the balloon insertion portion 125 of the separation balloon insertion device 108 is inserted into the channel 2, and then the head portion 125a of the balloon insertion portion 125 is protruded from the tip of the insertion portion 3. Next, the knife sliding portion 32 is moved toward the tip of the balloon insertion portion 125, and thereby the knife portion 29 is protruded from the operation tube 21, and the knife portion 29 is further protruded from the top end 129 of the balloon insertion portion 125. While the condition is held, high-frequency current is supplied to the knife portion 29 from the high-frequency power supply connected to the power supply connection portion 33. As shown in FIG. 40, the knife portion 29 is moved forward, and thereby an aperture H with a predetermined size is formed in a mucosa N in the vicinity of the diseased part X.

After the aperture H is formed, supplying of high-frequency current is stopped. The sliding portion 25 is moved toward the tip of the balloon insertion portion 125, and thereby the knife portion 29 is retracted into the operation tube 21.

After the step of aperture-forming, the step of inserting is performed. That is, the balloon insertion portion 125 is pulled out from the channel 2. Then, the support device insertion portion 110 of the support device 107 is inserted into the channel 2 instead of the balloon insertion portion 125, and the head portion 110a of the support device insertion portion 110 is protruded from the tip of the insertion portion 3. Since the plate member 14 is disposed inside the head portion 110a of the support device insertion portion 110, the head portion 110a of the support device insertion portion 110 is moved in accordance with a curving angle of the insertion portion 3 while the head portion 110a moves through the channel 2. When the head portion 110a of the support device insertion portion 110 is protruded from the tip of the insertion portion 3, the curving direction of the insertion portion 3 (vertical direction) conforms to the thickness direction of the plate member 114. The thickness direction of the plate member 114, that is a direction in which the plate member 114 inclines to curve conforms to the curving direction of the support device insertion portion 110. Therefore, just the support device insertion portion 110 is inserted into the channel 2, and thereby the curving direction of the head portion 110a of the support device insertion portion 110 conforms to the curving direction of the insertion portion 3.

Note that, in this embodiment, it is assumed that the area of the support device insertion portion 110 in which the operation wire 112 and the communication holes 118 are formed is positioned at an upper portion of the insertion portion 3.

Figure 41:
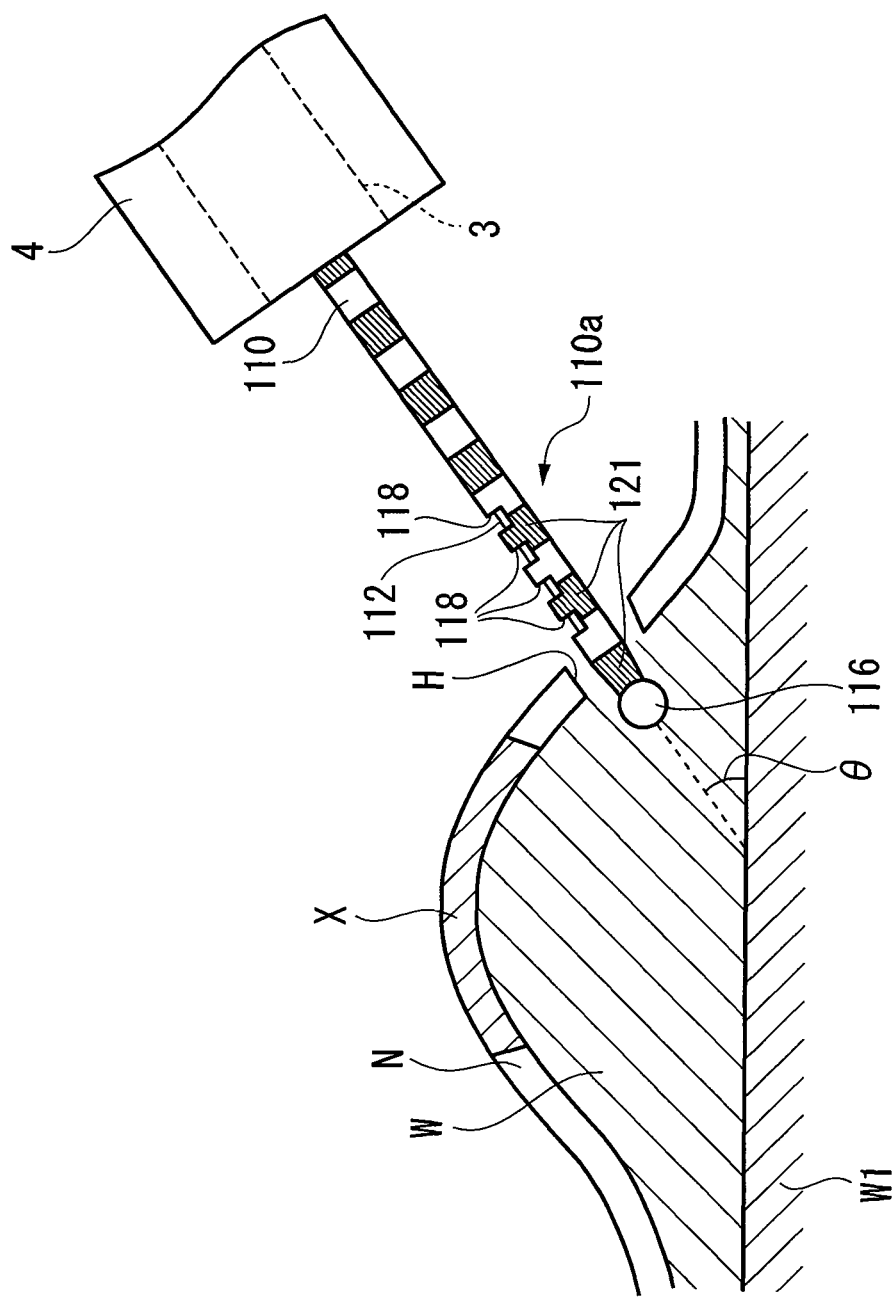
FIG. 41 is a view showing a method for mucosa separation of the third embodiment of the present invention, and shows a state where the tip of the support device insertion portion is inserted into the aperture after forming the aperture in the mucosa.

As shown in FIG. 41, only the spherical shape portion 116 disposed on the tip of the support device insertion portion 110 is inserted into the aperture H. Note that, at this stage, the head portion 110a of the support device insertion portion 110 is across a surface of the alimentary tract by an angle θ.

Figure 42:
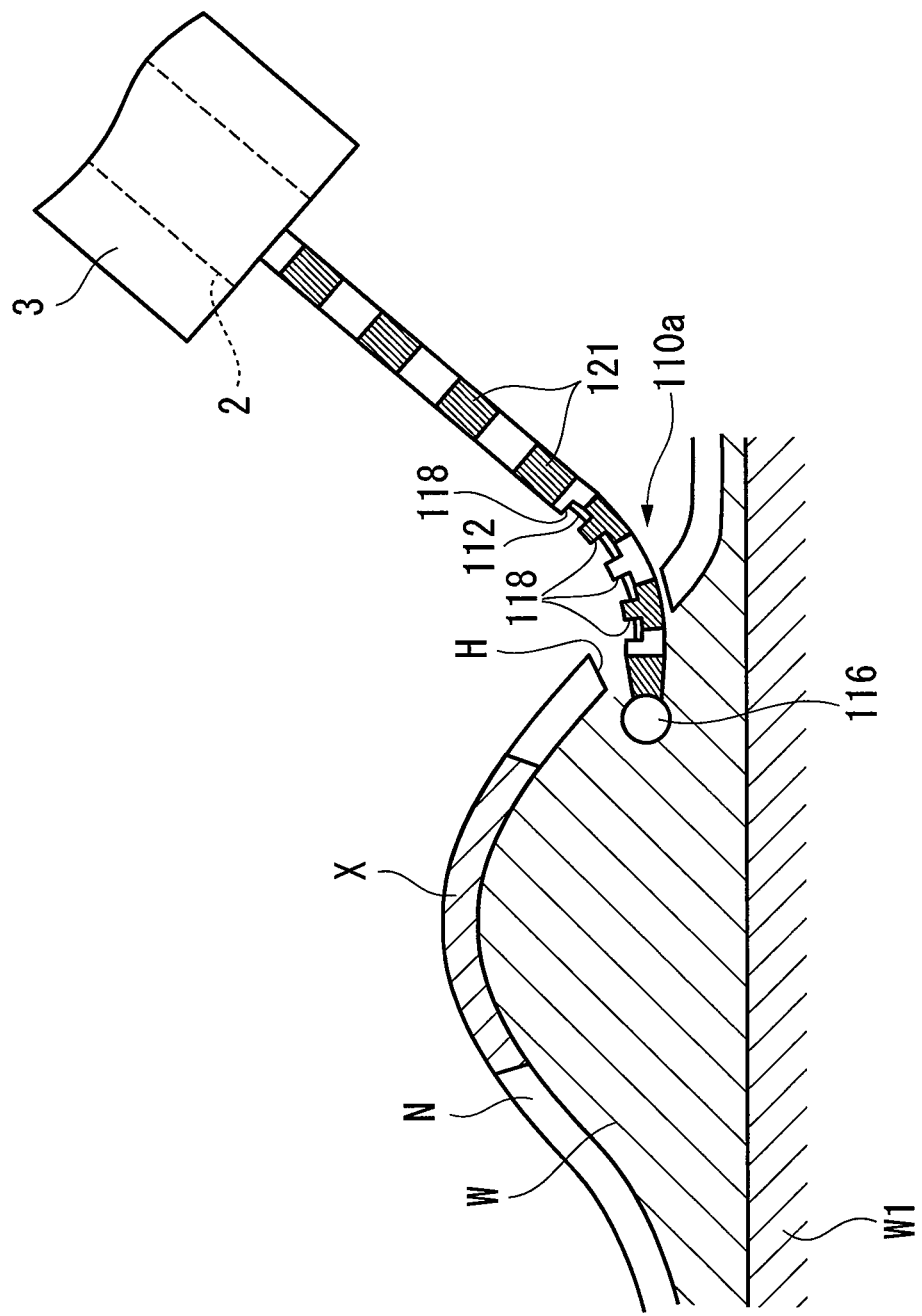
FIG. 42 is a view showing a method for mucosa separation of the third embodiment of the present invention, and shows a state where the head portion of the support device insertion portion is curved after inserting the tip of the support device insertion portion into the aperture.

After the step of inserting, the step of angle-adjusting is performed. That is, the sliding portion 117 is moved toward the terminal of the support device insertion portion 110 with respect to the operation section main body 115, and thereby the operation wire 112 is pulled. Since the one end of the operation wire 112 is connected to the head portion 110a of the support device insertion portion 110 through the spherical shape portion 116, a pull force generated on the operation wire 112 by the pulling operation carries to the head portion 110a of the support device insertion portion 110. Therefore, a compression force acts on a substantially half part of the support device insertion portion 110 inside which the operation wire 112 is disposed. In contrast, a pull force acts on a substantially half part of the support device insertion portion 110 positioned on the opposite side of the operation wire 112 across the axis L. As a result, as shown in FIG. 42, the support device insertion portion 110 is curved so that the half part of the support device insertion portion 110 in which the operation wire 112 and the communication holes 22 are formed warps upward of the insertion portion 3. Particularly, the support device insertion portion 110 is curved centering around the second flexible portion 105. As a result, the head portion 110a of the support device insertion portion 110 warps upward of the insertion portion 3.

Otherwise, the sliding portion 117 is moved toward the tip of the support device insertion portion 110 with respect to the support device insertion portion 110, and thereby the operation wire 112 is pushed into the channel 111. A pushing force generated on the operation wire 112 by the pushing operation carries to the head portion 110a of the support device insertion portion 110. Therefore, a pull force acts on the substantially half part of the support device insertion portion 110 inside which the operation wire 112 is disposed. In contrast, a compression force acts on the substantially half part of the support device insertion portion 110 positioned on opposite side of the operation wire 112 across the axis L. As a result, the head portion 110a of the support device insertion portion 110 warps downward of the insertion portion 3.

By performing the pulling and pushing operation, the head portion 110a of the support device insertion portion 110 is curved so that the head portion 110a of the support device insertion portion 110 becomes to be substantially parallel to the surface of the alimentary tract.

Figure 43:
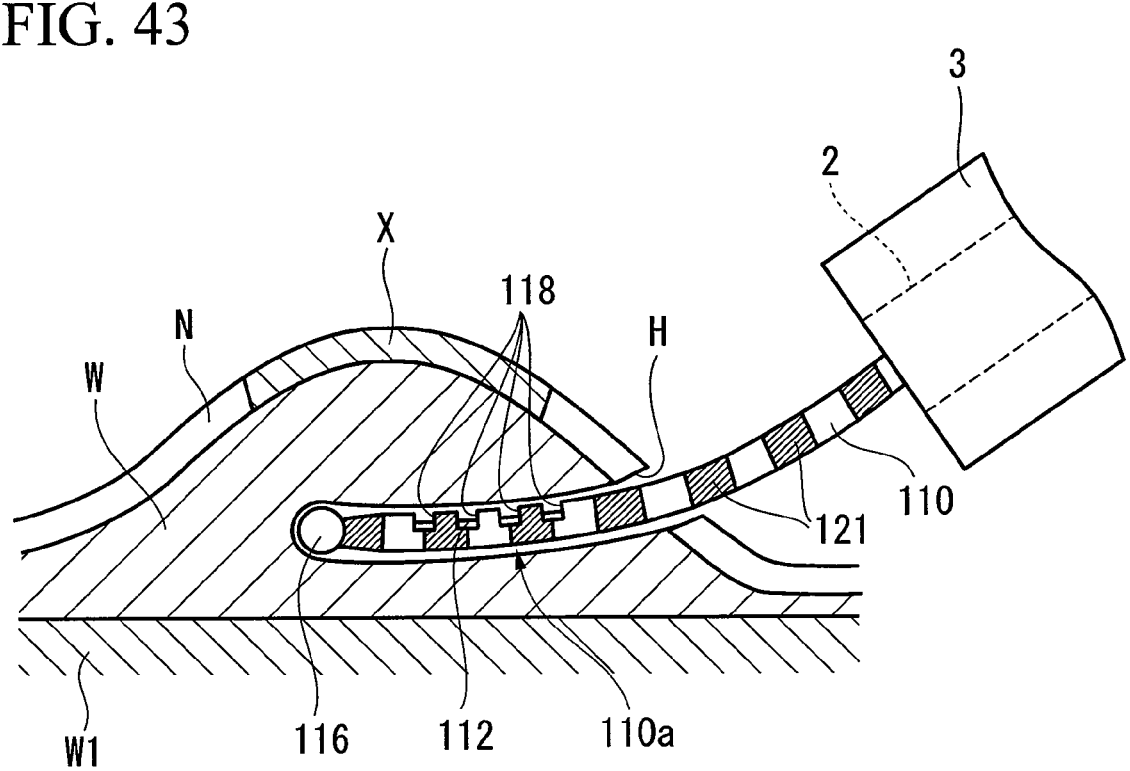
FIG. 43 is a view showing a method for mucosa separation of the third embodiment of the present invention, and shows a state where the support device insertion portion pierces the submucosal layer after curving the head portion of the support device insertion portion.
Figure 44:
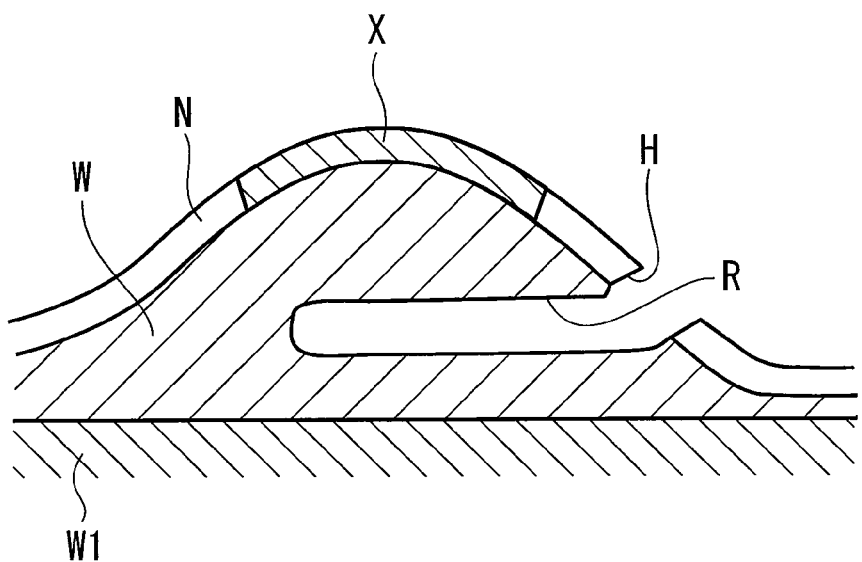
FIG. 44 is a view showing a method for mucosa separation of the third embodiment of the present invention, and shows a state where the support device insertion portion has been retracted from the submucosal layer.

After the step of angle-adjusting, the step of sticking is performed. That is, as shown in FIG. 43, the support device insertion portion 110 is moved along a direction being parallel to the surface of the alimentary tract, and thereby the head portion 110a of the support device insertion portion 110 is pushed into the submucosal layer W through the aperture H according to the indicators 34 as guides. Therefore, as shown in FIG. 44, an insertion route R which has a predetermined internal diameter in accordance with a external diameter of the support device insertion portion 110 is formed in the submucosal layer W so that the insertion route R is parallel to the surface of the alimentary tract.

Figure 45:
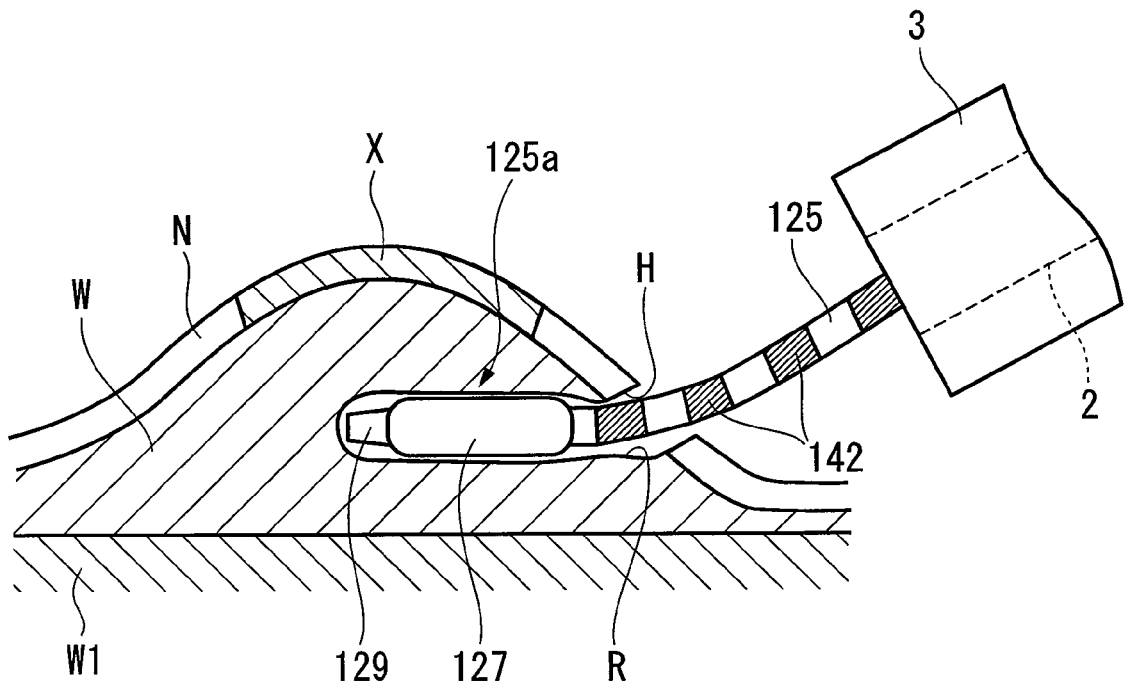
FIG. 45 is a view showing a method for mucosa separation of the third embodiment of the present invention, and shows a state where the balloon insertion portion is inserted into the submucosal layer along an insertion route.
Figure 46:
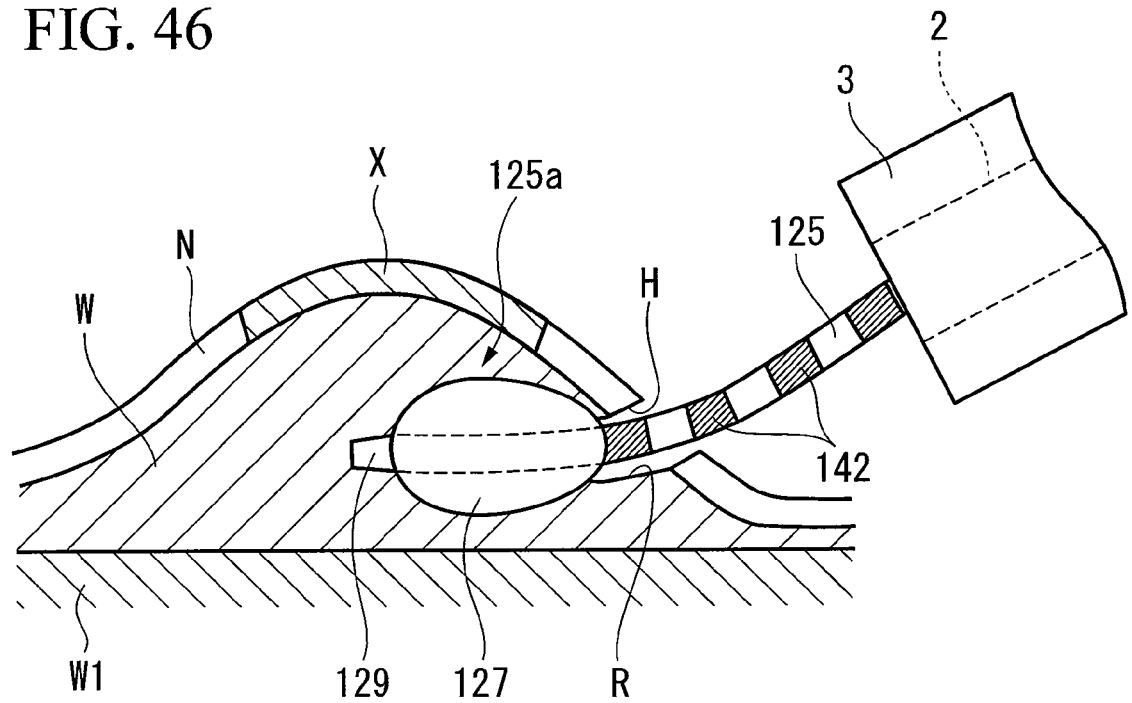
FIG. 46 is a view showing a method for mucosa separation of the third embodiment of the present invention, and shows a state where the balloon is expanded within the submucosal layer after inserting the balloon insertion portion into the submucosal layer.

After the step of sticking, the step of length-adjusting is performed. That is, the support device insertion portion 110 is pulled out from the channel 2. Then, the balloon insertion portion 125 of the separation balloon insertion device 108 is inserted into the channel 2 again, and the head portion 125a of the balloon insertion portion 125 is protruded from the tip of the insertion portion 3. As shown in FIG. 45, the balloon insertion portion 125 is moved along the direction being parallel to the surface of the alimentary tract, and thereby the head portion 125 of the balloon insertion portion 125 is pushed into the submucosal layer W along the insertion route R, and then the head portion 125a is positioned at a predetermined position according to indicators 142 as guides.

Figure 47:
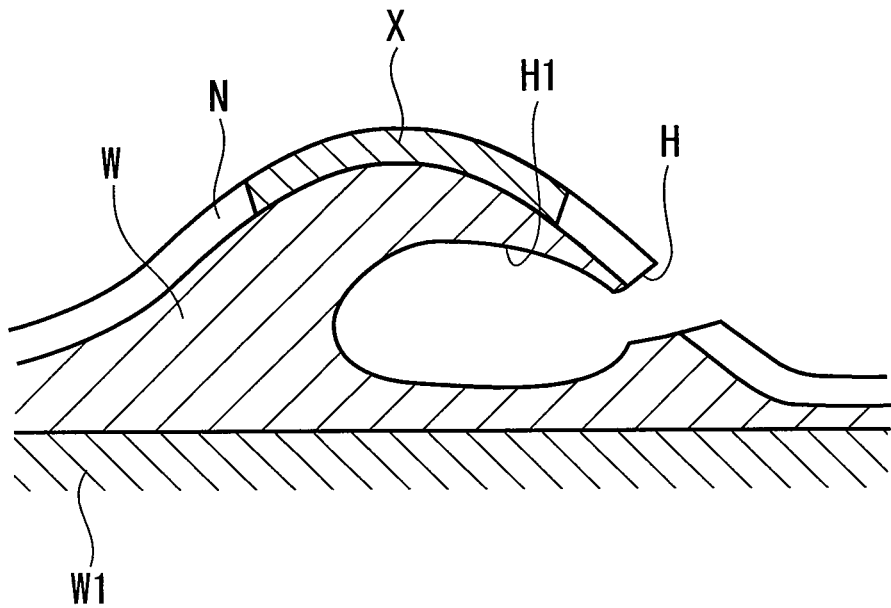
FIG. 47 is a view showing a method for mucosa separation of the third embodiment of the present invention, and shows a state where the balloon insertion portion has been retracted from the submucosal layer with the contracted balloon after expanding the balloon within the submucosal layer.

After the step of length-adjusting, the step of separating is performed. That is, fluid is supplied into the passage 126 through the fill port 128 using a syringe (not shown). The fluid supplied into the passage 126 is supplied to the balloon 127 through the communication hole 130, and thereby the balloon 127 is inflated (shown in FIG. 46). Therefore, a part of the submucosal layer W is separated from the muscularis propria W1 existing under the submucosal layer W. Then, the fluid is discharged from the balloon 127 through the fill port 128, and thereby the balloon 127 deflates to its original shape. As a result, as shown in FIG. 47, a cavity H1 is formed between the muscularis propria W1 and the submucosal layer W separated from the muscularis propria W1.

Figure 48:
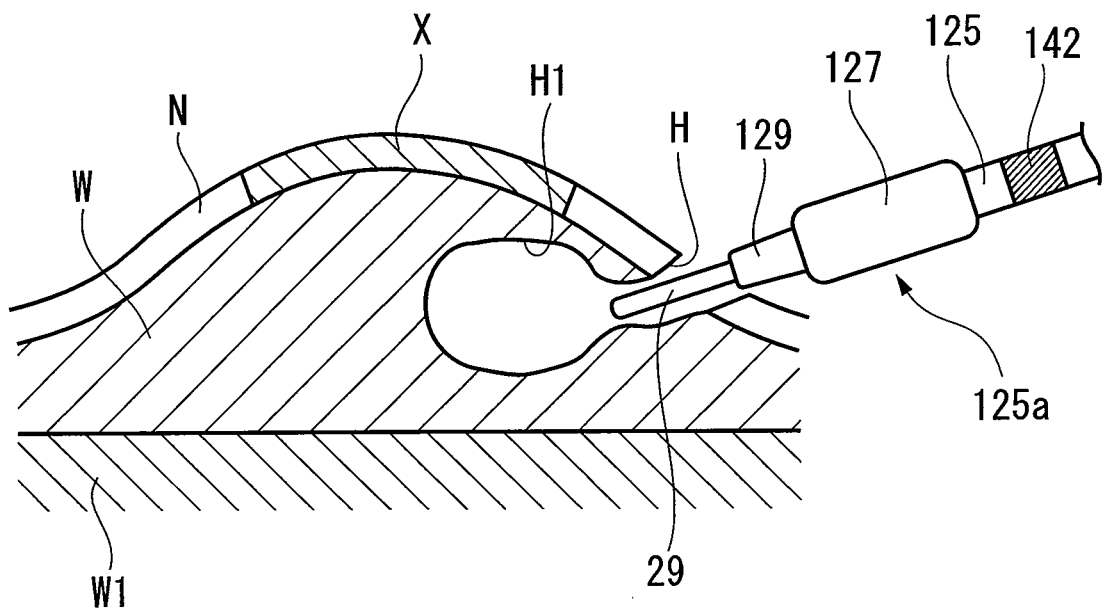
FIG. 48 is a view showing a method for mucosa separation of the third embodiment of the present invention, and shows a state where the high-frequency knife is inserted into the aperture after retracting the balloon insertion portion from the submucosal layer.
Figure 49:
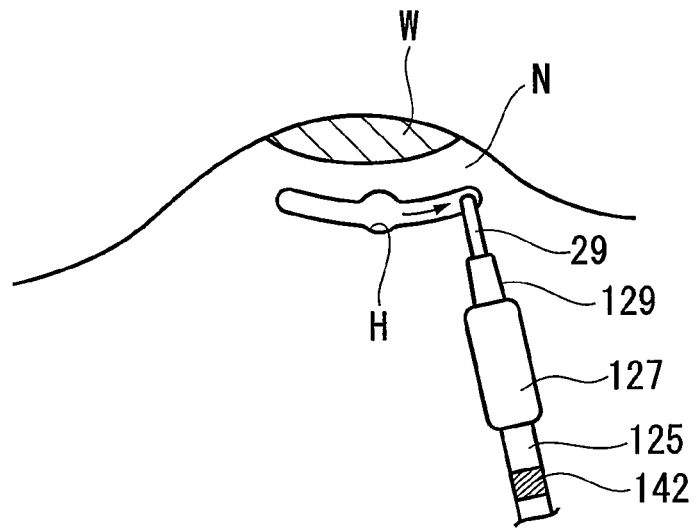
FIG. 49 is a view showing a method for mucosa separation of the third embodiment of the present invention, and shows a state where the mucosa around the aperture is incised using the high-frequency knife after inserting the high-frequency knife into the aperture.

After the step of separating, the step of incising is performed. That is, as shown in FIG. 48, the balloon insertion portion 125 is pulled back from the submucosal layer W until the outside of the aperture H. Then, similar to the step of aperture-forming, the knife portion 29 is protruded from the top end 129 of the balloon insertion portion 125, and is inserted into the aperture H. While the condition is held, high-frequency current is supplied to the knife portion 29, and the knife portion 29 is moved around the diseased part X. Therefore, as shown in FIG. 49, the mucosa N around the aperture H is incised. After the mucosa N has been incised with a certain measure of width, supplying of high-frequency current is stopped, and the knife portion 29 is retracted into the operation tube 21.

Figure 50:
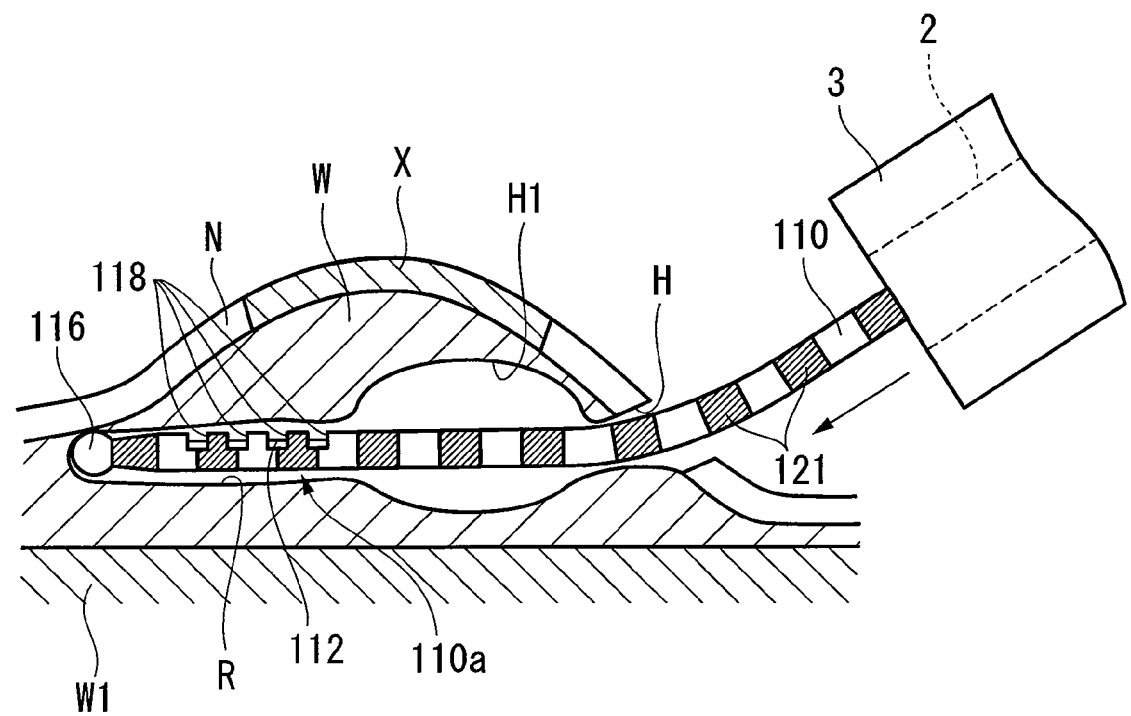
FIG. 50 is a view showing a method for mucosa separation of the third embodiment of the present invention, and shows a state where the support device insertion portion pierces the submucosal layer again after incising the mucosa around the aperture.
Figure 51:
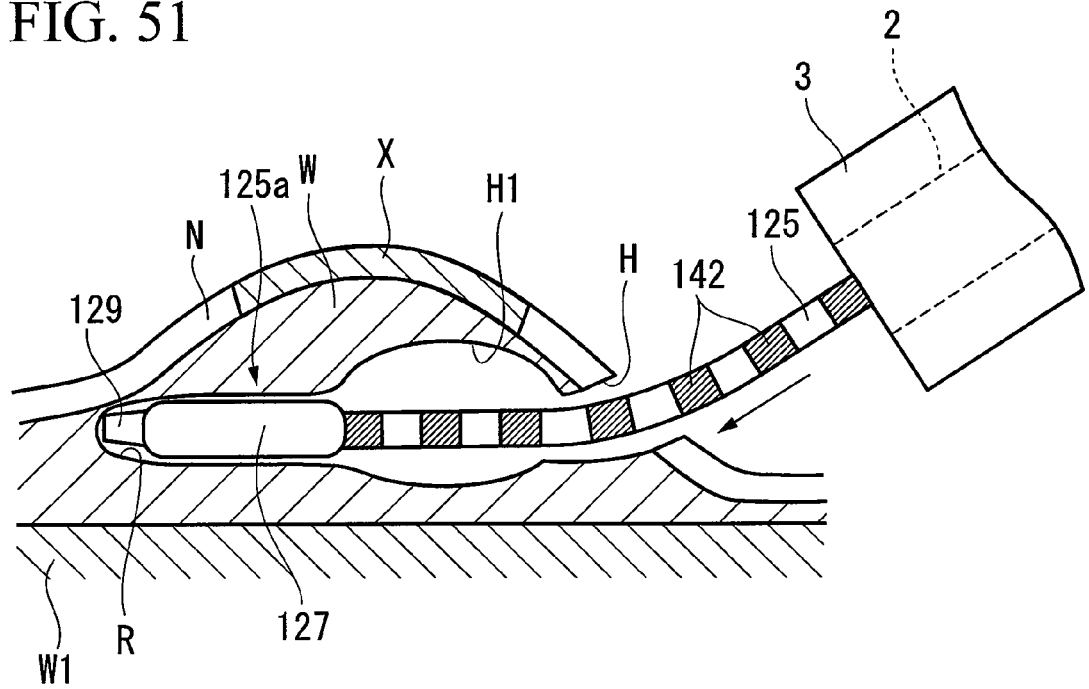
FIG. 51 is a view showing a method for mucosa separation of the third embodiment of the present invention, and shows a state where the balloon insertion portion is inserted into the submucosal layer along the insertion route again after retracting the support device insertion portion from the submucosal layer.
Figure 52:
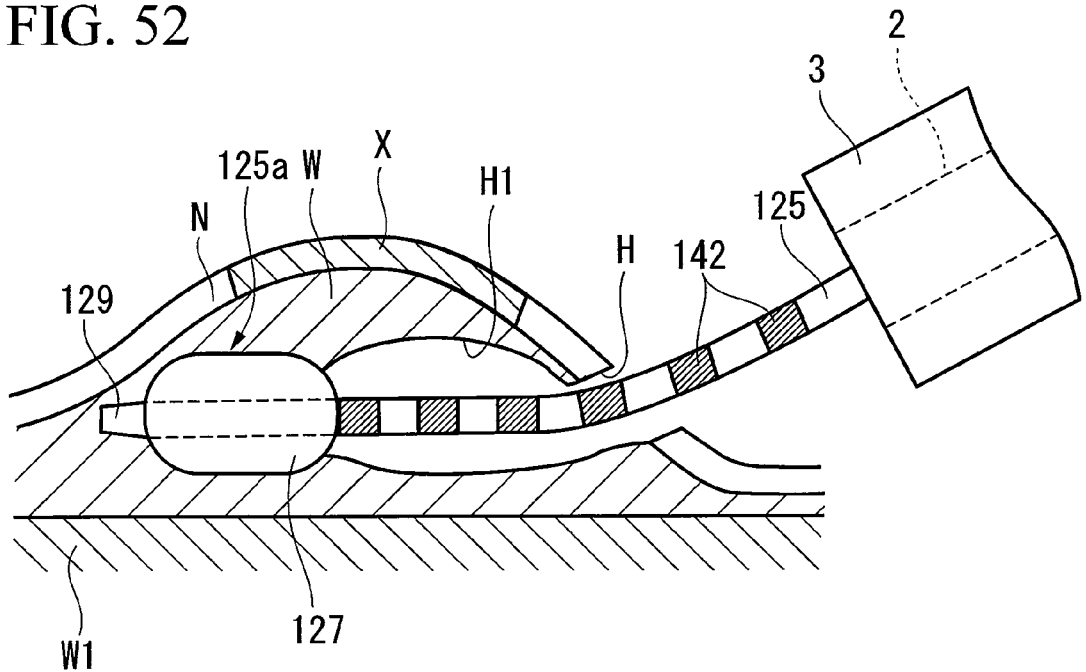
FIG. 52 is a view showing a method for mucosa separation of the third embodiment of the present invention, and shows a state where the balloon is expanded within the submucosal layer again after inserting the balloon insertion portion into the submucosal layer.
Figure 53:
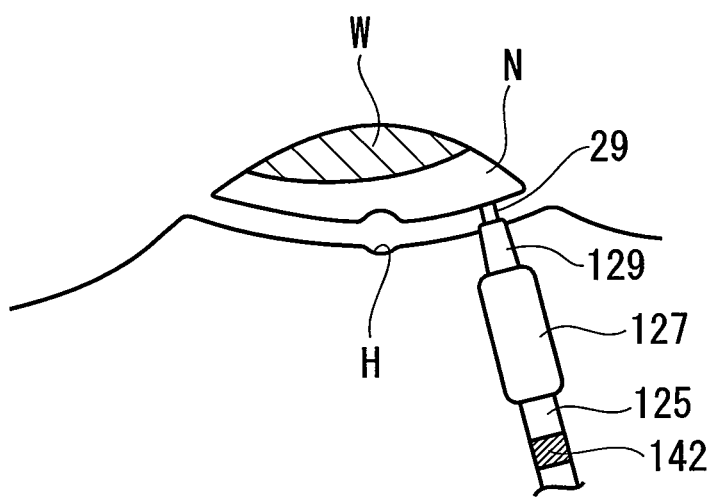
FIG. 53 is a view showing a method for mucosa separation of the third embodiment of the present invention, and shows a state where the mucosa around the aperture is further incised using the high-frequency knife after re-expanding the balloon within the submucosal layer.

If it is impossible to separate the mucosa N including the diseased part X from the submucosal layer W by only the cavity H1 because the diseased part X is so large, the steps of sticking, length-adjusting, separating and incising are repeated. That is, as shown in FIG. 50, the head portion 110*a* of the support device insertion portion 110 is re-inserted into the submucosal layer W through the aperture H according to the indicators 121 as guides, and thereby a new insertion route R is formed in the submucosal layer W located at the back of the cavity H1. Next, as shown in FIG. 51, the balloon insertion portion 125 is inserted into the insertion route R formed by second insertion of the head portion 110*a* of the support device insertion portion 110 according to the indicators 142 as guides. Then, as shown in FIG. 52, the balloon 127 is inflated, and thereby the submucosal layer W which has not been separated from the muscularis propria W1 in the first step of separating is separated from the muscularis propria W1, and a new cavity is formed. And then, as shown in FIG. 53, the step of incising is performed again.

As mentioned above, the steps of sticking, length-adjusting, separating and incising are repeated in accordance with the size of the diseased part X. Therefore, the submucosal layer W including the diseased part X is removed from the alimentary tract (refer to FIG. 25).

According to the mucosa separation apparatus and the method for mucosa separation of this embodiment, while the support device insertion portion 110 of the support device 107 and the balloon insertion portion 125 of the separation balloon insertion device 108 are alternatively inserted into the channel 2 of the endoscope 4, the insertion route R is formed and the submucosal layer W is separated from the muscularis propria W1. Therefore, it is possible to reliably separate the submucosal layer W from the muscularis propria W1 over a wide area without using the high-frequency knife 16 many times. Further, since the procedure is easily performed, the time for the operations can be shortened. Furthermore, if bleeding from the diseased part X is caused, a part which causes bleeding is compressed by inflating the balloon 127, and thereby the bleeding can be stopped quickly. As a result, it is possible to prevent an adventitious disease from occurring at the submucosal layer W of the diseased part X.

In addition, since the support device 107 and the separation balloon insertion device 108 are used so as to be alternatively inserted into the single channel 2, an endoscope 4 having a narrow insertion portion 3 can be used. As a result, it is possible to reduce the burden of a patient.

The plate member 114 is disposed inside the head portion 110*a* of the support device insertion portion 110, the curving direction of the head portion 110*a* of the support device insertion portion 110 automatically conforms to the curving direction of the insertion portion 3 of the endoscope 4. Accordingly, the head portion 110*a* of the support device insertion portion 110 can be operated to curve in a substantially same direction with the curving direction of the insertion portion 3 without adjusting the curving direction of the head portion 110*a* of the support device insertion portion 110 separately from the operation of the insertion portion 3. Therefore, the angle of the head portion 110*a* of the support device insertion portion 110 with respect to the surface of the alimentary tract can be adjusted easily. As a result, it is possible to shorten the time of the procedure for separating the submucosal layer W from the muscularis propria W1.

Since the head portion 125*a* of the balloon insertion portion 125 is inserted into the submucosal layer W along the insertion route R formed by the support device 107, the tip of the balloon insertion portion 125 does not stick into the muscularis propria W1 under the submucosal layer W. Therefore, it is unnecessary for the operator to pay extreme attention about the insertion amount of the head portion 125*a* of the balloon insertion portion 125. As a result, it is possible to safely perform the procedure regardless of the skill level of the operator, thus it is possible to severely reduce the burden of the operator.

Since the communication holes 118 which perform as the second flexible portion 105 are formed in the head portion 110*a* of the support device insertion portion 110, the head portion 110*a* of the support device insertion portion 110 can be easily curved. Therefore, if the head portion 110*a* of the support device insertion portion 110 is little protruded from the channel 2 of the endoscope 4, it is possible to reliably perform the curving operation of the head portion 110*a* of the support device insertion portion 110, thus it is possible to reliably perform the procedure in a narrow space within the alimentary tract.

Since the spherical shape portion 116 is disposed on the tip of the support device insertion portion 110, if the tip of the support device insertion portion 110 contacts the muscularis propria W1 under the submucosal layer W in the step of sticking, the muscularis propria W1 hardly becomes bruised. Therefore, it is possible to enhance the safety of the procedure.

Since the indicators 121 are disposed on the support device insertion portion 110, it is possible to accurately form the predetermined-length insertion route R. Further, since the indicators 142 are disposed on the balloon insertion portion 125, it is possible to exactly know the position of the balloon 127 inserted into the submucosal layer W. As a result, it is possible to exactly separate a desired part under the submucosal layer W from the muscularis propria W1.

Next, a fourth embodiment of a mucosa separation apparatus and a method for mucosa separation of the present invention will be explained with reference to FIG. 54 through FIG. 67. Note that, the same descriptive symbols are used for component elements that are the same as those used in the first embodiment and a description thereof is omitted.

Figure 54:
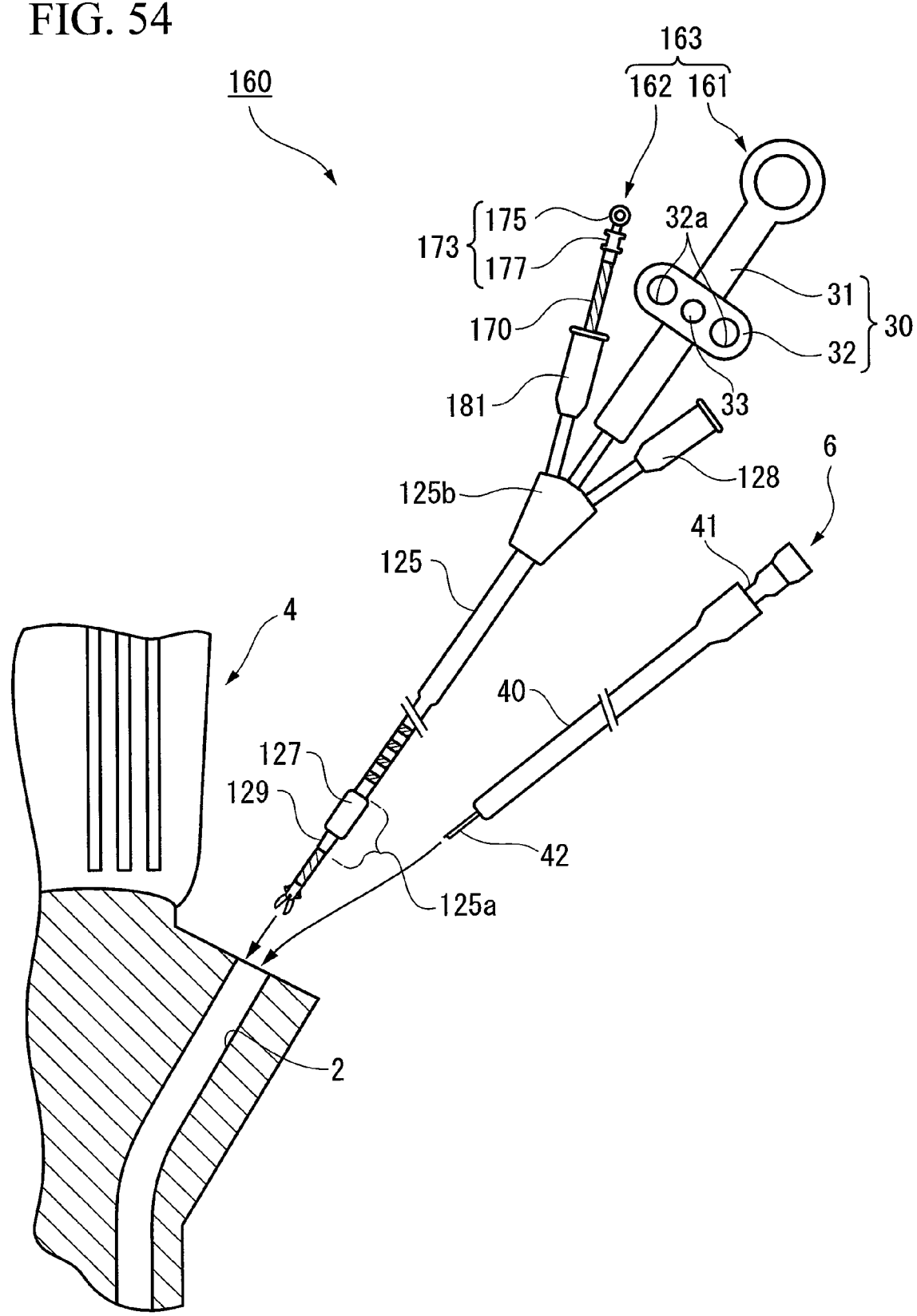
FIG. 54 is a view showing a mucosa separation apparatus of a fourth embodiment of the present invention, and is a schematic view showing a mucosa separation system including the endoscope, the support device, the separation balloon insertion device, and the submucosal local injection needle.

As shown in FIG. 54, a mucosa separation system 160 of the fourth embodiment includes the endoscope 4, a mucosa separation instrument (mucosa separation apparatus) 163, and the submucosal local injection needle 6. The mucosa separation instrument 163 locally separates the submucosal layer from the muscularis propria, and removes the diseased part of the alimentary tract. The mucosa separation instrument 163 is composed of a support device 162 and a separation balloon insertion device 161. The balloon insertion portion 125 of the separation balloon insertion device 161 is inserted into the channel 2 formed in the insertion portion 3 of the endoscope 4. A channel 180 is formed in the balloon insertion portion 125, and a support device insertion portion 170 of the support device 162 is inserted into the channel 180.

The support device 162 pierces the submucosal layer so as to form an insertion route into which the separation balloon insertion device 161 is inserted. As shown in FIG. 55 through FIG. 58, the support device 162 includes the support device insertion portion 170 which is flexible, a pair of forceps pieces 172 disposed on the tip of the support device insertion portion 170, and a forceps operation section 173 which operates the pair of forceps pieces 172.

The support device insertion portion 170 has a tubular body which is longer than the channel 180 of the balloon insertion portion 125. A top cover 174 is attached to the tip of the support device insertion portion 170, and the pair of forceps pieces 172 is pin-jointed to the top cover 174 so that the pair of forceps pieces 172 can open and close. An operation wire 176 is inserted inside the support device insertion portion 170. One end of the operation wire 176 is bifurcated, and connected to the pair of forceps pieces 172.

Figure 55:
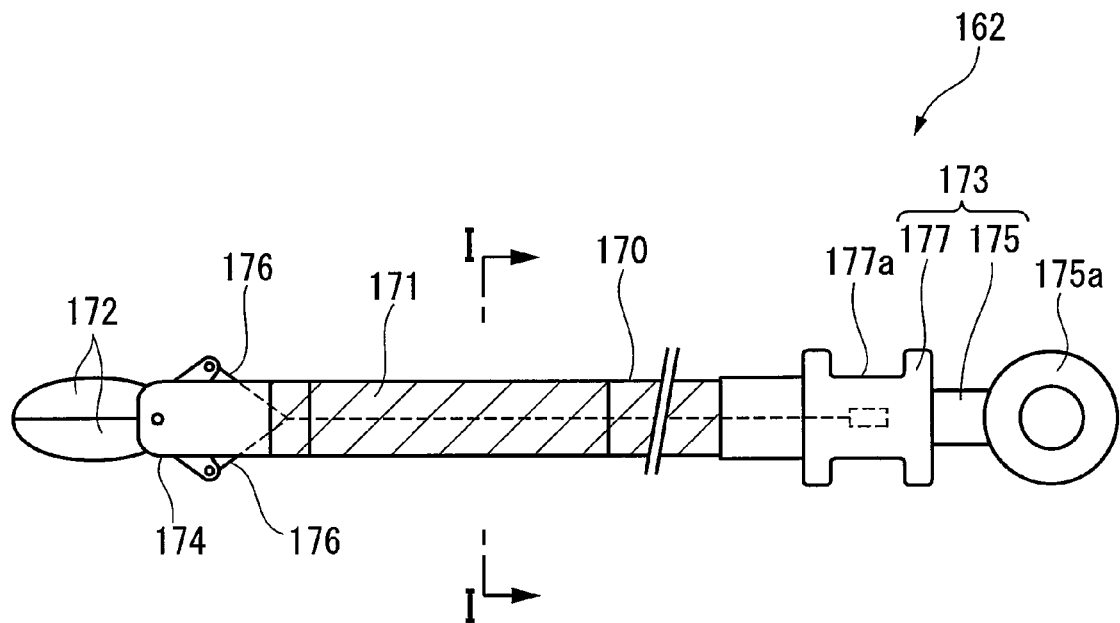
FIG. 55 is a side view showing the support device of the fourth embodiment.
Figure 56:
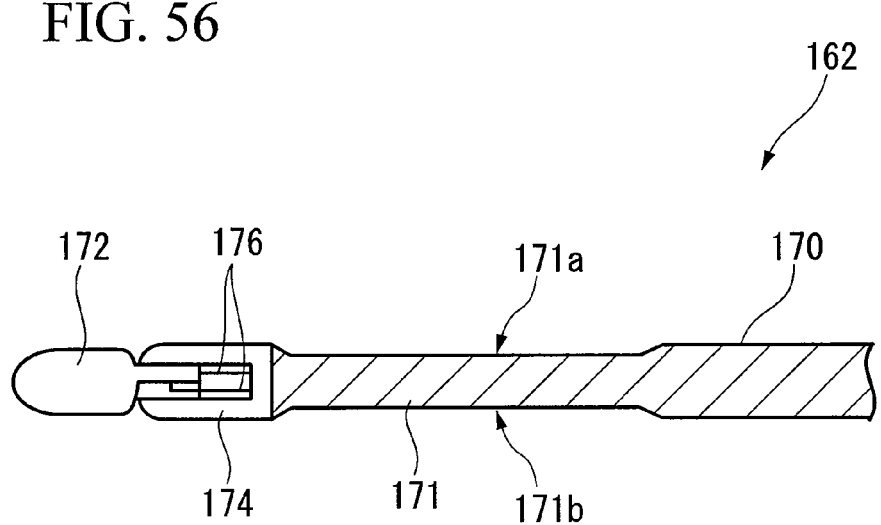
FIG. 56 is a top side view showing the support device of the fourth embodiment.
Figure 58:
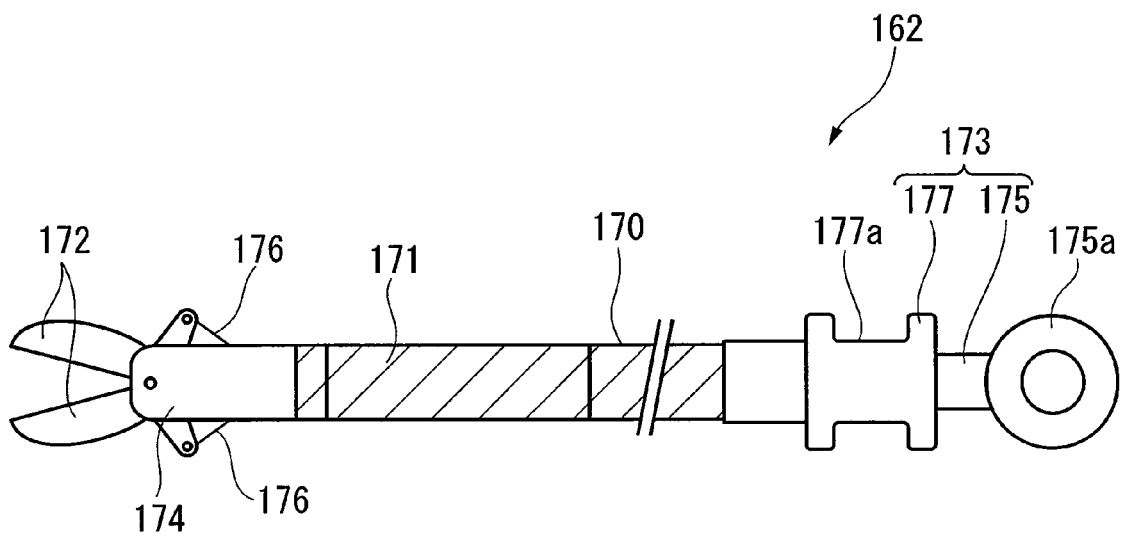
FIG. 58 is a view showing the support device of the fourth embodiment, and shows a plan view of a state where forceps which form a pair are separated from each other.

The forceps operation section 173 is disposed on a terminal end of the support device insertion portion 170, and includes a operation section main body 175, and a sliding portion 177 which is slidable with respect to the operation section main body 175. The other end of the operation wire 176 is connected to the sliding portion 177. When the sliding portion 177 is moved toward the terminal end of the support device insertion portion 170 with respect to the operation section main body 175, as shown in FIG. 55, the operation wire is pulled, and thereby the pair of forceps pieces 172 close. When the sliding portion 177 is moved toward the tip of the support device insertion portion 170 with respect to the operation section main body 175, as shown in FIG. 58, the operation wire is pushed, and thereby the pair of forceps pieces 172 opens.

In addition, a finger hanging ring 175a on which a thumb of an operator can be hanged is attached to the terminal of the operation section main body 175. Recessed portions 177a to which a forefinger and a middle finger of the operator can be respectively engaged are formed in the center of the sliding portion 177. The operator hangs the thumb of one hand on the finger hanging ring 175a, and respectively engages the forefinger and the middle finger of the one hand with the recessed portions 177a. Thereby, he/she can easily operate the opening and closing operation of the pair of forceps pieces 172 using only one hand.

Figure 57:
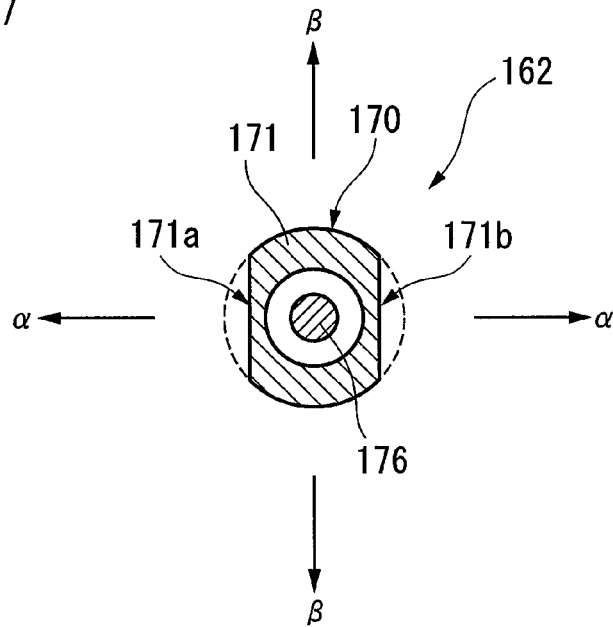
FIG. 57 is a sectional view taken along a line I-I in FIG. 55.

As shown in FIG. 57, two planes 171a and 171b which are separated from each other in a radial direction of the support device insertion portion 170 so as to across the axis L are formed in a predetermined area of the support device insertion portion 170 which is closer to the base portion of the support device insertion portion 170 than the pair of forceps pieces 172. Since the planes 171a and 171b are formed in the support device insertion portion 170, the diameter of a part of the support device insertion portion 170 in which the planes 171a and 171b are not formed is smaller than that of the other part of the support device insertion portion 170 in which the planes 171a and 171b are formed. Therefore, the support device insertion portion 170 inclines to curve not in an arranging direction (direction α) of the planes 171a and 171b but in a perpendicular direction of the arranging direction (direction β). The direction α is perpendicular to an opening and closing direction of the pair of forceps pieces 172. When a predetermined-strength force acts on the area in which the planes 171a and 171b are formed, the area performs as a second flexible portion 171 which curves in the direction a before the other area. That is, when the tip of the support device insertion portion 170 contacts to the muscularis propria W1 under the submucosal layer W, the second flexible portion 171 curves so as to warp upward by a reaction force from the muscularis propria W1.

Figure 59:
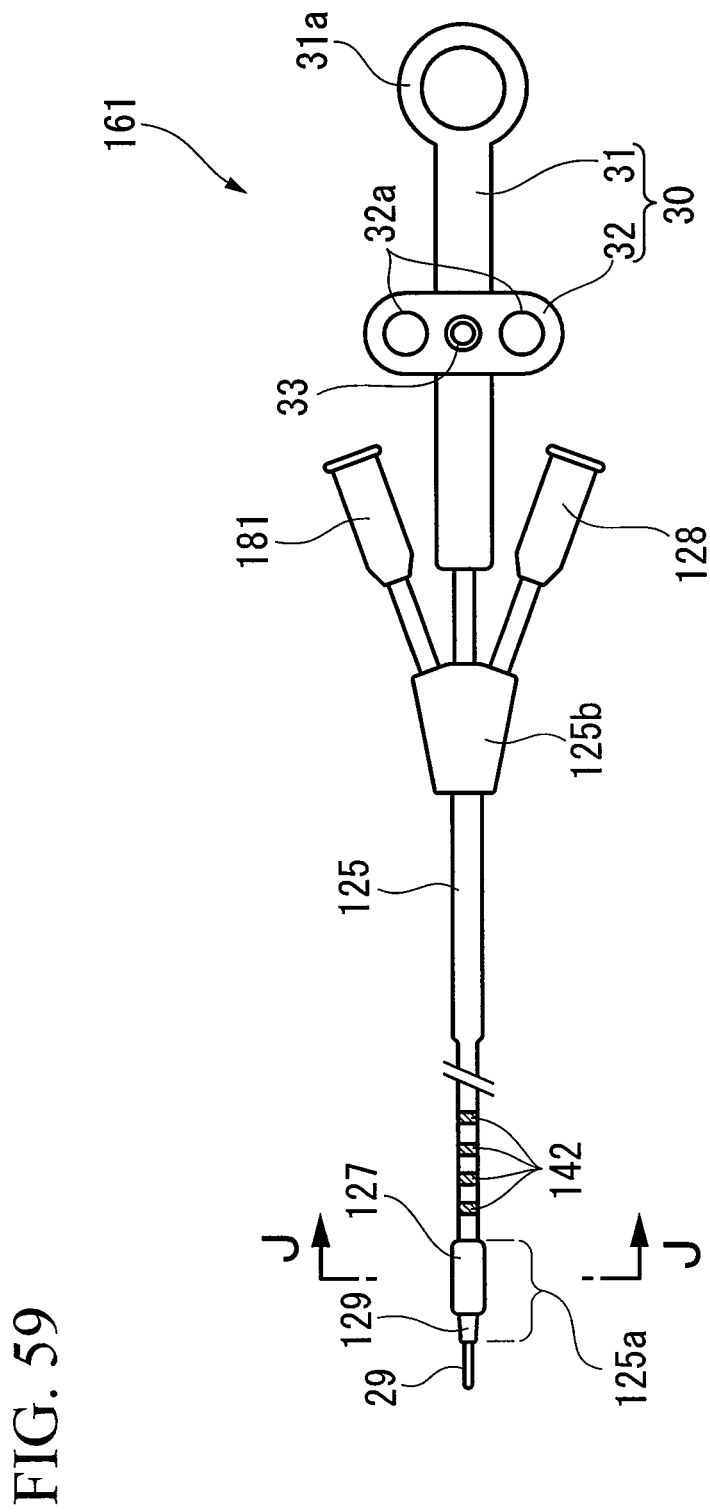
FIG. 59 is a plan view showing the separation balloon insertion device of the fourth embodiment.
Figure 60:
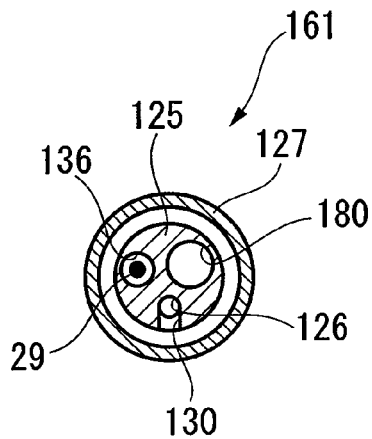
FIG. 60 is a sectional view taken along a line J-J in FIG. 59.

The balloon insertion portion 125 of the separation balloon insertion device 161 has a long tubular body, as shown in FIG. 59 and FIG. 60, and a channel 180 is formed within the balloon insertion portion 125 from the terminal end of the balloon insertion portion 125 to the tip thereof along the passage 126. The support device 162 is inserted into the channel 180. An insertion port 181 into which the support device 162 is inserted is disposed on the terminal end of the channel 180.

The method for mucosa separation for removing a diseased part X developing inside an alimentary tract from a submucosal layer W using the mucosa separation system 160 as mentioned above will be explained.

The method for mucosa separation of this embodiment includes the steps of inflating, aperture-forming, inserting, sticking, length-adjusting, separating and incising. Each of the steps will be explained.

First, similar to the first embodiment, the step of inflating is performed (refer to FIG. 9). After that, the step of aperture-forming is performed. That is, the support device insertion portion 170 of the support device 162 is inserted into the channel 180 of the balloon insertion portion 125, and then the balloon insertion portion 125 is inserted into the channel 2 of the insertion portion 3. Then, an aperture H with a predetermined size is formed in a mucosa N in the vicinity of the diseased part X being inflated using the knife portion 29.

Figure 61:
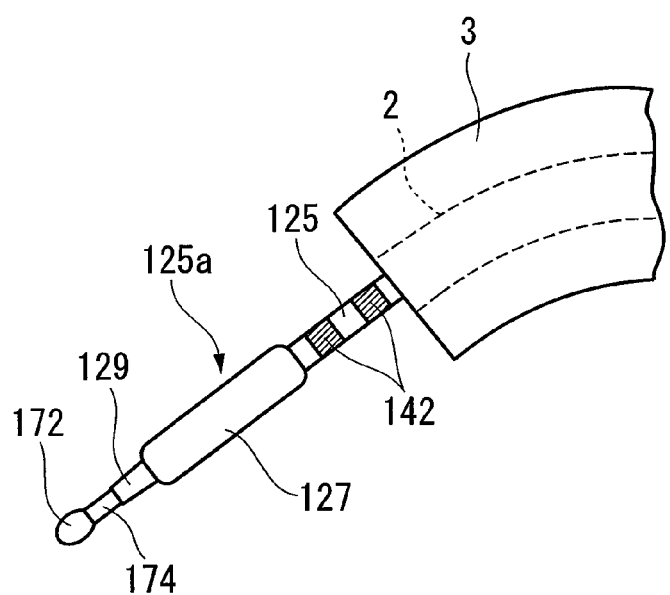
FIG. 61 is a view showing a state where the tip of the support device insertion portion is protruded from the tip of the insertion portion of the endoscope.
Figure 62:
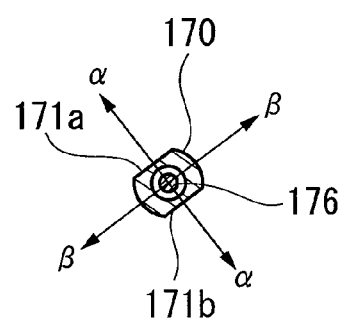
FIG. 62 is a view showing a state where an insertion portion main body of the support device is protruded from the tip of an instrument main body of the submucosal layer separation instrument, and shows a sectional view of the support device insertion portion which is protruded from the tip of the insertion portion of the endoscope.

After the aperture H is formed, the support device insertion portion 170 is further inserted into the channel 180, as shown in FIG. 61, and thereafter the tip of the support device insertion portion 170 is protruded from the tip of the balloon insertion portion 125. At this time, the position of the second flexible portion 171 around the axis L is adjusted so that the support device insertion portion 170 is curved upward. That is, as shown in FIG. 62, the support device insertion portion 170 is rotated around the axis L so as to make the direction α as mentioned above parallel to the paper surface of FIG. 62.

Figure 63:
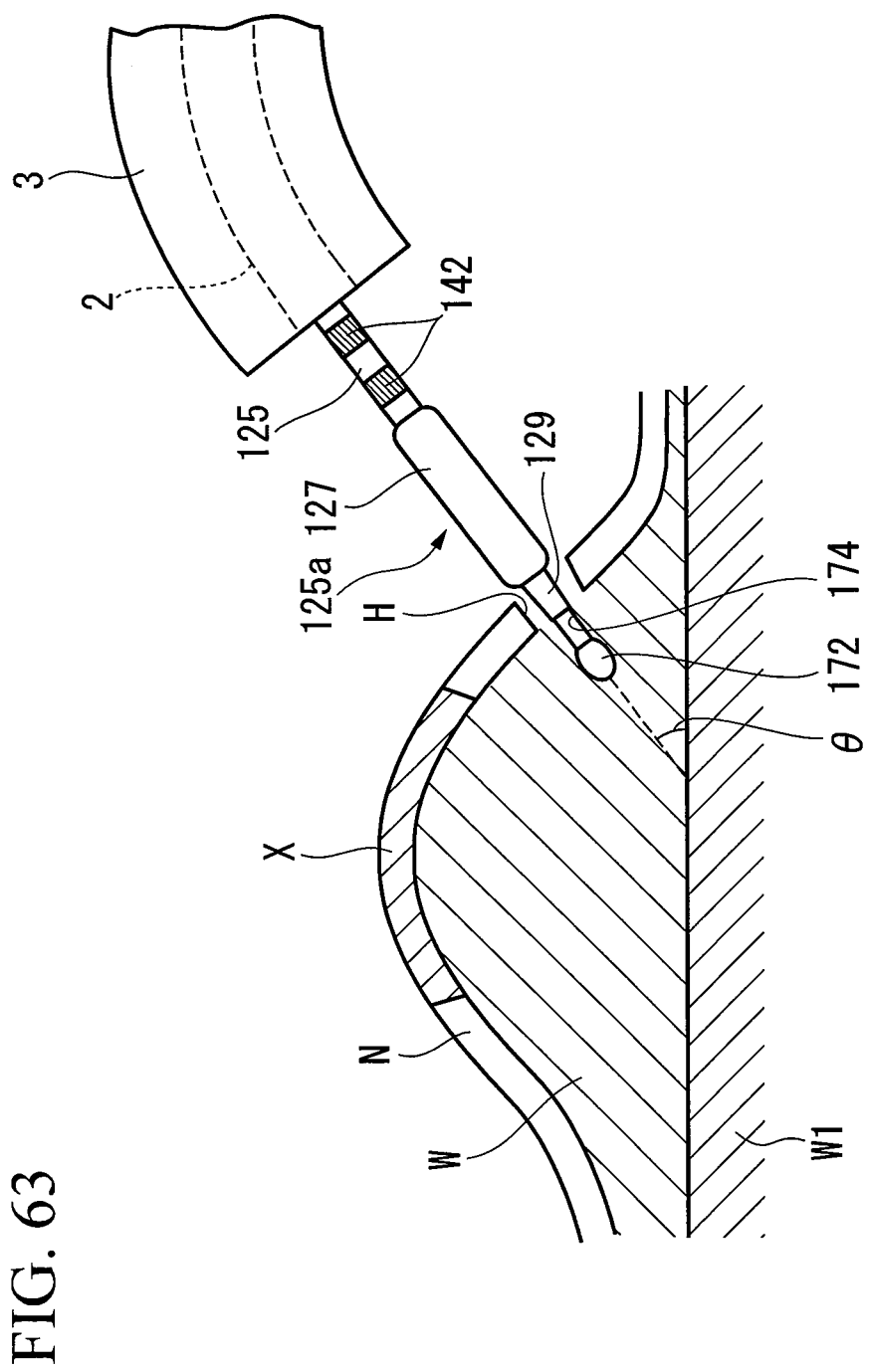
FIG. 63 is a view showing a method for mucosa separation of the fourth embodiment of the present invention, and shows a state where the tip of the support device insertion portion is inserted into the aperture.

After the step of aperture-forming, the step of inserting is performed. That is, as shown in FIG. 63, the top end 129 of the balloon insertion portion 125 is inserted into the submocosa W through the aperture H. At this stage, the head portion 129 of the balloon insertion portion 125 is across a surface of the alimentary tract by an angle θ.

Figure 64:
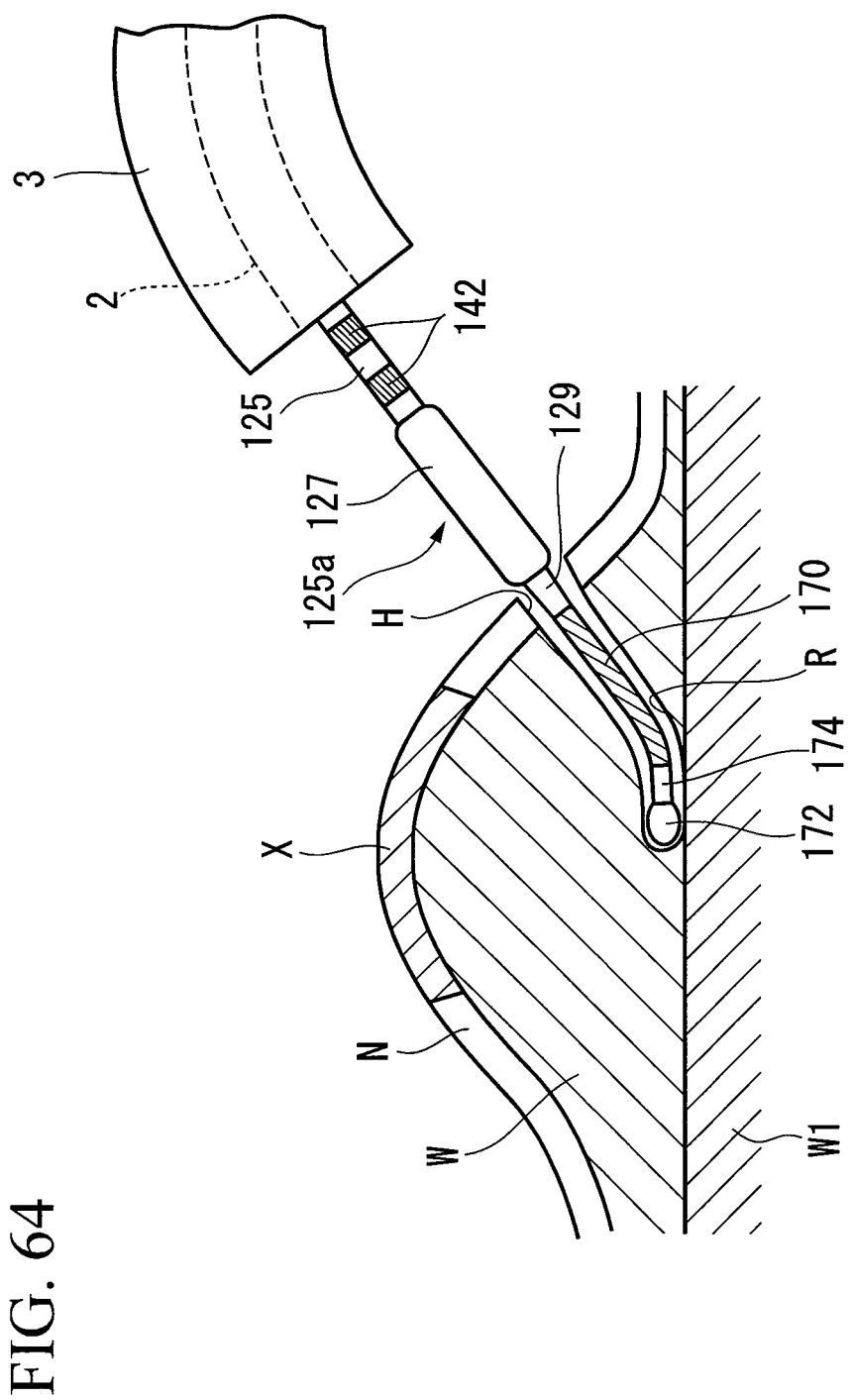
FIG. 64 is a view showing a method for mucosa separation of the fourth embodiment of the present invention, and shows a state where the head portion of the support device insertion portion is curved after inserting the tip of the support device insertion portion into the aperture.

After the step of inserting, the step of sticking is performed. That is, the pair of forceps pieces 172 of the support device insertion portion 170 is inserted into the submucosa W through the aperture H. At the beginning of the inserting, the head portion of the support device insertion portion 170 is advanced toward the muscularis propria W1 under the submucosal layer W along with maintaining the angle θ with respect to the surface of the alimentary tract. As shown in FIG. 64, when the pair of forceps pieces 172 disposed at the tip of the support device insertion portion 170 contacts the muscularis propria W1 which is harder than the submucosal layer W, the support device insertion portion 170 is curved so as to warp upward due to the cross-sectional property of the second flexible portion 171 by a reaction force acting from the muscularis propria W1. Therefore, the tip of the support device insertion portion 170 is turned along the surface of the muscularis propria W1, and then is advanced within the submucosal layer W.

Figure 65:
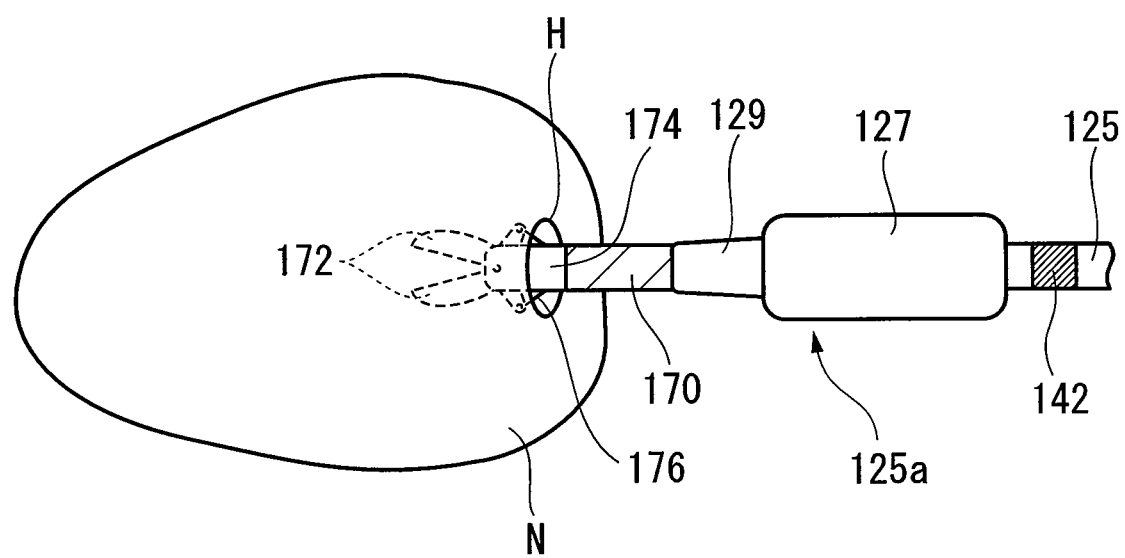
FIG. 65 is a view showing a method for mucosa separation of the fourth embodiment of the present invention, and shows a state where the tip of the support device insertion portion pierces the submucosal layer from the aperture, while the pair of forceps is opening and closing.

When the insertion route R is formed, as shown in FIG. 65, it is preferable to open and close the pair of forceps pieces 172 by pushing and pulling the sliding portion 177. By opening and closing the pair of forceps pieces 172, the pair of forceps pieces 172 is advanced within the submucosal layer W along with pushing the body tissue. Therefore, the insertion route R can be formed reliably.

Figure 66:
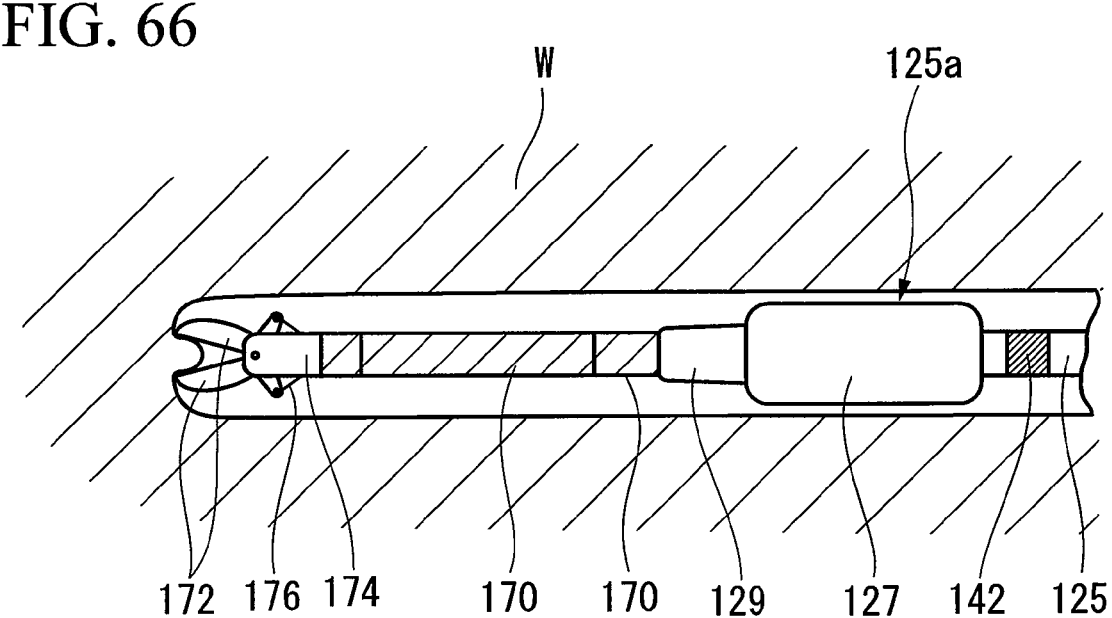
FIG. 66 is a view showing a method for mucosa separation of the fourth embodiment of the present invention, and shows a state where the submucosal layer located at the remotest area of the insertion route is grasped by the pair of forceps after forming the insertion route by the support device.
Figure 67:
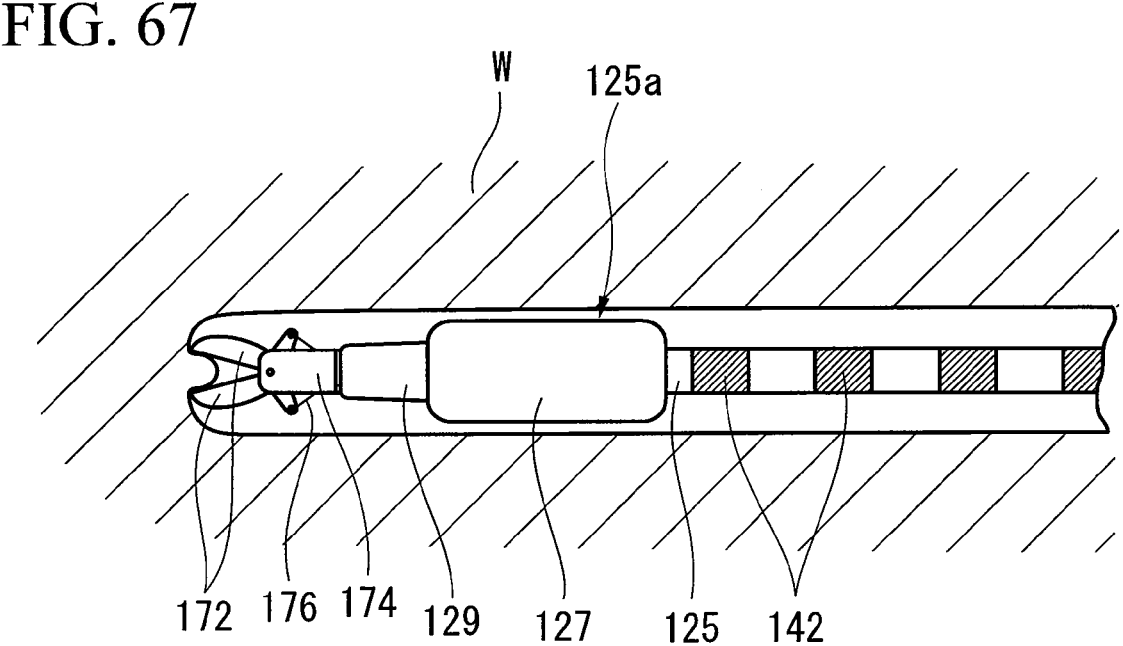
FIG. 67 is a view showing a method for mucosa separation of the fourth embodiment of the present invention, and shows a state where a separation balloon treatment portion is pushed into the insertion route, while the submucosal layer is grasped by the pair of forceps.

After the step of sticking, the step of length-adjusting is performed. That is, with holding the support device 162 in place, the balloon insertion portion 125 of the separation balloon insertion device 161 is pushed into the channel 2 according to the indicators 142 as guides. Therefore, the balloon insertion portion 125 is inserted into the submucosal layer W by moving the balloon insertion portion 125 along the insertion route R, and the support device insertion portion 170 of the support device 162 is retracted into the channel 180 of the balloon insertion portion 125. At this time, since the balloon insertion portion 125 is moved along the insertion route R, the balloon insertion portion 125 is inserted into the submucosal layer W so as to be parallel to the surface of the alimentary tract. Note that, as shown in FIG. 66, it is preferable to grasp the submucosal layer W located at a remotest area of the insertion route R by the pair of the forceps pieces 172, and then, as shown in FIG. 67, it is preferable to push the balloon insertion portion 125 into the insertion route R.

After the step of length-adjusting, similar to the first embodiment, the step of separating and the step of incising are performed. As mentioned above, the steps of sticking, length-adjusting, separating and incising are repeated in accordance with the size of the diseased part X. Therefore, the submucosal layer W including the diseased part X is removed from the alimentary tract (refer to FIG. 25).

According to the mucosa separation apparatus and the method for mucosa separation of this embodiment, since the head portion 125a of the balloon insertion portion 125 is inserted into the submucosal layer W along the insertion route R formed by the support device 162, similar to the third embodiment, the tip of the balloon insertion portion 125 does not stick into the muscularis propria W1 under the submucosal layer W. Therefore, it is possible to safely perform the procedure regardless of the skill level of the operator, thus it is possible to severely reduce the burden of the operator.

Since the support device insertion portion 170 of the support device 162 is inserted into the alimentary tract using the channel 180 of the separation balloon insertion device 161, it is unnecessary to replace the support device 162 with the separation balloon insertion device 161. Therefore, it is possible to shorten the time for the operations.

Since the support device 162 includes the pair of forceps pieces 172, the insertion route R can be formed easily. Further, by grasping the submucosal layer W located at a remotest area of the insertion route R using the pair of forceps pieces 172, the balloon insertion portion 125 is inserted into the insertion route R while the tip of the support device insertion portion 170 is held in place. Therefore, the length-adjusting can be performed easily.

Note that, in the third embodiment, after only the head portion 110a of the support device insertion portion 110 is inserted into the aperture H, the curving angle of the head portion 110a of the support device insertion portion 110 is adjusted. However, after the curving angle of the head portion 110a of the support device insertion portion 110 is adjusted, the head portion 110a of the support device insertion portion 110 may be inserted into the submucosal layer W.

In the third embodiment, the support device 107 is provided with the spherical shape portion 116. However, similar to the fourth embodiment, the support device 107 may be provided with the pair of forceps pieces 172. Further, similar to the third embodiment, the support device 162 may be provided with the spherical shape portion 116.

In the third and the fourth embodiments, the separation balloon insertion devices 108 and 161 can be applied to the endoscope 4 having a single channel. However, the separation balloon insertion devices 108 and 161 may be applied to an endoscope having another channel (second channel) formed in the insertion portion 3 other than the channel 2. In this case, the submucosal local injection needle 6 may be inserted into the another channel along with the separation balloon insertion devices 108 and 161 are inserted into the channel 2. Therefore, since one of the separation balloon insertion device 108 and the support device 107 is inserted into the alimentary tract with the submucosal local injection needle 6, it is possible to quickly transfer from the step of inflating the diseased part X to the step of separating without replacing instruments. As a result, it is possible to shorten the operation time which goes from inflating of the diseased part X to separation of the submucosal layer W.

Forceps for grasping the diseased part X may be inserted into the second channel, not the submucosal local injection needle 6. In this case, since one of the separation balloon insertion device 108 and the support device 107 is inserted into the alimentary tract with the submucosal local injection needle 6 through the second channel, it is possible to separate the mucosa from the muscularis propria W1 along with the diseased part X is grasped by the grasping forceps. Therefore, the balloon 127 can be inserted into the submucosal layer W without being restricted by the diseased part X already separated. Further, the mucosa can be separated while grasping the mucosa so as to not lose the diseased part X. As a result, the procedure can be performed accurately.

The mucosa separation apparatus may be composed of the separation balloon insertion device 161 of the fourth embodiment and the support device 107 of the third embodiment. Therefore, since the support device 107 can be inserted into the alimentary tract through the channel 180 of the separation balloon insertion device 161, it is possible to save a step of replacing the separation balloon insertion device 108 with the support device 107. Other effects of this embodiment are similar to the third embodiment.

Next, a fifth embodiment of a mucosa separation apparatus and a method for mucosa separation of the present invention will be explained with reference to FIG. 68 through FIG. 75. Note that, the same descriptive symbols are used for component elements that are the same as those used in the first embodiment and a description thereof is omitted.

Figure 68:
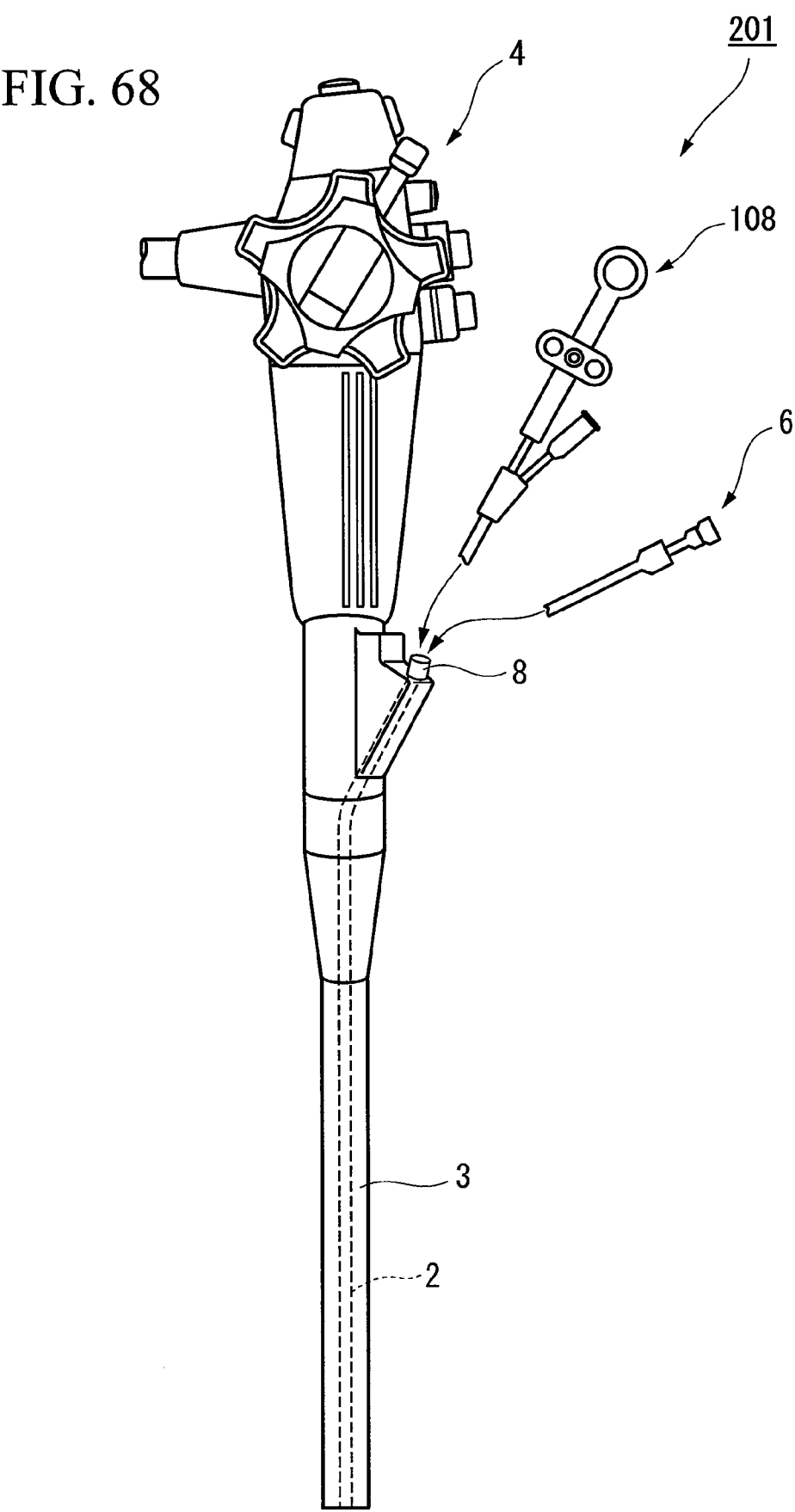
FIG. 68 is a view showing a mucosa separation apparatus of a fifth embodiment of the present invention, and shows a schematic view of a mucosa separation system including the endoscope, the separation balloon insertion device, and the submucosal local injection needle.

As shown in FIG. 68, a mucosa separation system 201 of this embodiment includes the endoscope 4, the separation balloon insertion device (mucosa separation apparatus) 108 and the submucosal local injection needle 6. The separation balloon insertion device 108 or the submucosal local injection needle 6 is inserted into the channel 2 formed in the insertion portion 3 of the endoscope 4 through the sleeve 8 as appropriate.

Figure 69:
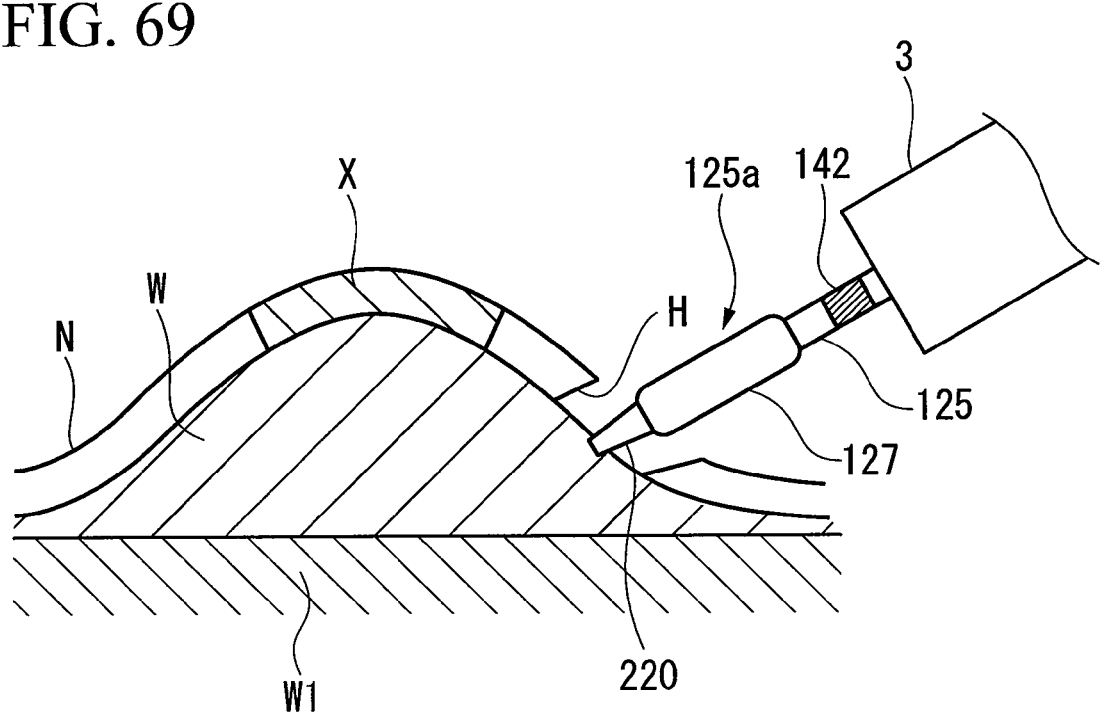
FIG. 69 is a view showing a method for mucosa separation of the fifth embodiment of the present invention, and shows a state where the tip of the balloon insertion portion is inserted into the aperture formed within in the mucosa.

As shown in FIG. 69, a top end (third flexible portion) 220 of the balloon insertion portion 125 is formed like a tapered shape so as the diameter thereof gradually reduces toward the top end. The rigidity of the top end 220 is higher than the lower flexible limit of the rigidity of the wall of the alimentary tract, and is lower than the higher flexible limit of the rigidity of the wall of the alimentary tract. Note that, the lower flexible limit means the rigidity of the top end of which the top end cannot be inserted into the submucosal layer if the top end softens below the lower flexible limit. The higher flexible limit means the rigidity of the top end of which the top end may stick into the muscularis propria under the submucosal layer if the top end hardens beyond the higher flexible limit. In other words, the rigidity of the top end 220 is higher than that of the submucosal layer, and is lower than that of the muscularis propria. Therefore, the top end 220 is not curved when only it is inserted into the submucosal layer. It is curved when it contacts the muscularis propria.

The lower flexible limit and the higher flexible limit of the rigidity of the top end 220 are supplementarily explained. In the chart of FIG. 75, examples of measurements of the lower flexible limit and the higher flexible limit of the rigidity of the head portion according to force acted on catheters are shown, when the several kinds of catheters having different diameters are inserted into a suilline large intestine.

For example, with a catheter of which the diameter of the top end is 0.8 mm, if the catheter is tried to be inserted into the suilline large intestine with the force being less than 1.7 N, the catheter can not be inserted into the intestine because the force is too weak. In contrast, if the catheter is tried to be inserted into the suilline large intestine with the force being equal to or more than 1.7 N, the catheter can be inserted into the submucosal layer of the suilline large intestine. Further, if the catheter is tried to be inserted into the suilline large intestine with the force being more than 2.5 N, the catheter pierces the muscularis propria under the submucosal layer.

The examples shown in FIG. 75 apply to a suilline large intestine. However, the rigidity of human large intestine is higher than that of a suilline large intestine. Actually, the lower flexible limit and the higher flexible limit of the human large intestine are substantially 1.5 to 2.0 times higher than that of a suilline large intestine. In this embodiment, since the separation balloon insertion device 108 is used for the alimentary tract of human, the rigidity of the top end 220 also is based on the lower flexible limit and the higher flexible limit of the rigidity of the wall of the alimentary tract of human.

For setting the rigidity of the top end 220 to an appropriate value, it is preferable to select materials having an appropriate rigidity, and to vary the thickness of the top end 220.

The method for mucosa separation for removing a diseased part X developing inside an alimentary tract from a submucosal layer W using the mucosa separation system 201 as mentioned above will be explained.

The method for mucosa separation of this embodiment includes the steps of inflating, aperture-forming, inserting, length-adjusting, curving, separating and incising. Each of the steps will be explained.

First, similar to the first and the second embodiments, the steps of inflating and aperture-forming are performed (refer to FIG. 9 and FIG. 40). After that, the step of inserting is performed. That is, after the knife portion 29 is retracted, as shown in FIG. 69, only the top end 220 of the balloon insertion portion 125 is inserted into the aperture H.

Figure 70:
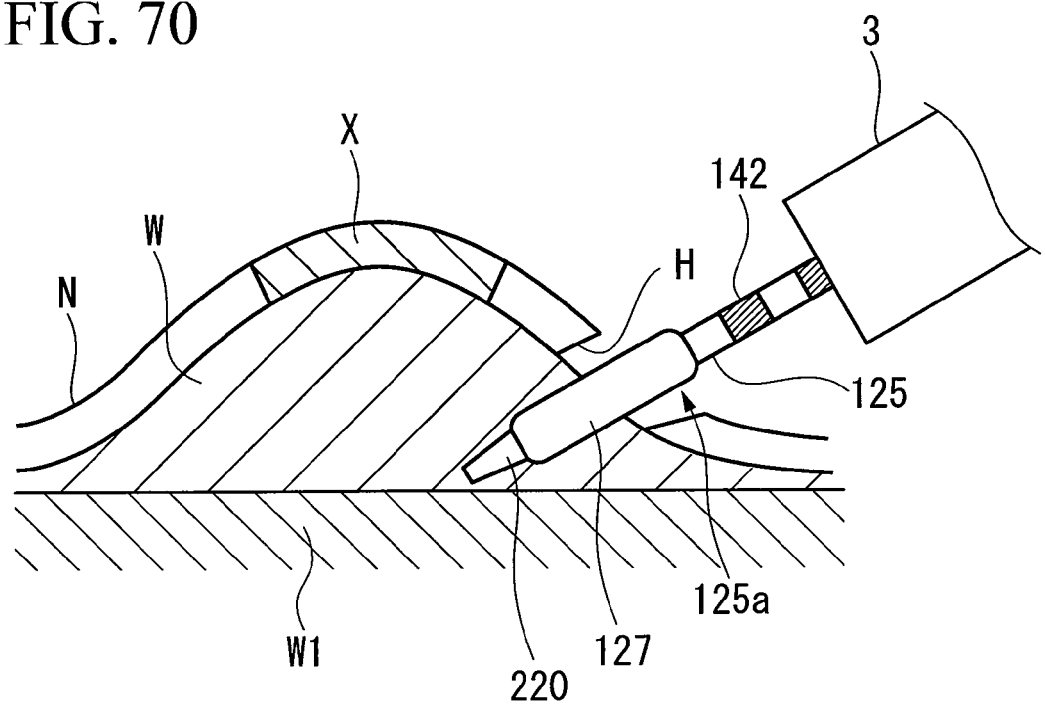
FIG. 70 is a view showing a method for mucosa separation of the fifth embodiment of the present invention, and shows a state where the head portion of the balloon insertion portion pierces the submucosal layer through the aperture.
Figure 71:
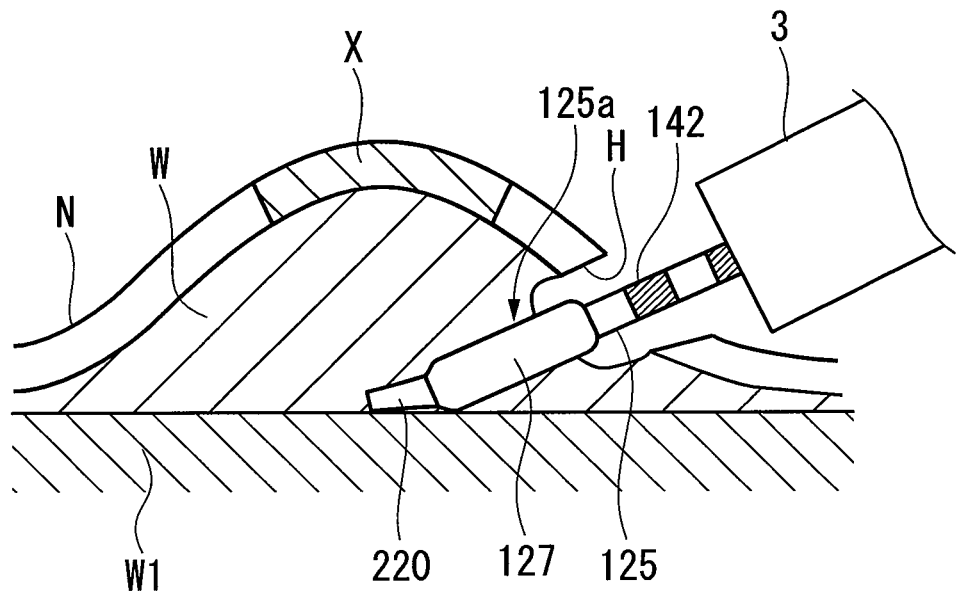
FIG. 71 is a view showing a method for mucosa separation of the fifth embodiment of the present invention, and shows a state where the head portion of the balloon insertion portion is curved by pushing the head portion onto a muscularis propria under the submucosal layer.
Figure 72:
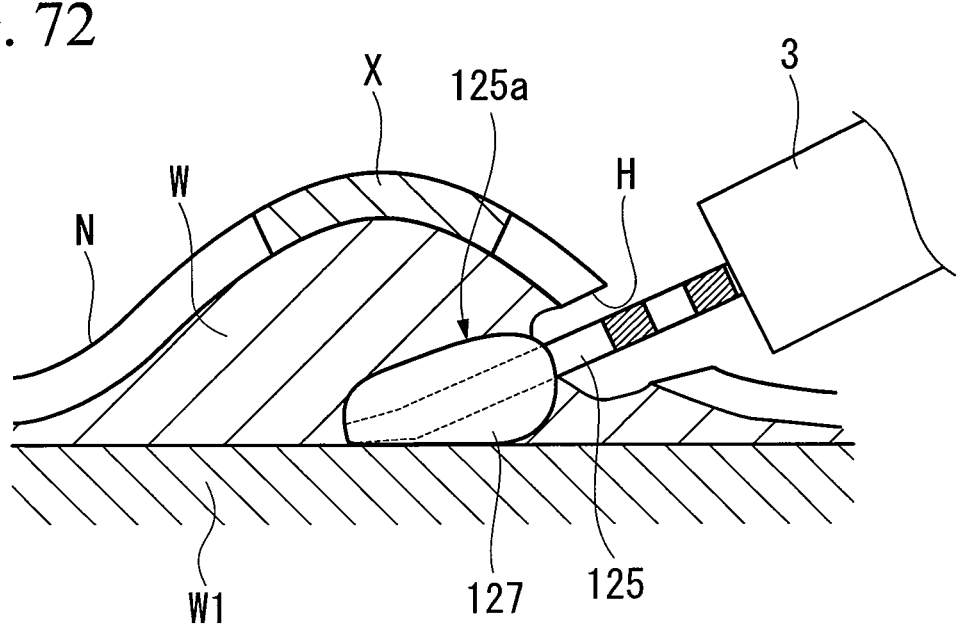
FIG. 72 is a view showing a method for mucosa separation of the fifth embodiment of the present invention, and shows a state where the balloon is expanded within the submucosal layer after pushing the head portion of the balloon insertion portion onto the muscularis propria.

After the step of inserting, the step of length-adjusting is performed. That is, as shown in FIG. 70, the head portion 125*a* of the balloon insertion portion 125 is pushed into the submucosal layer W according to the indicators 142 as guides. Next, the step of curving is performed. That is, the head portion 125*a* of the balloon insertion portion 125 is further pushed into the submucosal layer W. When the top end 220 of the balloon insertion portion 125 contacts the muscularis propria W1, as shown in FIG. 71, the top end 220 is curved. When the top end 220 of the balloon insertion portion 125 reaches the muscularis propria W1, the step of length-adjusting is transferred to the step of curving without an operation from the operator. Therefore, the step of curving may be included in the step of length-adjusting.

When the operator pushes the separation balloon insertion device 108 into the channel 2 with a weak force, it does not cause problems. However, when the operator accidentally pushes the separation balloon insertion device 108 into the channel 2 with a powerful force, the top end 220 may pierced the muscularis propria W1. Even in this case, since the rigidity of the top end 220 of the balloon insertion portion 125 is higher than the lower flexible limit of the rigidity of the wall of the alimentary tract, and is lower than the higher flexible limit of the rigidity of the wall of the alimentary tract, if the operator accidentally pushes the separation balloon insertion device 108 into the channel 2 with a powerful force, the top end 220 is curved, and thereby the force acting on the top end 220 is lost. Therefore, the top end 220 does not pierce the muscularis propria W1.

When the operator feels a change of the intensity of the force for inserting the separation balloon insertion device 108 into the channel 2, the operator acknowledges that the top end 220 has reached the muscularis propria W1 and it has been curved.

After the step of curving, the step of separating is performed. That is, a fluid is supplied into the passage 126 through the fill port 128 using a syringe (not shown). The fluid supplied into the passage 126 is supplied to the balloon 127 through the communication hole 130, and thereby the balloon 127 is inflated (shown in FIG. 72). Therefore, a part of the submucosal layer W is separated from the muscularis propria W1 existing under the submucosal layer W. Then, the fluid is discharged from the balloon 127 through the fill port 128, and thereby the balloon 127 deflates to its original shape. As a result, as shown in FIG. 47, a cavity H1 is formed between the muscularis propria W1 and the submucosal layer W separated from the muscularis propria W1.

After the step of separating, the step of incising is performed. That is, the balloon insertion portion 125 is pulled back from the submucosal layer W until the outside of the aperture H. Then, similar to the step of aperture-forming, the knife portion 29 is protruded from the top end 220 of the balloon insertion portion 125, and is inserted into the aperture H (refer to FIG. 20). While the condition is held, high-frequency current is supplied to the knife portion 29, and the tip of the balloon insertion portion 125 is moved around the diseased part X. Therefore, the mucosa N around the aperture H is incised (refer to FIG. 21). After the mucosa N has been incised with a certain measure of width, supplying of high-frequency current is stopped, and the knife portion 29 is retracted into the operation tube 21.

Figure 73:
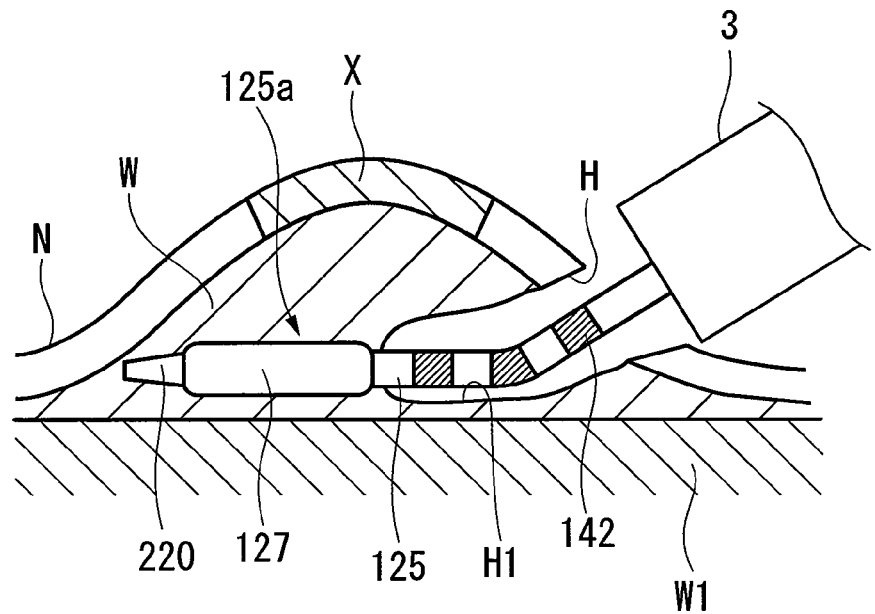
FIG. 73 is a view showing a method for mucosa separation of the fifth embodiment of the present invention, and shows a state where the balloon insertion portion pierces the submucosal layer again.
Figure 74:
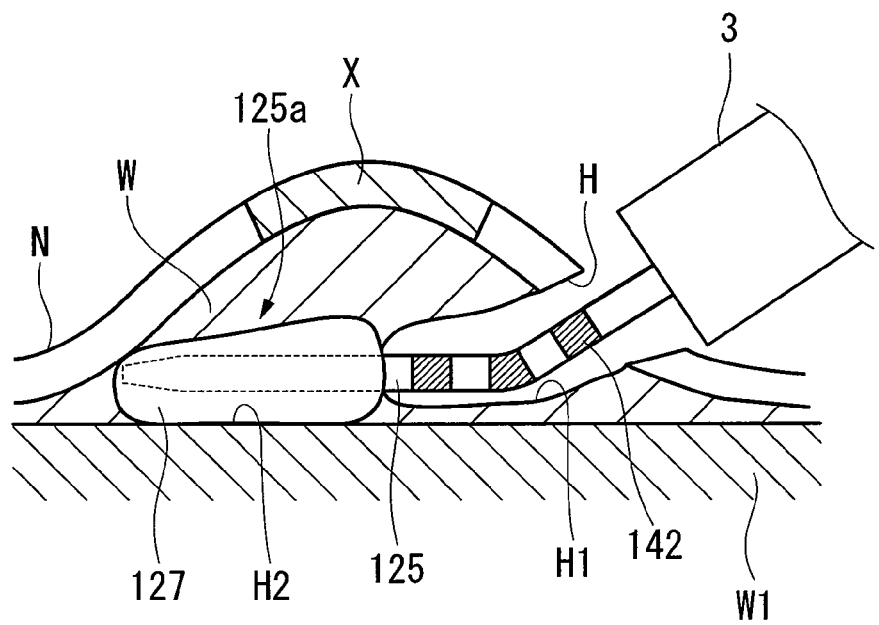
FIG. 74 is a view showing a method for mucosa separation of the fifth embodiment of the present invention, and shows a state where the balloon is expanded within the submucosal layer again after piercing the submucosal layer by the balloon insertion portion.

If it is impossible to separate the mucosa N including the diseased part X from the submucosal layer W by only the cavity H1 because the diseased part X is so large, the steps of length-adjusting, separating and incising are repeated. That is, as shown in FIG. 73, the head portion 125*a* of the balloon insertion portion 125 is re-inserted into the submucosal layer W through the aperture H according to the indicators 142 as guides, and thereby the head portion 125*a* of the balloon insertion portion 125 is further pushed into the submucosal layer W located at back of the cavity H1. Next, as shown in FIG. 74, the balloon 127 is inflated, and thereby the submucosal layer W which has not been separated from the muscularis propria W1 at the first step of separating is separated form the muscularis propria W1, and a new cavity H2 is formed. And then, the step of incising is performed again (refer to FIG. 53).

As mentioned above, the steps of length-adjusting (including the step of curving), separating and incising are repeated in accordance with the size of the diseased part X. Therefore, the submucosal layer W including the diseased part X is removed from the alimentary tract (refer to FIG. 25).

According to the mucosa separation apparatus and the method for mucosa separation of this embodiment, since the rigidity of the top end 220 of the balloon insertion portion 125 is higher than the lower flexible limit of the rigidity of the wall of the alimentary tract, and is lower than the higher flexible limit of the rigidity of the wall of the alimentary tract, if the operator accidentally pushes the separation balloon insertion device 108 into the channel 2 with a powerful force, the top end 220 is curved, and thereby the force acting on the top end 220 is lost. Therefore, the top end 220 does not pierce the muscularis propria W1.

Further, the force acting on the base end of the balloon insertion portion 125 for pushing the balloon insertion portion 125 into the channel 2 can be transferred to the top end without loss. Therefore, the operability of inserting can be prevented from failing.

Figure 76:
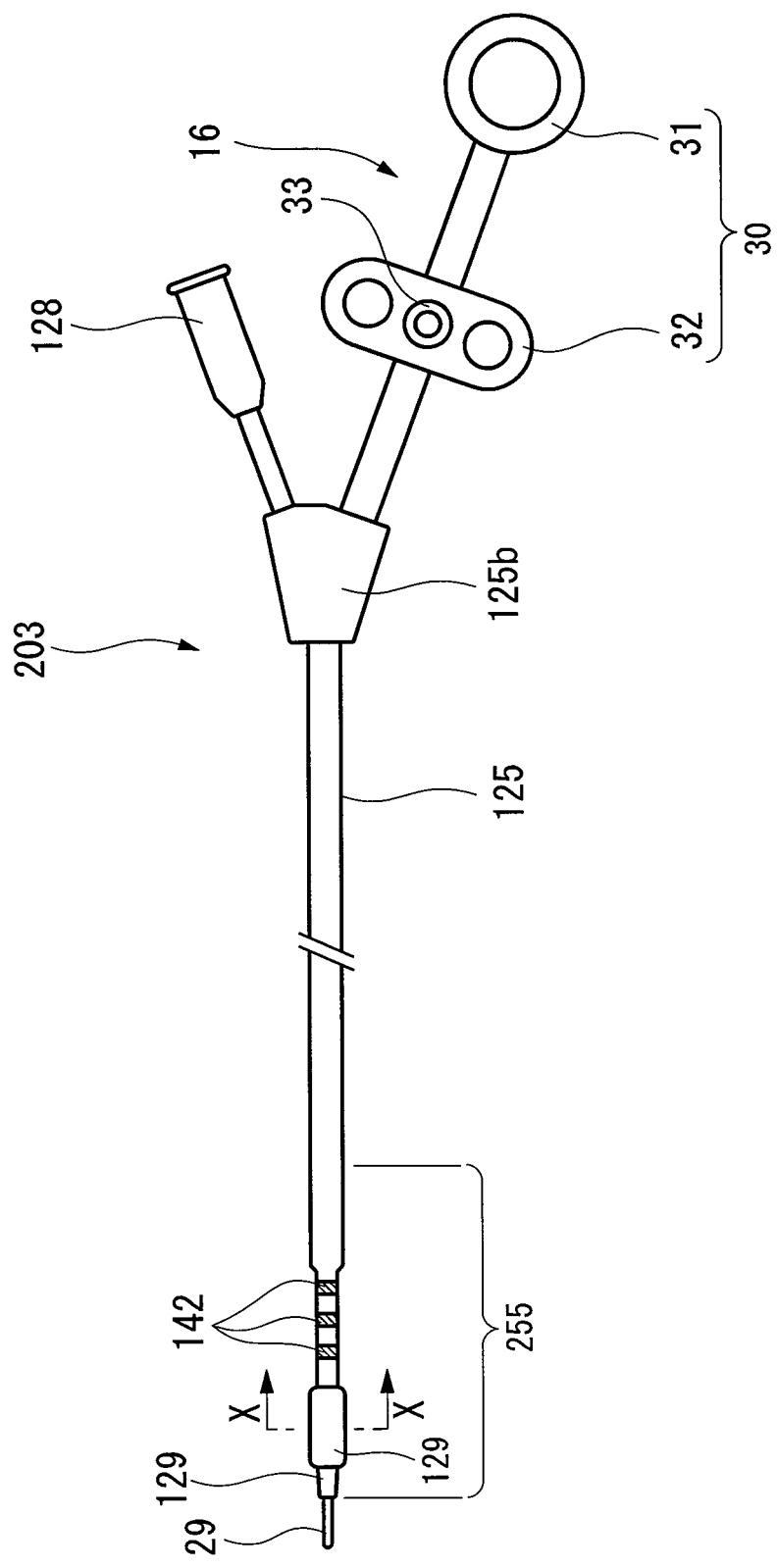
FIG. 76 is a plan view showing the separation balloon insertion device of a sixth embodiment of the present invention.

Next, a sixth embodiment of a mucosa separation apparatus and a method for mucosa separation of the present invention will be explained with reference to FIG. 76 through FIG.

80. Note that, the same descriptive symbols are used for component elements that are the same as those used in the first embodiment and a description thereof is omitted.

Figure 77:
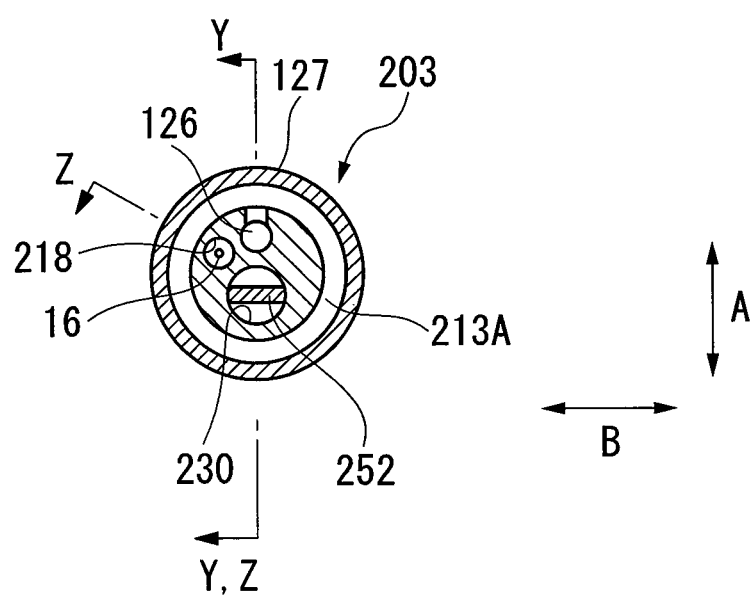
FIG. 77 is a sectional view taken along a line X-X in FIG. 76.
Figure 78:
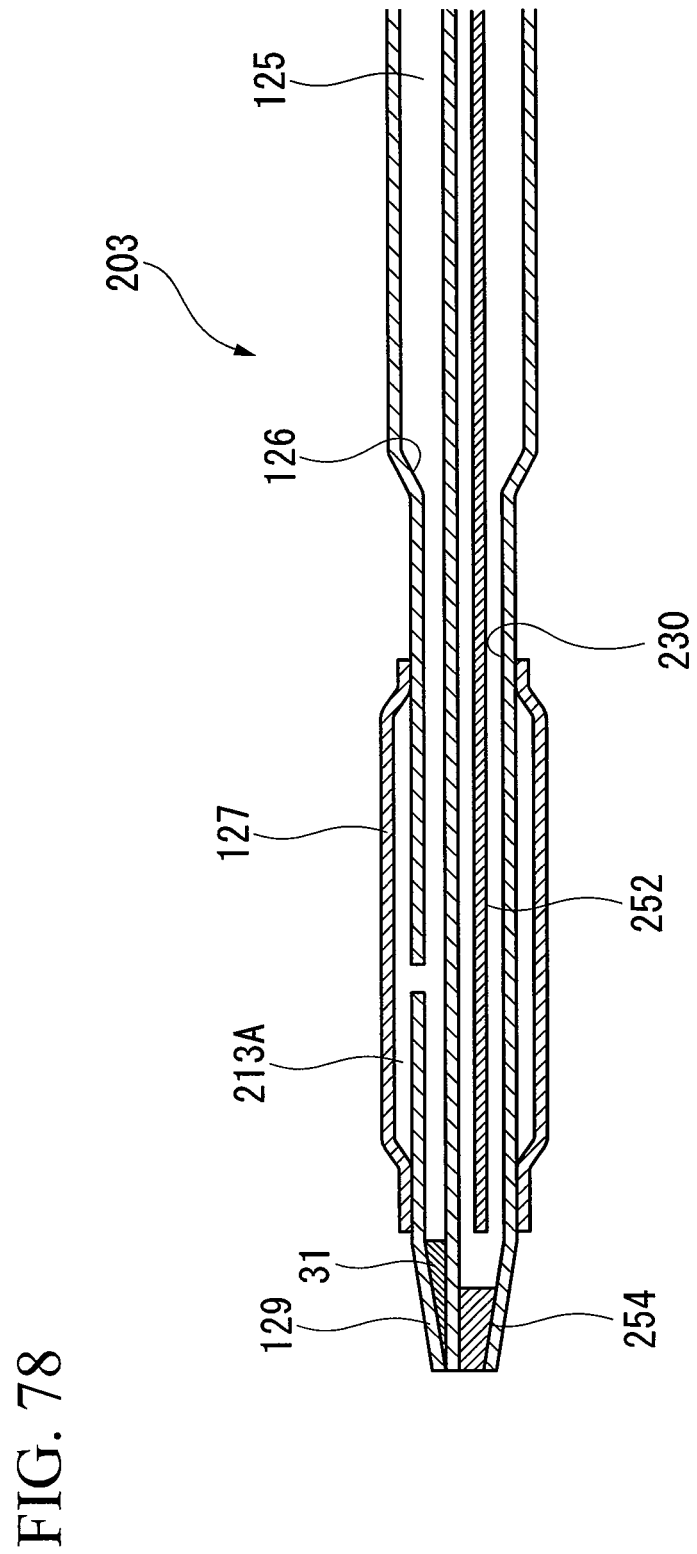
FIG. 78 is a sectional view taken along a line Y-Y in FIG. 77.
Figure 79:
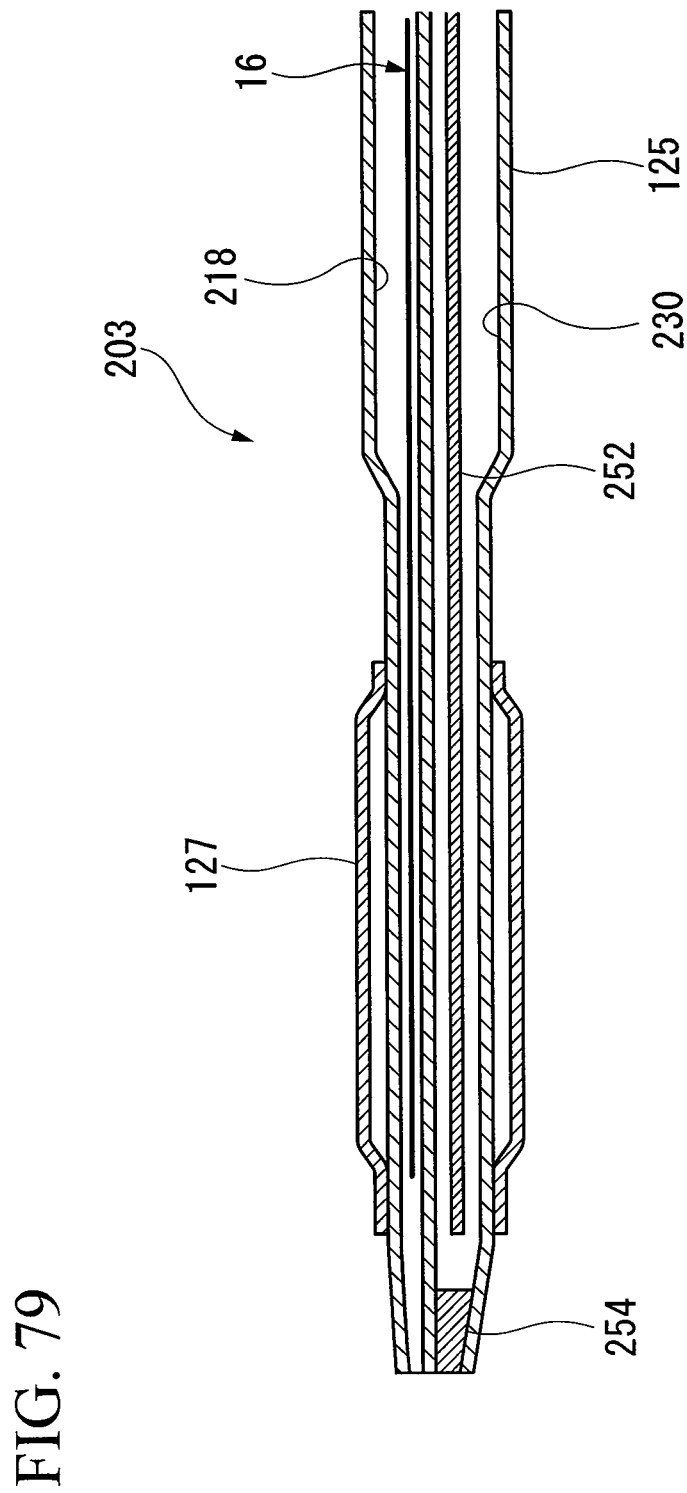
FIG. 79 is a sectional view taken along a line Z-Z in FIG. 77.

A head portion (third flexible portion) of the separation balloon insertion device 203 of the sixth embodiment is formed so as to be longer than the top end 220 of the fifth embodiment. As shown in FIG. 77 through FIG. 79, a plate member 252 is disposed inside the head portion of the balloon insertion portion 125 of the separation balloon insertion device 203. The plate member 252 is made of an elastic material such as metal or plastic, and is formed like a narrow strip piece. The cross-section of the plate member 252 taken along the width direction thereof is formed rectangular. The plate member 252 has the sectional characteristic to incline to be flexible in the thickness direction thereof, and is disposed on the opposite side of the passage 126 across the center of a head portion 255 of the balloon insertion portion 125. In other words, the direction in which the plate member 252 inclines to curve conforms to the direction in which the head portion 255 of the balloon insertion portion 125 must be curved. The length of the plate member 252 is equal to or more than the length of the balloon insertion portion 125 which is protruded from the tip of the insertion portion 3 after inserting the balloon insertion portion 125 into the channel 2 of the endoscope 4.

A channel 230 for inserting the plate member 252 thereinto is formed within the balloon insertion portion 125. The plate member 252 is inserted into the channel 230 from the tip of the balloon insertion portion 125, and is held inside the channel 230 depending on the frictional force between the plate member 252 and an inside wall surface of the channel 230. A sealing member 254 which seals the channel 230 is disposed within the top end of the balloon insertion portion 125.

Since the plate member 252 is disposed within the head portion 255 of the balloon insertion portion 125, the head portion 255 is provided with a property for curving the head portion by uniform curvature when an external force is acted on the head portion. Further, the head portion 255 inclines to curve in the thickness direction (direction A in FIG. 77) of the plate member 252, and inclines to hardly curve the width direction (direction B in FIG. 77) of the plate member 252. The rigidity of the head portion 255 is higher than the lower flexible limit of the rigidity of the wall of the alimentary tract, and is lower than the higher flexible limit of the rigidity of the wall of the alimentary tract.

The method for mucosa separation for removing a diseased part X developing inside an alimentary tract from a submucosal layer W using the separation balloon insertion device 203 as mentioned above will be explained.

The method for mucosa separation of this embodiment includes the steps of inflating, aperture-forming, inserting, length-adjusting (including the step of curving), separating and incising. Each of the steps will be explained.

Figure 80:
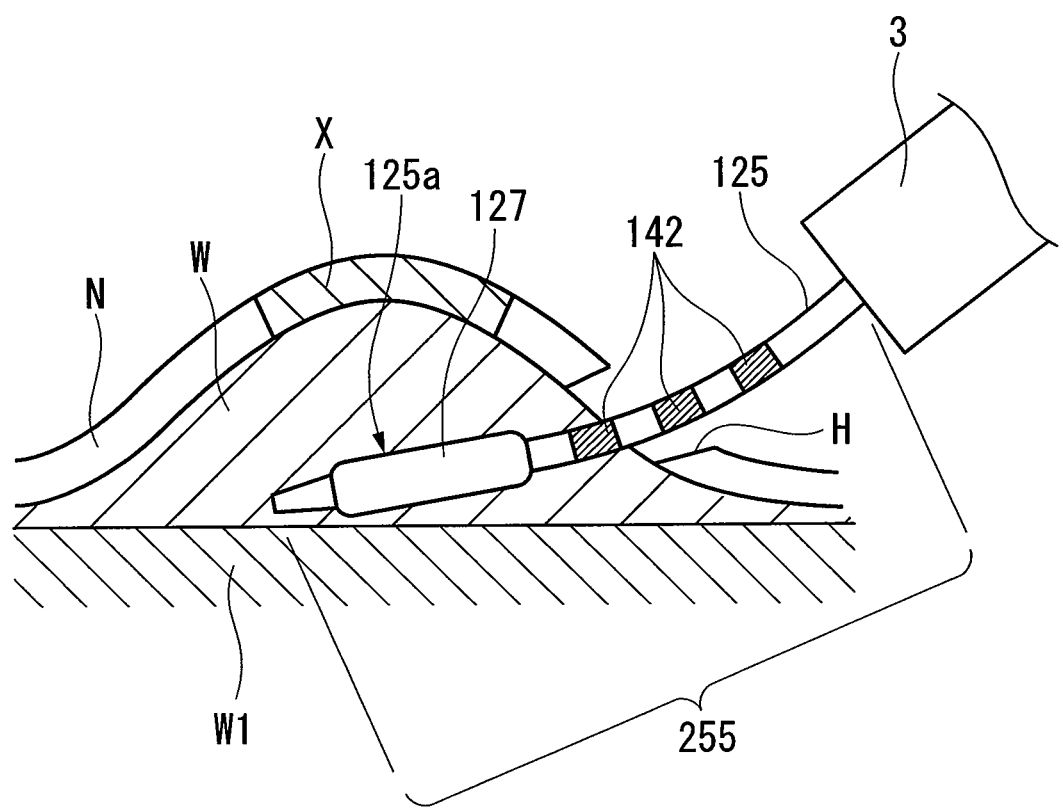
FIG. 80 is a view showing a method for mucosa separation of the sixth embodiment of the present invention, and shows a state where the head portion of the balloon insertion portion is curved by pushing such head portion onto a muscularis propria under the submucosal layer.

First, similar to the fifth embodiment, the step of inflating, the step of aperture-forming and the step of inserting are performed. After that, the step of length-adjusting including the step of curving is performed. At this time, the balloon insertion portion 125 which is protruded from the tip of the insertion portion 3 of the endoscope 4 is rotated around an axis thereof so that the width direction of the plate member 252 disposed within the balloon insertion portion 125 is substantially parallel to the wall surface of the alimentary tract in the vicinity of the diseased part X. Then, the balloon insertion portion 125 is pushed into the submucosal layer W according to the indicators 142 as guides. When the top end 129 of the balloon insertion portion 125 contacts the muscularis propria W1, a reaction force acts on the top end 129 from the wall of the alimentary tract. When the reaction force acts on the top end 129 of the balloon insertion portion 125, as shown in FIG. 80, the head portion 225 is curved by uniform curvature, and then the head portion 125 of the balloon insertion portion 125 becomes to be substantially parallel to the surface of the alimentary tract.

Also, when the operator pushes the separation balloon insertion device 203 into the channel 2 with a weak force, it does not cause problems. However, when the operator accidentally pushes the separation balloon insertion device 203 into the channel 2 with a powerful force, the top end 129 may pierce the muscularis propria W1. Even in this case, since the rigidity of the head portion 255 of the balloon insertion portion 125 is higher than the lower flexible limit of the rigidity of the wall of the alimentary tract, and is lower than the higher flexible limit of the rigidity of the wall of the alimentary tract, if the operator accidentally pushes the separation balloon insertion device 203 into the channel 2 with a powerful force, the top end 129 is curved, and thereby the force acting on the top end 129 is lost. Therefore, the top end 129 does not pierce the muscularis propria W1.

After the step of curving, similar to the fifth embodiment, the step of separating and the step of incising are performed. If further necessary, the steps of length-adjusting (including the step of curving), separating and incising are repeated in accordance with the size of the diseased part X. Therefore, the submucosal layer W including the diseased part X is removed from the alimentary tract.

According to the mucosa separation apparatus and the method for mucosa separation of this embodiment, since the rigidity of the head portion 255 of the balloon insertion portion 125 is higher than the lower flexible limit of the rigidity of the wall of the alimentary tract, and is lower than the higher flexible limit of the rigidity of the wall of the alimentary tract, if the operator accidentally pushes the separation balloon insertion device 125 into the channel 2 with a powerful force, the head portion 255 is curved, and thereby the force acting on the top end 129 is lost. Therefore, the top end 129 does not pierce the muscularis propria W1. Further, when the head portion 255 of the balloon insertion portion 125 is curved, since the head portion 255 becomes to be substantially parallel to the muscularis propria W1, the head portion 255 of the balloon insertion portion 125 can be moved along the muscularis propria W1 in the step of inserting. Therefore, after the head portion 255 of the balloon insertion portion 125 is curved, the head portion 255 can be located at a predetermined position without stopping the insertion of the balloon insertion portion 125.

Since the head portion 255 is provided with a property for curving the head portion by uniform curvature when an external force is acted on the head portion, it is possible to partway make a prediction of the movement of the head portion 255 when the top end 129 of the balloon insertion portion 125 contacts the muscularis propria W1. Therefore, the head portion 255 can be appropriately located at a desired position.

Since the head portion 255 of the balloon insertion portion 125 inclines to curve in a predetermined direction, the arrangement of the balloon insertion portion 125 with respect to the channel 2 is controlled in the step of the inserting, and the curving direction of the head portion 255 of the balloon insertion portion 125 is appropriately adjusted, and thereby the head portion 255 of the balloon insertion portion 125 can be curved so as to be substantially parallel to the muscularis propria W1. Therefore, the top end 129 does not pierce the muscularis propria W1. Further, after the head portion 255 of the balloon insertion portion 125 is curved, the head portion 255 can be located at a predetermined position without stopping the insertion of the balloon insertion portion 125.

In this embodiment, the separation balloon insertion device 108 including the high-frequency knife 16 is used. However, a separation balloon insertion device not having a high-frequency cutting instrument such as the high-frequency knife may be used with a popular high-frequency cutting instrument. Further, three or more channels may be formed in the insertion portion.

Next, a seventh embodiment of a mucosa separation apparatus and a method for mucosa separation of the present invention will be explained with reference to FIG. 81 through FIG. 89. Note that, the same descriptive symbols are used for component elements that are the same as those used in the first embodiment and a description thereof is omitted.

Figure 81:
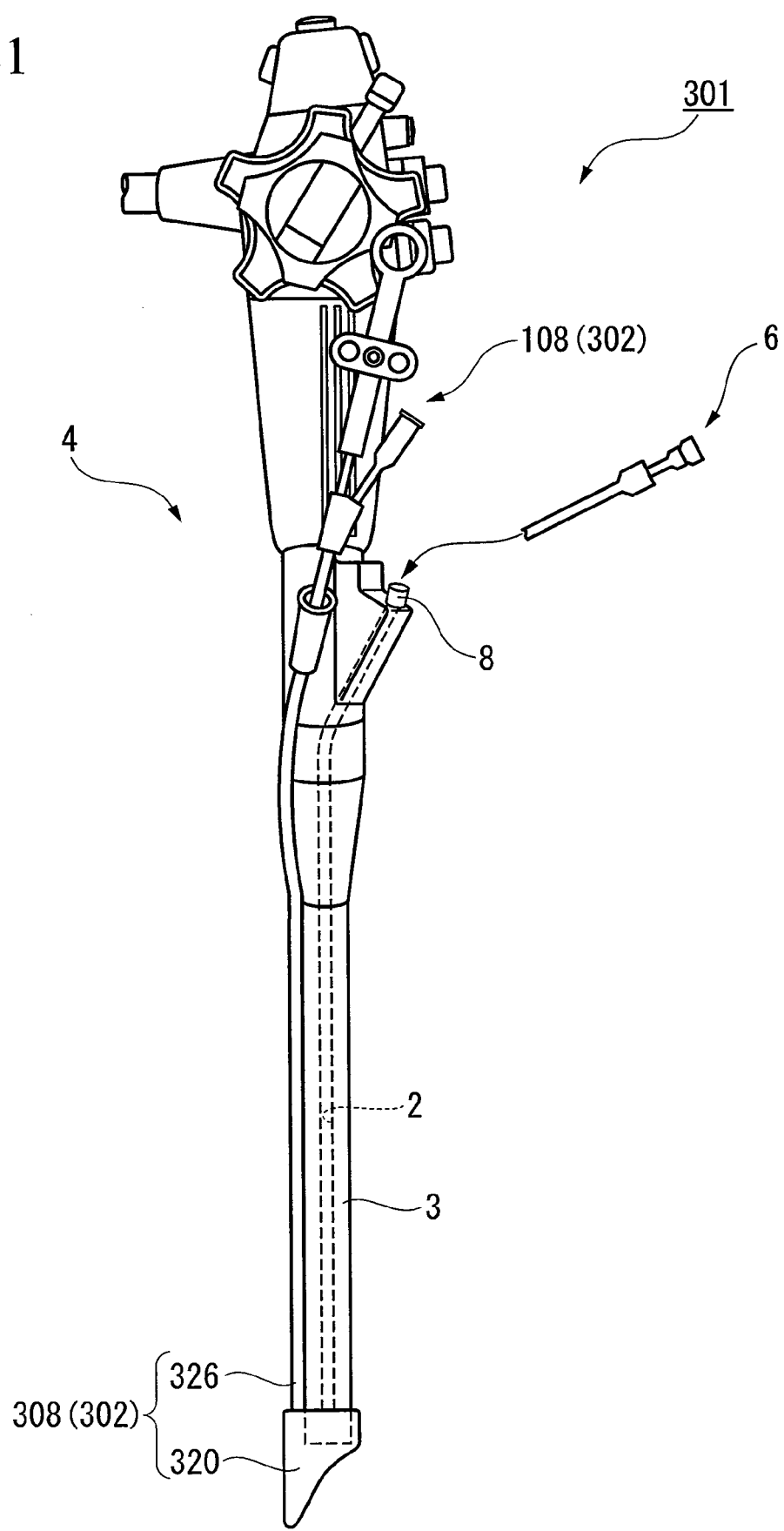
FIG. 81 is a view showing a mucosa separation apparatus of a seventh embodiment of the present invention, and shows a schematic view of a mucosa separation system including the endoscope, an insertion support instrument, the separation balloon insertion device, and the submucosal local injection needle.

As shown in FIG. 81, a mucosa separation system 301 of this embodiment includes the endoscope 4, a separation balloon insertion instrument (mucosa separation apparatus) 302 and the submucosal local injection needle 6. The separation balloon insertion instrument 302 separates the submucosal layer from the muscularis propria, removes the diseased part from the alimentary tract, and is composed of an insertion support instrument 308 and the separation insertion device 108 (refer to FIG. 36). The submucosal local injection needle 6 is inserted into the channel 2 formed in the insertion portion 3 of the endoscope 4 through the sleeve 8 as appropriate.

Figure 82:
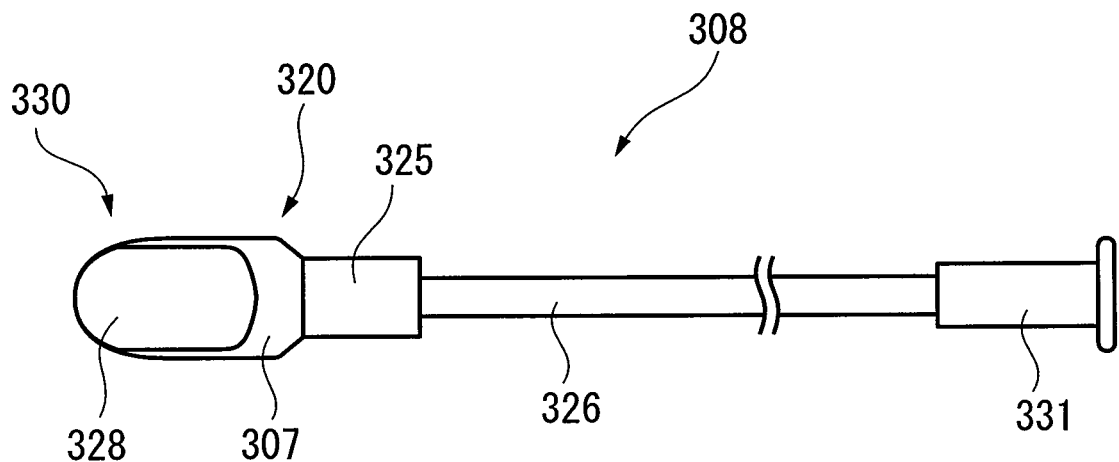
FIG. 82 is a plan view showing the insertion support instrument of the seventh embodiment.
Figure 83:
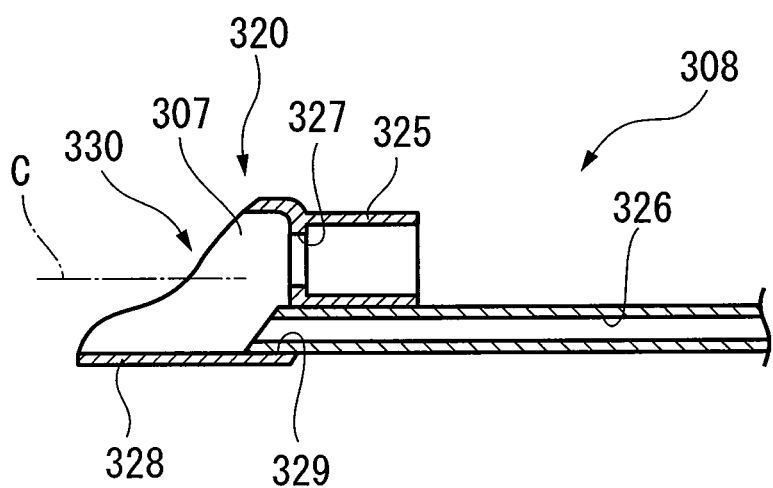
FIG. 83 is a partial sectional view showing the insertion support instrument of the seventh embodiment.

As shown in FIG. 82 and FIG. 83, the insertion support device 308 includes a cap 320 covered with the tip of the insertion portion 3 and an external channel 326 attached to the insertion portion 3 of the endoscope 4. The cap 320 is made of an elastic material, and includes a curving portion 307 which makes the head portion 125a of the balloon insertion portion 125 of the separation balloon insertion portion 108 inserted into the external channel 326 to curve, and a connecting portion 325 into which the tip of the insertion portion 3 is inserted. The curving portion 307 is formed like a cylinder, the connecting portion 325 is disposed at a base portion of the curving portion 307. A through hole 327 which exposes the tip of the insertion portion 3 to the inside of the curving portion 307 when the cap 320 is covered with the tip of the insertion portion 3 is formed between the curving portion 307 and the connecting portion 325. A protruding portion (fourth flexible portion) 328 which deforms when it contacts the wall surface of the hollow organ is formed at the tip of the curving portion 307. An opening 330 of the tip of the curving portion 307 is formed so as to incline with respect to the center axis C of the curving portion 307 by forming the protruding portion 328. Further, a through hole 329 which passes from the outside to the inside of the cap 320 is formed in the cap 320. The tip of the external channel 326 is inserted into the through hole 329 from the outside to the inside of the cap 320.

The external channel 326 is a tube body which is flexible. When the external channel 326 is attached to the endoscope 4, the terminal of the external channel 326 reaches the sleeve 8. An insertion sleeve 331 is made of a material which is harder than the material which forms of the external channel 326 is disposed at the base end of the external channel 326. The external 326 is attached to the endoscope 4 so as to be along the insertion portion 3. The tip of the external channel 326 is inserted into the through hole 329 of the cap 320 covered with the tip of the insertion portion 3.

The method for mucosa separation for removing a diseased part X developing inside an alimentary tract from a submucosal layer W using the mucosa separation system 301 as mentioned above will be explained.

The method for mucosa separation of this embodiment includes the steps of inflating, aperture-forming, inserting, angle-adjusting, length-adjusting, separating and incising. Each of the steps will be explained.

First, similar to the first embodiment, the step of inflating is performed (refer to FIG. 11). After that, the step of aperture-forming is performed. That is, the balloon insertion portion 125 of the separation balloon insertion device 108 is inserted into the external channel 326, and thereafter the head portion 125a of the balloon insertion portion 125 is protruded from the through hole 327 of the cap 320 covered with the tip of insertion portion 3.

After the head portion 125a of the balloon insertion portion 125 is protruded from the tip of insertion portion 3, the knife sliding portion 32 is moved toward the tip of the balloon insertion portion 125, and thereby the knife portion 29 is protruded from the operation tube 21, and is further protruded from the top end 129 of the balloon insertion portion 125. While the condition is held, high-frequency current is supplied to the knife portion 29 from the high-frequency power supply connected to the power supply connection portion 33, the knife portion 29 is moved forward, and thereby an aperture H with a predetermined size is formed in the mucosa N in the vicinity of the diseased part X (refer to FIG. 14). After the aperture H is formed, supplying of high-frequency current is stopped. The sliding portion 25 is moved toward the tip of the balloon insertion portion 10, and thereby the knife portion 29 is retracted into the operation tube 21.

Figure 84:
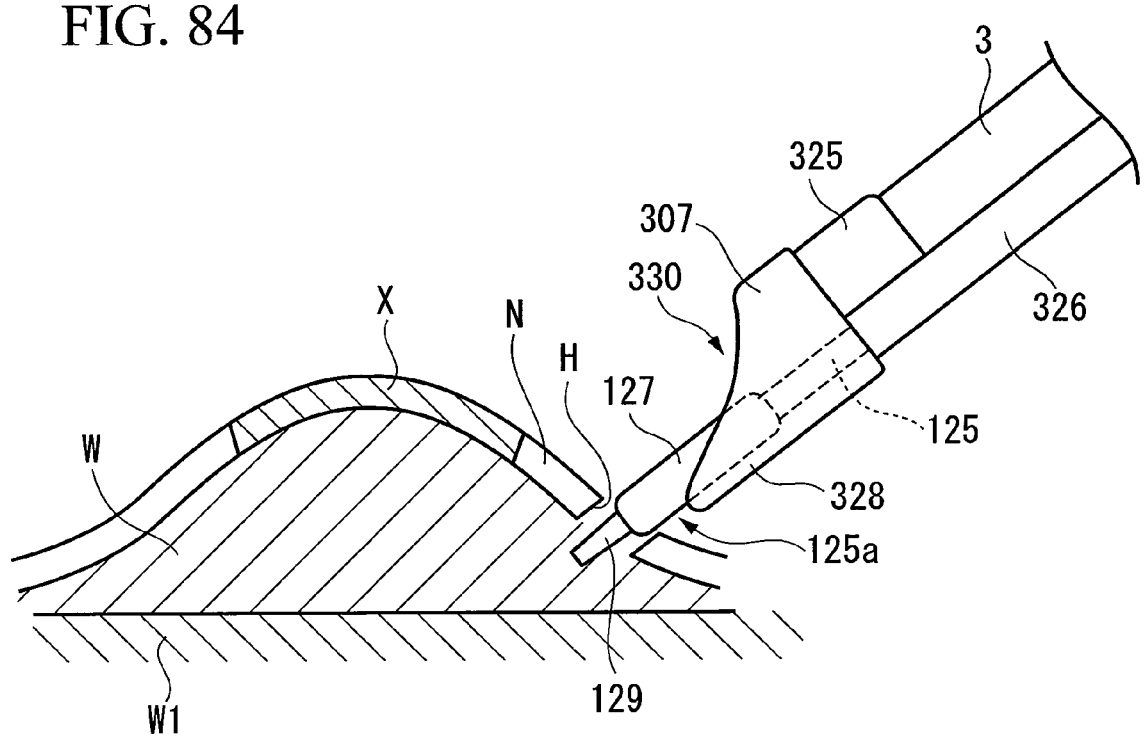
FIG. 84 is a view showing a method for mucosa separation of the seventh embodiment of the present invention, and shows a state where the tip of the balloon insertion portion is inserted into the aperture after forming the aperture in the mucosa.

After the step of aperture-forming, the step of inserting is performed. That is, after the knife portion 29 is retracted, as shown in FIG. 84, only the top end 129 of the balloon insertion portion 125 is inserted into the aperture H.

After the step of inserting, the step of angle-adjusting is performed. That is, the protruding portion 328 of the cap 320 contacts the wall surface of the alimentary tract in the vicinity of the aperture H. At this time, a reaction force is acted on the curving portion 307 of the cap 320 from the wall surface of the alimentary tract. However, since the hardness of the curving portion 307 is configured so that the curving portion 307 deforms in response to the reaction force, the curving portion 307 including the protruding portion 328 is bent along the wall surface of the alimentary tract.

Figure 85:
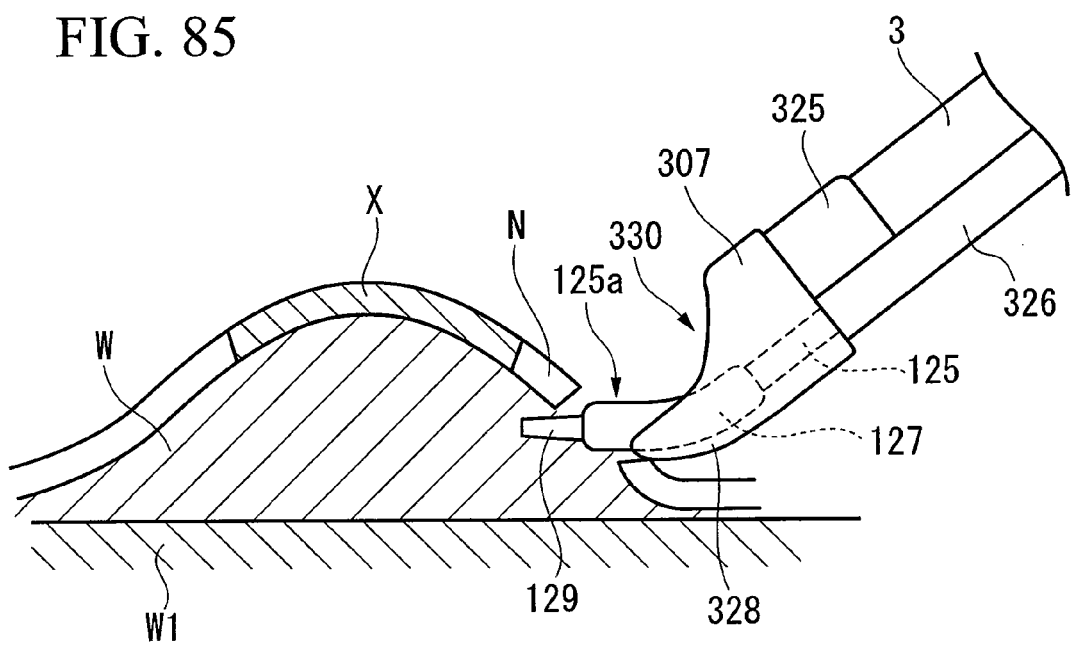
FIG. 85 is a view showing a method for mucosa separation of the seventh embodiment of the present invention, and shows a state where the head portion of the balloon insertion portion is curved after inserting the tip of the balloon insertion portion into the aperture.

Further, since the head portion 125a of the balloon insertion portion 125 inserted into the curving portion 307 is flexible, the head portion 125a is also bent the inner surface of the curving portion 307. Therefore, as shown in FIG. 85, the insertion portion is operated to deform the curving portion 307 until the top end 129 of the balloon insertion portion 125 becomes to be substantially parallel to the muscularis propria W1.

Figure 86:
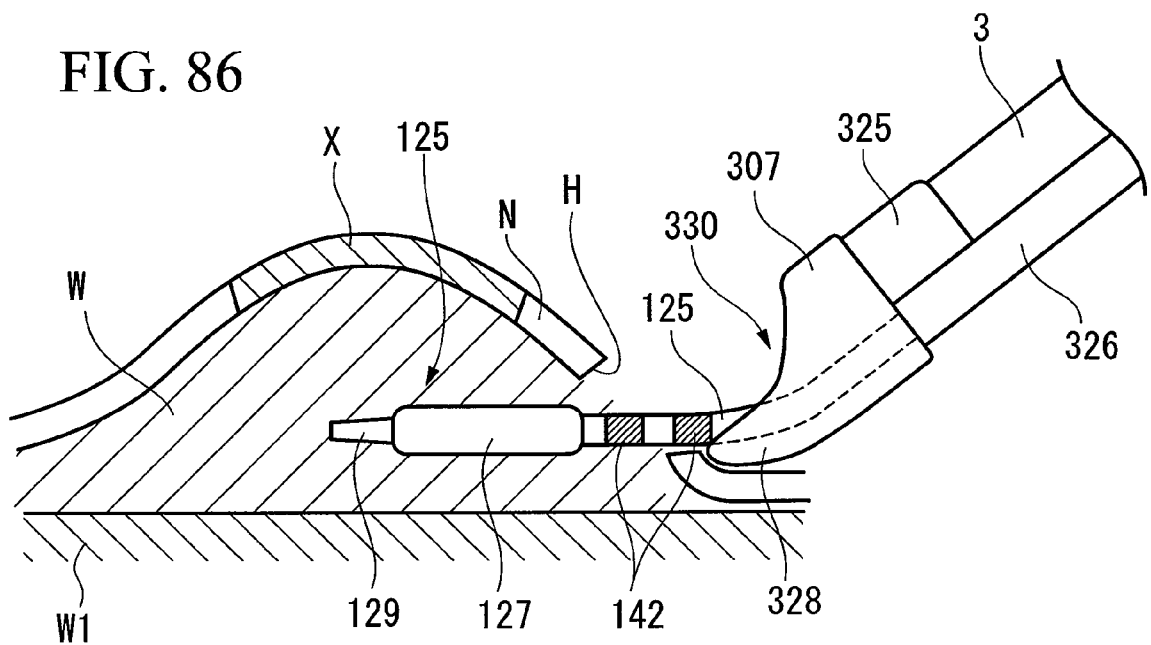
FIG. 86 is a view showing a method for mucosa separation of the seventh embodiment of the present invention, and shows a state where the balloon insertion portion pierces the submucosal layer after curving the head portion of the balloon insertion portion.
Figure 87:
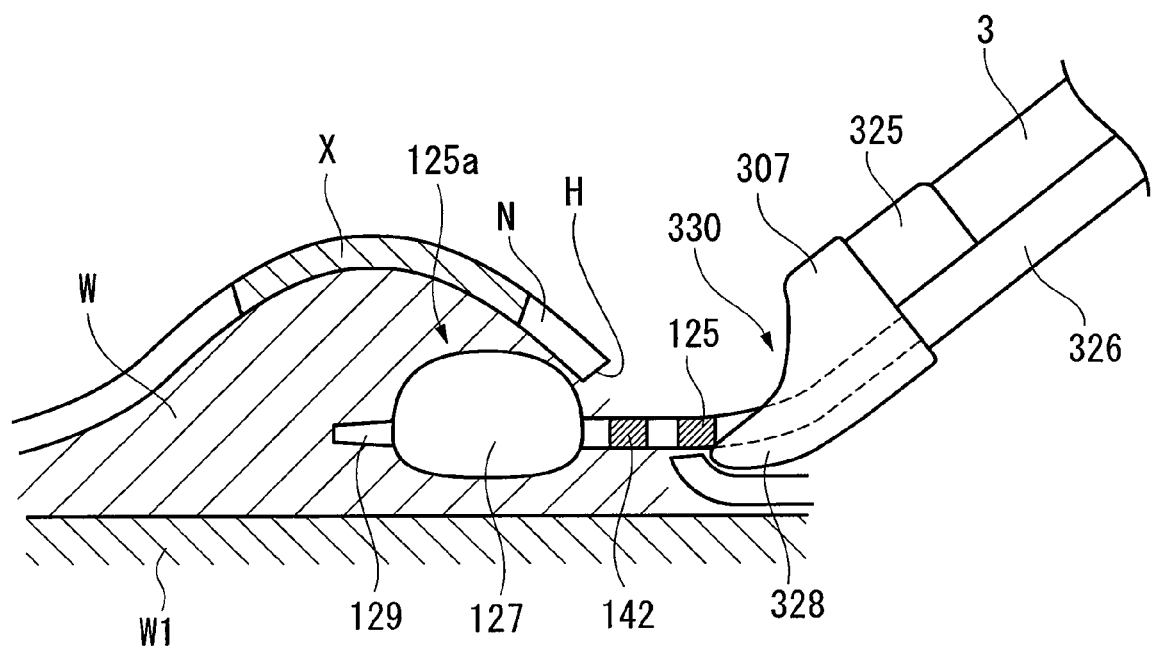
FIG. 87 is a view showing a method for mucosa separation of the seventh embodiment of the present invention, and shows a state where the balloon is expanded within the submucosal layer after piercing the submucosal layer by the balloon insertion portion.

After the step of angle-adjusting, the step of length-adjusting is performed. That is, as shown in FIG. 86, while the curving portion 307 is curved, the balloon insertion portion 125 is moved along a direction being parallel to the surface of the alimentary tract, and thereby the head portion 125a of the balloon insertion portion 125 is pushed into the submucosal layer W through the aperture H, and is positioned at a predetermined position within the submucosal layer W according to the indicators 142 as guides.

After the step of length-adjusting, the step of separating is performed. That is, a fluid is supplied into the passage 126 through the fill port 128 using a syringe (not shown). The fluid supplied into the passage 126 is supplied to the balloon 127 through the communication hole 130, and thereby the balloon 127 is inflated (shown in FIG. 87). Therefore, a part of the submucosal layer W is separated from the muscularis propria W1 existing under the submucosal layer W. After that, the fluid is discharged from the balloon 127 through the fill port 128, and thereby the balloon 127 deflates to its original shape.

Figure 88:
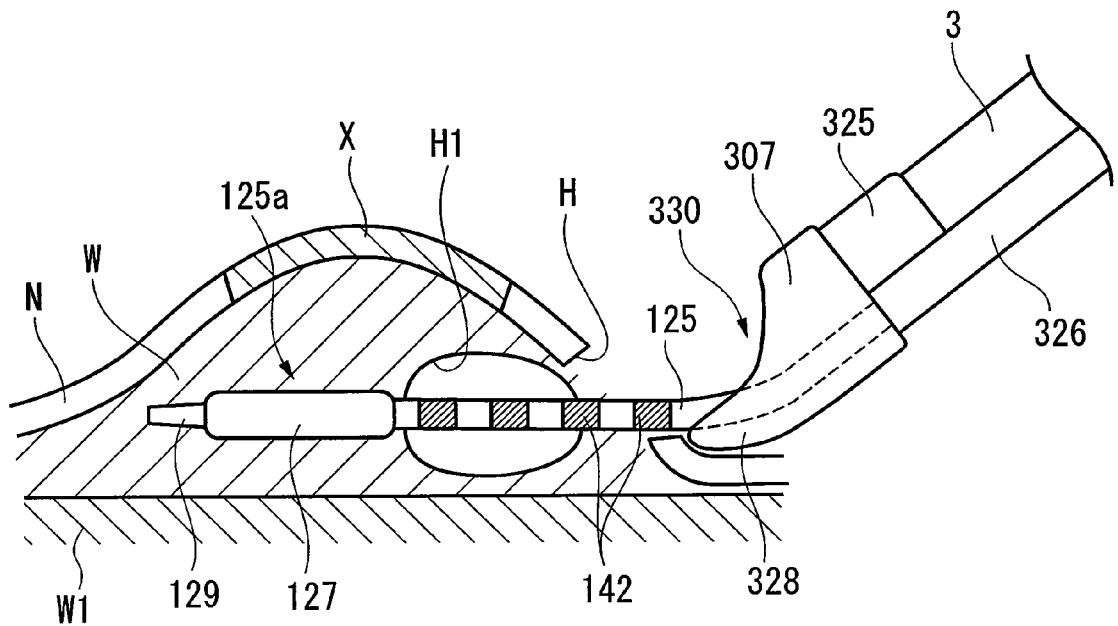
FIG. 88 is a view showing a method for mucosa separation of the seventh embodiment of the present invention, and shows a state where the balloon insertion portion further pierces the submucosal layer after incising of the mucosa around the aperture.
Figure 89:
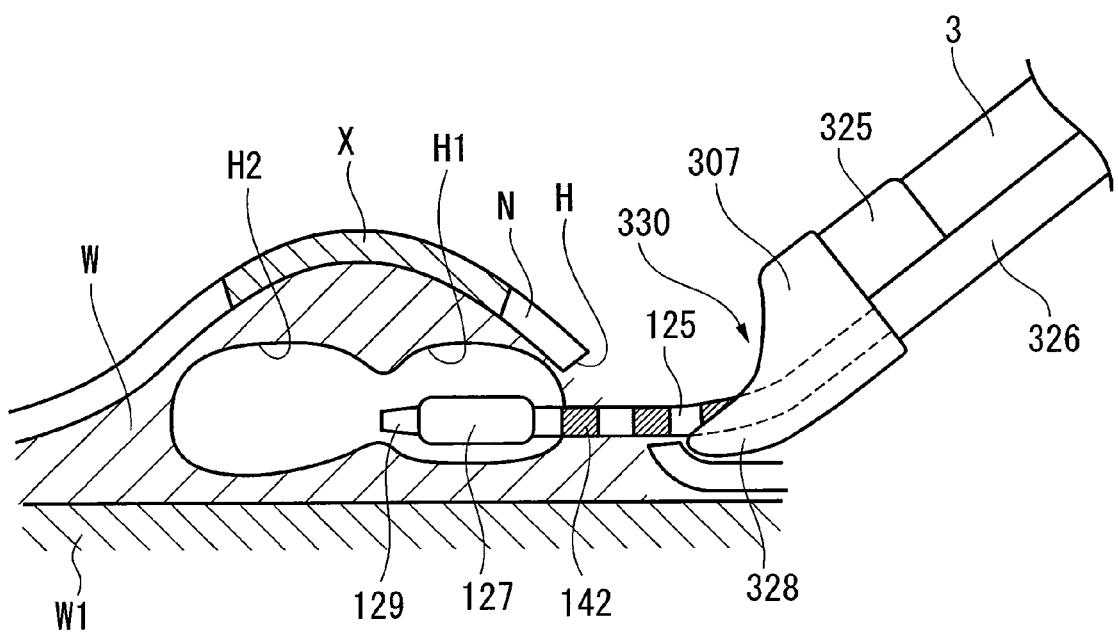
FIG. 89 is a view showing a method for mucosa separation of the seventh embodiment of the present invention, and shows a state where a new cavity is formed within the submucosal layer by re-expanding the balloon after further piercing the submucosal layer by the balloon insertion portion.

As a result, a cavity H1 is formed between the muscularis propria W1 and the submucosal layer W separated from the muscularis propria W1 (refer to FIG. 88).

After the step of separating, the step of incising is performed. That is, the balloon insertion portion 125 is pulled back from the submucosal layer W until the outside of the aperture H. Then, similar to the step of aperture-forming, the knife portion 29 is protruded from the top end 129 of the balloon insertion portion 125, and is inserted into the aperture H (refer to FIG. 20). While the condition is held, high-frequency current is supplied to the knife portion 29, and the knife portion 29 is moved around the diseased part X. Therefore, the mucosa N around the aperture H is incised (refer to FIG. 21). After the mucosa N has been incised with a certain measure of width, supplying of high-frequency current is stopped, and the knife portion 29 is retracted into the operation tube 21.

If it is impossible to separate the mucosa N including the diseased part X from the submucosal layer W by only the cavity H1 because the diseased part X is so large, the steps of length-adjusting, separating and incising are repeated. That is, as shown in FIG. 88, the balloon insertion portion 125 is re-inserted into the submucosal layer W located at back of the cavity H1 through the aperture H according to the indicators 142 as guides. Then, the balloon 127 is inflated, and thereby the submucosal layer W which has not been separated from the muscularis propria W1 at the first step of separating is separated from the muscularis propria W1, and thereby a new cavity H2 is formed. After that, the step of incising is performed again (refer to FIG. 53).

As mentioned above, the steps of length-adjusting, separating and incising are repeated in accordance with the size of the diseased part X. Therefore, the submucosal layer W including the diseased part X is removed from the alimentary tract (refer to FIG. 25).

According to the mucosa separation apparatus and the method for mucosa separation of this embodiment, when the head portion 125a of the balloon insertion portion 125 of the separation balloon insertion device 108 is inserted into the submucosal layer W, the insertion portion 3 is controlled to curve the insertion portion 3, and thereby the force acting on the insertion support instrument 308 for pushing the curving portion 307 to the wall surface of the alimentary tract is adjusted. Therefore, the intensity and the direction of the reaction force acting on the curving portion 307 from the alimentary tract are varied, and thereby the deformation of the curving portion 307 can be controlled. That is, by the curving operation of the insertion portion 3, the insertion angle of the head portion 125a of the balloon insertion portion 125 can be varied. As a result, the balloon insertion portion 125 of the separation balloon insertion device 108 can be reliably inserted into the submucosal layer W through the aperture H without a difficult procedure.

Since the curving portion 307 is disposed at the tip of the insertion support instrument 308, when the balloon insertion portion 125 is inserted into the alimentary tract, it is possible to prevent the curving portion 307 from interfering with the wall of the alimentary tract. Therefore, the insertion support instrument 308 can be inserted into the alimentary tract.

Since the protruding portion 328 is disposed on the curving portion 307 of the insertion support instrument 308, the protruding portion 328 contacts the wall surface of the alimentary tract, and thereby the curving portion 307 can be easily deformed through the protruding portion 328.

Since the insertion support instrument 308 includes the external channel 326 which communicates with the curving portion 307, the separation balloon insertion device 108 is inserted into the external channel 326, and thereby the distance required for protruding the separation balloon insertion device 108 from external channel 326 along the inside surface of the deformed curving portion 307 can be ensured than the case where the separation balloon insertion device 108 is inserted into the channel 2 of the insertion portion 3. Therefore, the head portion 125a of the balloon insertion portion 125 can be inserted into the submucosal layer W so as to be parallel to the muscularis propria W1.

Since another instrument can be inserted into the channel 2 of the insertion portion 3, the replacement frequency of instruments can be reduce, and thereby the burden of a patient can be reduced.

Further, since it is unnecessary to insert two or more instruments into the insertion portion 3 of the endoscope 4, the diameter of the insertion portion can be more downsized than that of an insertion portion of an endoscope of which the insertion portion has two channels. Therefore, the curving operability of the insertion portion 3 can be improved.

When bleeding happens while the mucosa N is separated, and when the bleeding happens with incising of the knife portion 29, the head portion 125a of the balloon insertion portion 125 is close to the bleeding part, and then the balloon 127 is inflated to press the bleeding part. Therefore, the arrest of bleeding can be performed. Further, the knife portion 29 is put onto the bleeding part, and high-frequency current is conducted. Therefore, the arrest of bleeding can be performed by blood clotting.

Next, an eighth embodiment of a mucosa separation apparatus and a method for mucosa separation of the present invention will be explained with reference to FIG. 90 through FIG. 94. Note that, the same descriptive symbols are used for component elements that are the same as those used in the first embodiment and a description thereof is omitted.

Figure 90:
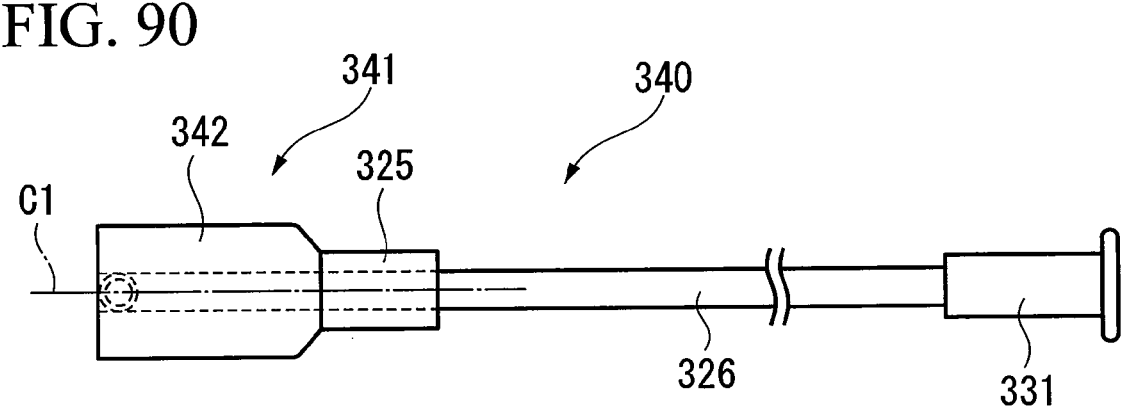
FIG. 90 is a view showing a mucosa separation apparatus of an eighth embodiment of the present invention, and is a plan view of an insertion support instrument.
Figure 91:
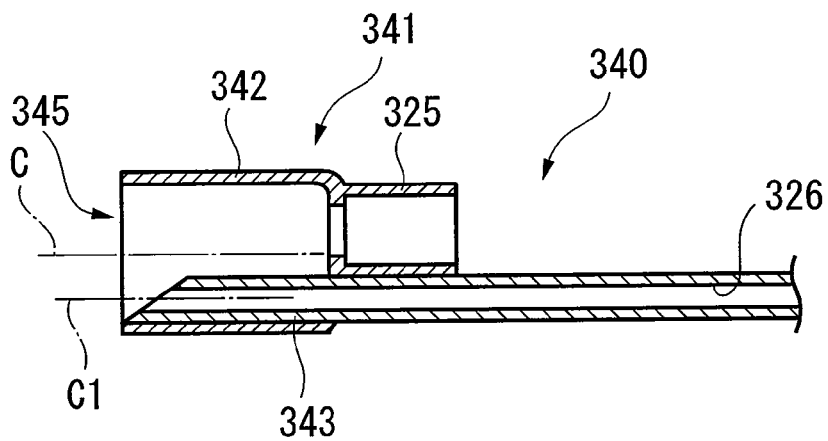
FIG. 91 is a partial sectional view showing the insertion support instrument of the eighth embodiment.

The eighth embodiment is different from the first embodiment in the below respects. That is, as shown in FIG. 90 and FIG. 91, a cap 341 of an insertion support instrument 340 of this embodiment is provided with a guide portion 343 which guides the balloon insertion portion 125 in a predetermined direction with respect to a curving portion 342. The cylindrical guide portion 343 is formed at the tip of the external channel 326 so as to be integrated with the external channel 326, and is attached to the cap 341 so as to be along the inside surface of the curving portion 342. The tip of the guide portion 343 is cut at an angle with respect to the center axis C1 of the guide portion 343 so that the balloon insertion portion 125 guided by the guide portion 343 is protruded from the tip of the guide portion 343 when the curving portion 342 is deformed.

Different from the first embodiment, the curving portion 342 is not provided with the protruding portion 328. An opening 345 is formed so as to be orthogonal to the center axis C of the curving portion 342.

The method for mucosa separation for removing a diseased part X developing inside an alimentary tract from a submucosal layer W using the insertion support instrument 340 as mentioned above will be explained.

The method for mucosa separation of this embodiment includes the steps of inflating, aperture-forming, angle-adjusting, inserting, length-adjusting, separating and incising. Each of the steps will be explained.

Figure 92:
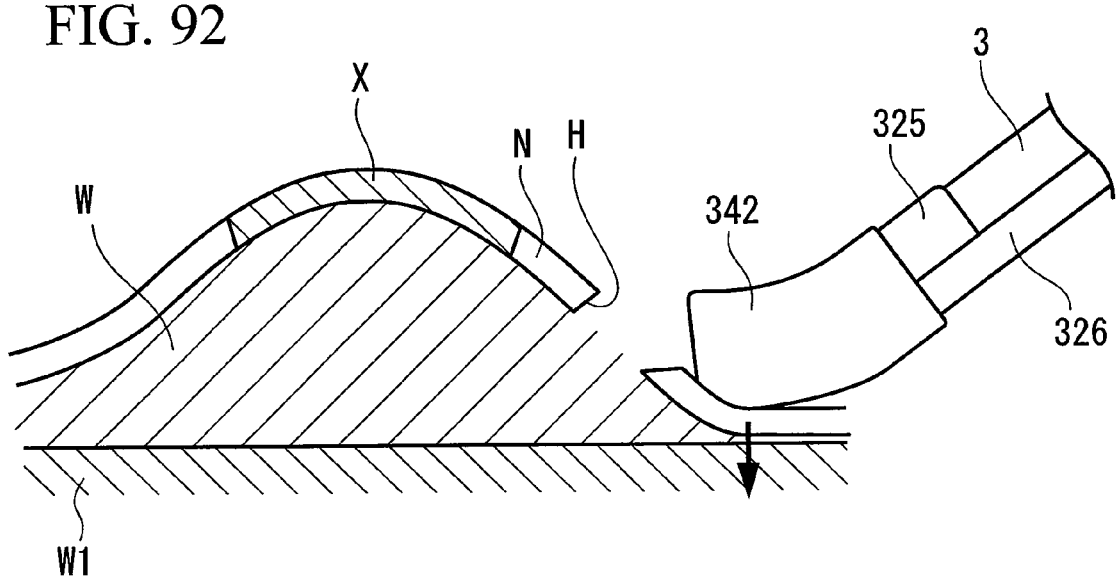
FIG. 92 is a view showing a method for mucosa separation of the eighth embodiment of the present invention, and shows a state where a curving portion is curved by pushing the curving portion onto a wall surface of the alimentary tract after forming the aperture in the mucosa.

First, similar to the seventh embodiment, the steps of inflating and aperture-forming are performed. After that, the step of angle-adjusting is performed. That is, the curving portion 342 of the cap 341 contacts the wall surface of the alimentary tract in the vicinity of the aperture H. At this time, a reaction force acts on the curving portion 342 from the wall surface of the alimentary tract. However, since the hardness of the curving portion 342 is configured so that the curving portion 342 deforms in response to the reaction force, as shown in FIG. 92, the curving portion 342 is bent along the wall surface of the alimentary tract. The guide portion 343 is also bent with the curving portion 342.

Figure 93:
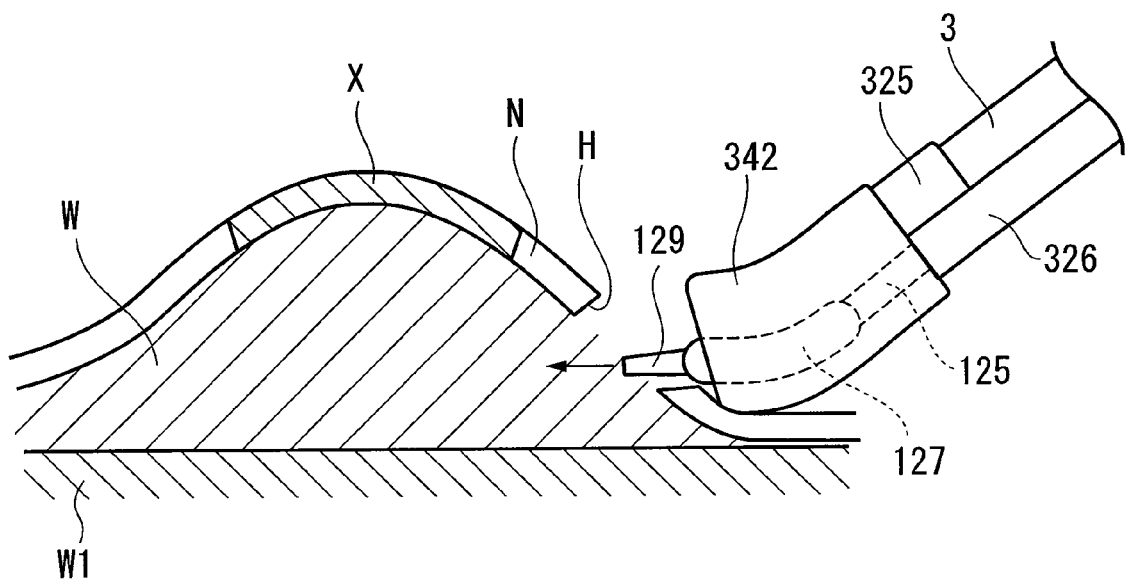
FIG. 93 is a view showing a method for mucosa separation of the eighth embodiment of the present invention, and shows a state where the tip of the balloon insertion portion is inserted into the aperture after curving the curving portion.

After the step of angle-adjusting, the step of inserting is performed. That is, as shown in FIG. 93, the head portion 125a of the balloon insertion portion 125 is inserted into the external channel 326 and the guide portion 343 curved with the curving portion 342, and is protruded from the tip of the insertion portion 3. Then, only the top end 129 of the balloon insertion portion 125 is inserted into the aperture H.

After the step of inserting, similar to the seventh embodiment, the steps of length-adjusting, separating and incising are performed.

Figure 94:
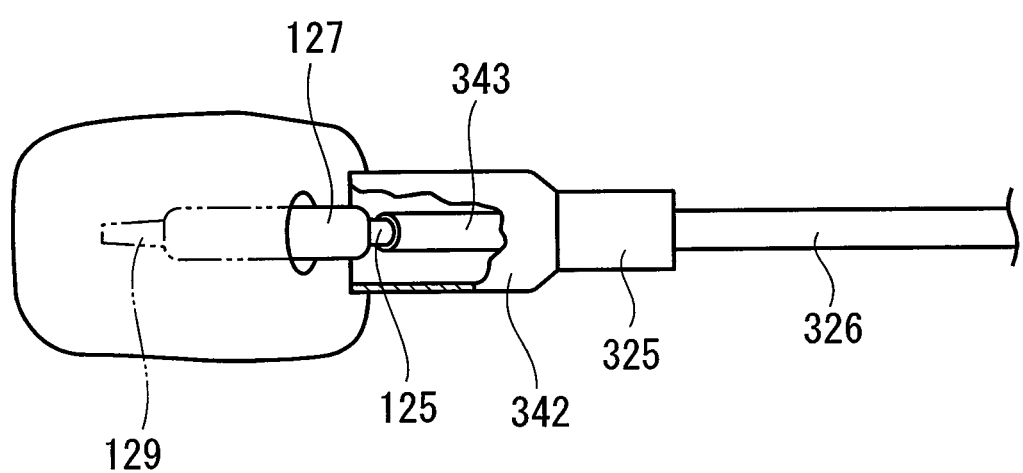
FIG. 94 is a view showing a method for mucosa separation of the eighth embodiment of the present invention, and shows a state where the balloon insertion portion pierces the submucosal layer.

According to the mucosa separation apparatus and the method for mucosa separation of this embodiment, since the guide portion 343 guides the balloon insertion portion 125 in the moving direction of the balloon insertion portion 125, as shown in FIG. 94, it is possible to prevent the balloon insertion portion 125 from deforming unnecessarily. Therefore, the balloon insertion portion 125 moves forwards and backwards smoothly, thus the balloon insertion portion 125 can be reliably inserted into the submucosal layer W.

Figure 95:
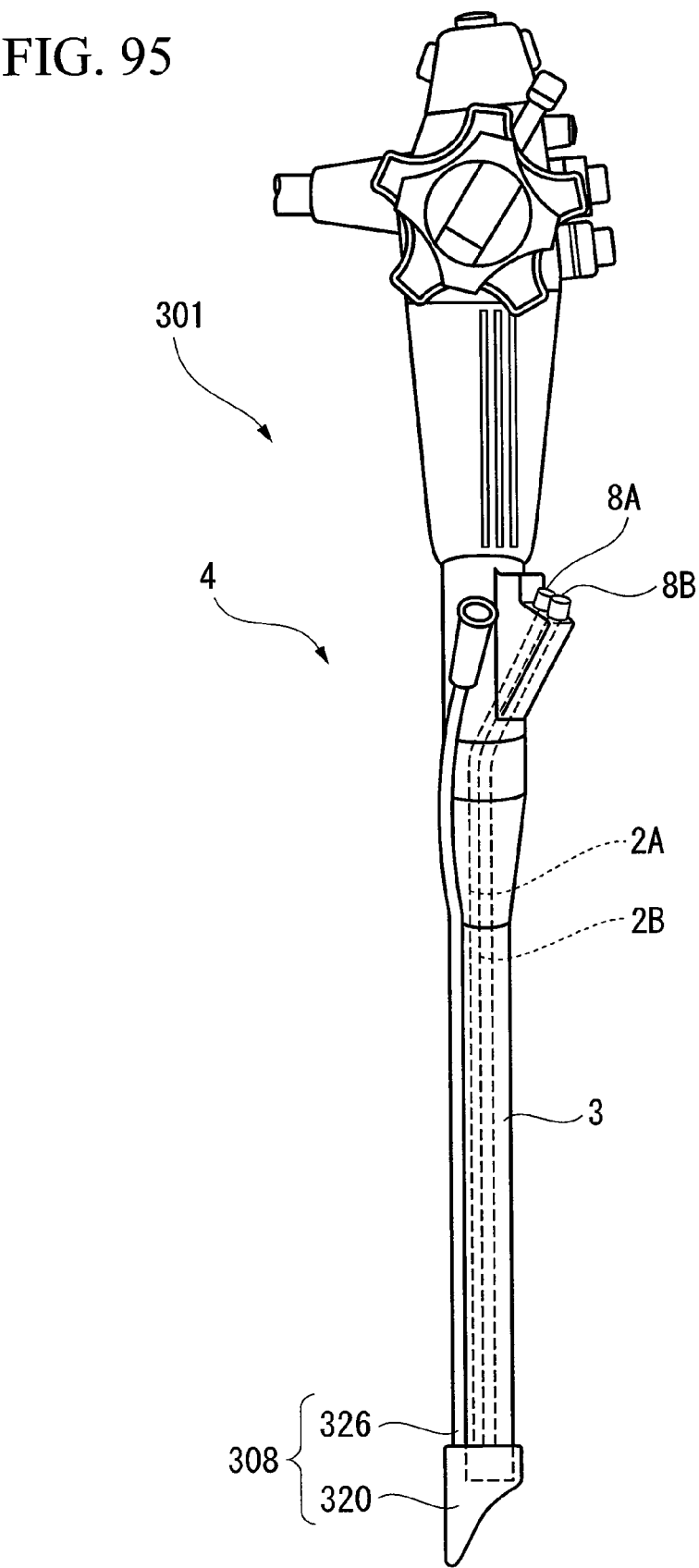
FIG. 95 is a view showing an endoscope and an insertion support instrument of a ninth embodiment of the present invention.
Figure 96:
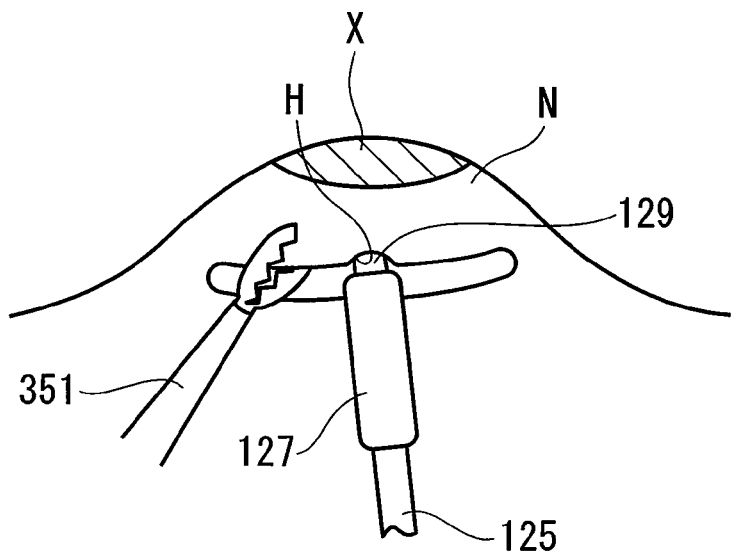
FIG. 96 is a view showing a method for mucosa separation of the ninth embodiment of the present invention, and shows a state where the tip of the balloon insertion portion is inserted into the aperture, while the mucosa is grasped by the grasping forceps.

Next, a ninth embodiment of a mucosa separation apparatus and a method for mucosa separation of the present invention will be explained with reference to FIG. 95 and FIG. 96. Note that, the same descriptive symbols are used for component elements that are the same as those used in the first embodiment and a description thereof is omitted.

The ninth embodiment is different from the first embodiment in the below respects. That is, as shown in FIG. 95, the insertion portion 3 of the endoscope 4 is provided with two channels 2A and 2B. The balloon insertion portion 125 of the separation balloon insertion device 108 is inserted into the channel 2A through a sleeve 8A, and a grasping forceps 351 is inserted into the channel 2B through a sleeve 8B.

Using the endoscope 4 as mentioned above, a diseased part X developing inside an alimentary tract is removed from a submucosal layer W according to the same steps as the first embodiment.

Figure 97:
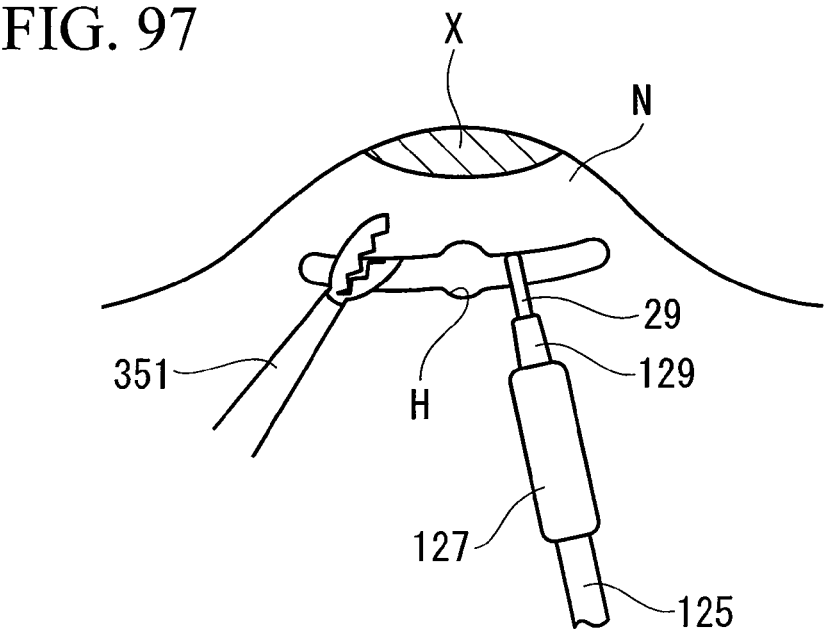
FIG. 97 is a view showing a method for mucosa separation of the ninth embodiment of the present invention, and shows a state where the mucosa around the aperture is incised using the high-frequency knife, while the mucosa is grasped by the grasping forceps.

In the step of inserting, in order to assist with inserting the top end 129 of the balloon insertion portion 125 into the aperture H, as shown in FIG. 97, the mucosa N and the submucosal layer W in the vicinity of the aperture H are grasped by the grasping forceps 351 which is protruded from the tip of the insertion portion 3. Further, in the step of incising, in order to assist with incising the mucosa N by the knife portion 29, as shown in FIG. 96, the mucosa N and the submucosal layer W in the vicinity of the aperture H are grasped by the grasping forceps 351 which is protruded from the tip of the insertion portion 3.

Note that, after the balloon insertion portion 125 of the separation balloon insertion device 108 is inserted into the channel 2A, the submucosal local injection needle 6 and the grasping forceps 351 may be alternatively inserted into the channel 2B.

According to the mucosa separation apparatus and the method for mucosa separation of this embodiment, the balloon insertion portion 125 is inserted into the channel 2A, and the grasping forceps 351 is inserted into the channel 2B. Then, the separation balloon insertion device 108 is used while the mucosa N and the submucosal layer W are grasped by the grasping forceps 351. Thereby, the time for the operations can be shortened. Further, the mucosa N can be reliably incised. Furthermore, since the number of times of replacing instruments is reduced, the burden of a patient can be reduced.

Figure 98:
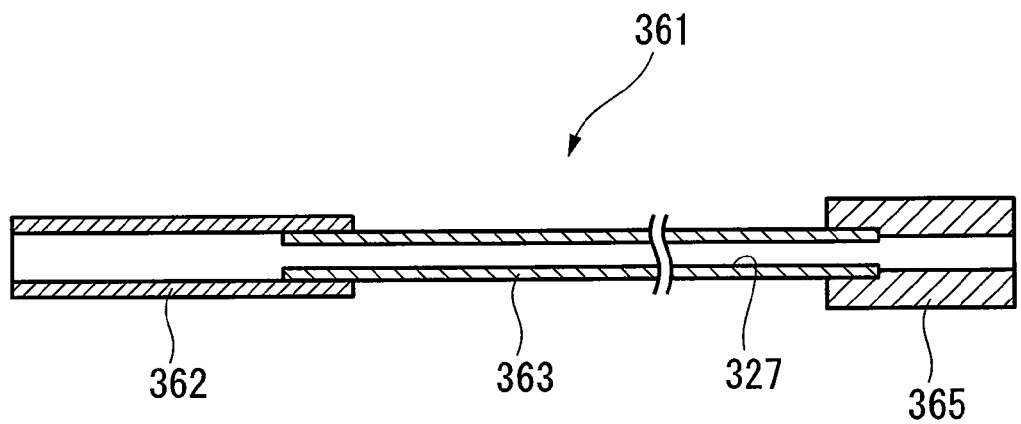
FIG. 98 is a view showing a mucosa separation apparatus of a tenth embodiment of the present invention, and shows a sectional view of an insertion support instrument.
Figure 104:
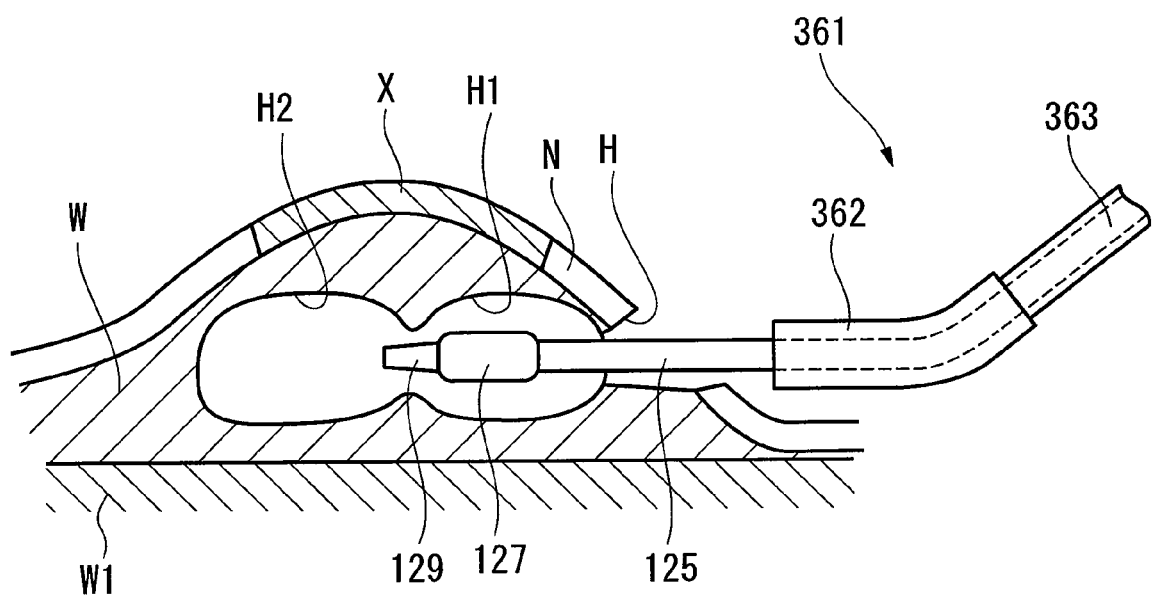
FIG. 104 is a view showing a method for mucosa separation of the tenth embodiment of the present invention, and shows a state where a new cavity is formed within the submucosal layer by re-expanding the balloon after further piercing the submucosal layer by the balloon insertion portion.

Next, a tenth embodiment of a mucosa separation apparatus and a method for mucosa separation of the present invention will be explained with reference to FIG. 98 and FIG. 104. Note that, the same descriptive symbols are used for component elements that are the same as those used in the first embodiment and a description thereof is omitted.

The tenth embodiment is different from the seventh embodiment in below respects. That is, as shown in FIG. 98, a support insertion instrument 361 of this embodiment includes a tubular support portion 363 which is flexible, a cylindrical curving portion 362 disposed at the tip of the support portion 363, and an instrument operation section 365 disposed at the terminal of the support portion 363. The diameter of each of the curving portion 362 and the support portion 363 is configured so that each of the curving portion 362 and the support portion 363 can be inserted into the channel 2.

The support portion 363 is made of a solid material such as polytetrafluoroethylene (PTFE). A through hole 327 formed in the support portion 363 communicates with the inside space of the curing section 362. The internal diameter of the support portion 363 is configured so that the separation balloon insertion device 108 can be inserted into the support portion 363. The curving portion 362 is made of a limber material such as polyethylene (PE), and is adhered with the support portion 363. The internal diameter of the curving portion 362 is sufficiently ensured so that the separation balloon insertion device 108 can be inserted into the curving portion 362 even if the separation balloon insertion device 108 is curved.

The method for mucosa separation for removing a diseased part X developing inside an alimentary tract from a submucosal layer W using the insertion support instrument 361 as mentioned above will be explained.

The method for mucosa separation of this embodiment includes the steps of inflating, aperture-forming, inserting, angle-adjusting, length-adjusting, separating and incising. Each of the steps will be explained.

First, similar to the first embodiment, the step of inflating is performed (refer to FIG. 9). After that, the step of aperture-forming is performed. That is, the submucosal local injection needle 6 is retracted from the channel 2. Then, the insertion support instrument 361 is inserted into the channel 2 instead of the submucosal local injection needle 6, and is protruded from the tip of the insertion portion 3. Further, the balloon insertion portion 125 of the separation balloon insertion device 108 is inserted into the through hole 327 of the insertion support instrument 361 from the side of the instrument operation section 365, and the head portion 125a of the balloon insertion portion 125 is protruded from the tip of the support instrument 361.

After the head portion 125a of the balloon insertion portion 125 is protruded from the tip of the insertion support instrument 361, the knife portion 29 is protruded from the top end 129 of the balloon insertion portion 125. While the condition is held, high-frequency current is supplied to the knife portion 29, the knife portion 29 is moved forward, and thereby an aperture H with a predetermined size is formed in the mucosa N in the vicinity of the diseased part X.

Figure 99:
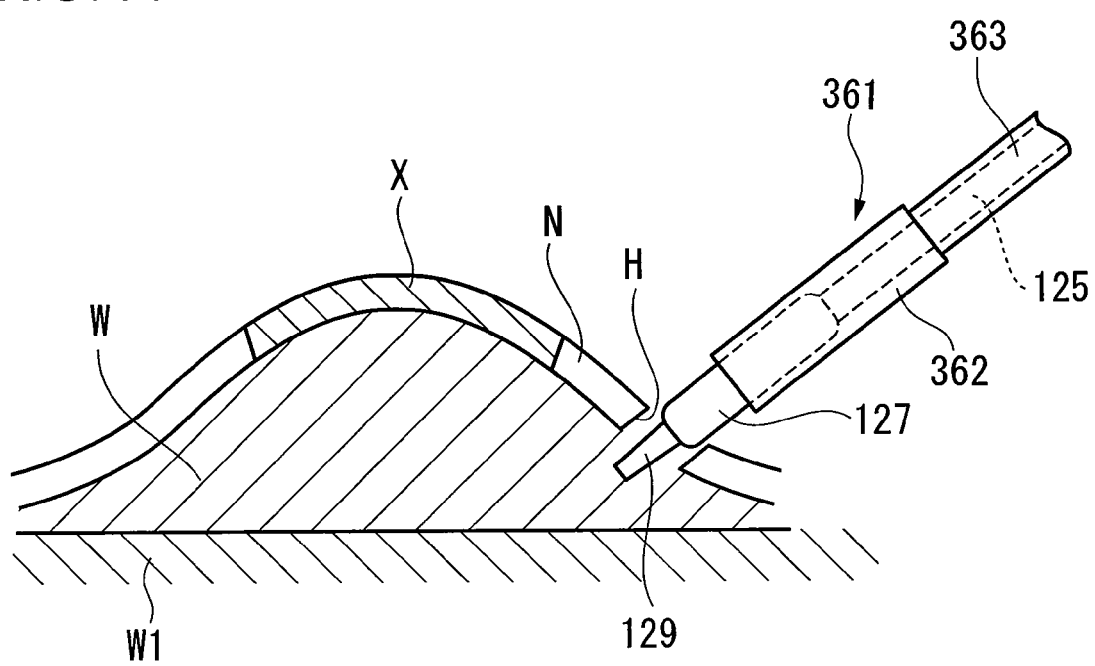
FIG. 99 is a view showing a method for mucosa separation of the tenth embodiment of the present invention, and shows a state where the tip of the balloon insertion portion is inserted into the aperture after forming the aperture in the mucosa.

After the step of aperture-forming, the step of inserting is performed. That is, after the knife portion 29 is retracted, as shown in FIG. 99, only the top end 129 of the balloon insertion portion 125 is inserted into the aperture H.

After the step of inserting, the step of angle-adjusting is performed. That is, the curving portion 362 of the insertion support instrument 361 contacts the wall surface of the alimentary tract in the vicinity of the aperture H. At this time, a reaction force is acted on the curving portion 362 from the wall surface of the alimentary tract. However, since the hardness of the curving portion 362 is configured so that the curving portion 362 deforms in response to the reaction force, the curving portion 362 is bent along the wall surface of the alimentary tract.

Figure 100:
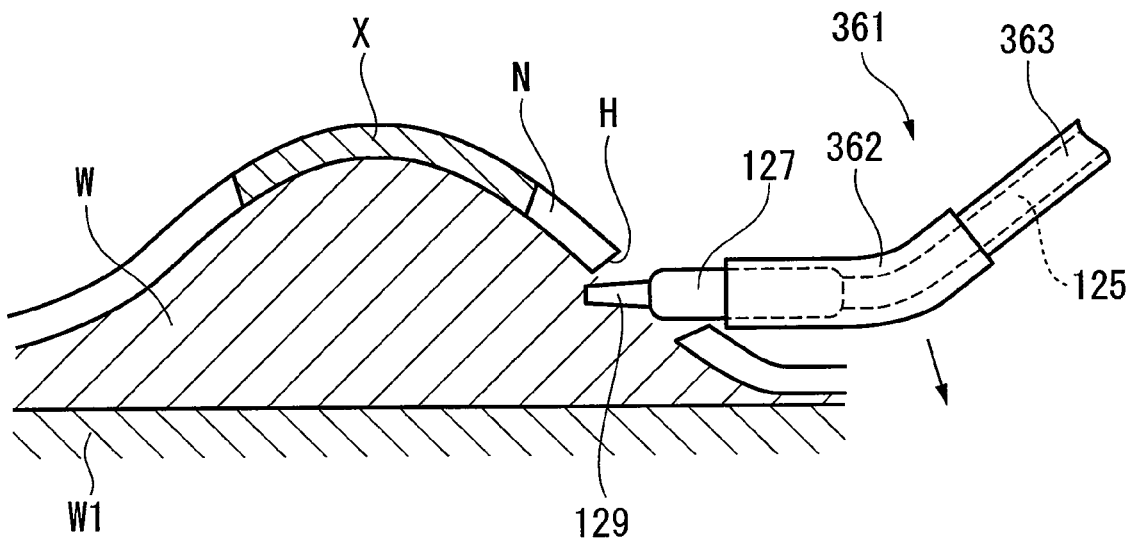
FIG. 100 is a view showing a method for mucosa separation of the tenth embodiment of the present invention, and shows a state where the head portion of the balloon insertion portion is curved after inserting the tip of the balloon insertion portion into the aperture.

Further, since the head portion 125a of the balloon insertion portion 125 inserted into the curving portion 362 is flexible, the head portion 125a is also bent along the inside surface of the curving portion 362. Therefore, as shown in FIG. 100, the insertion portion 3 is operated to deform the curving portion 362 until the top end 129 of the balloon insertion portion 125 becomes to be substantially parallel to the muscularis propria W1.

Figure 101:
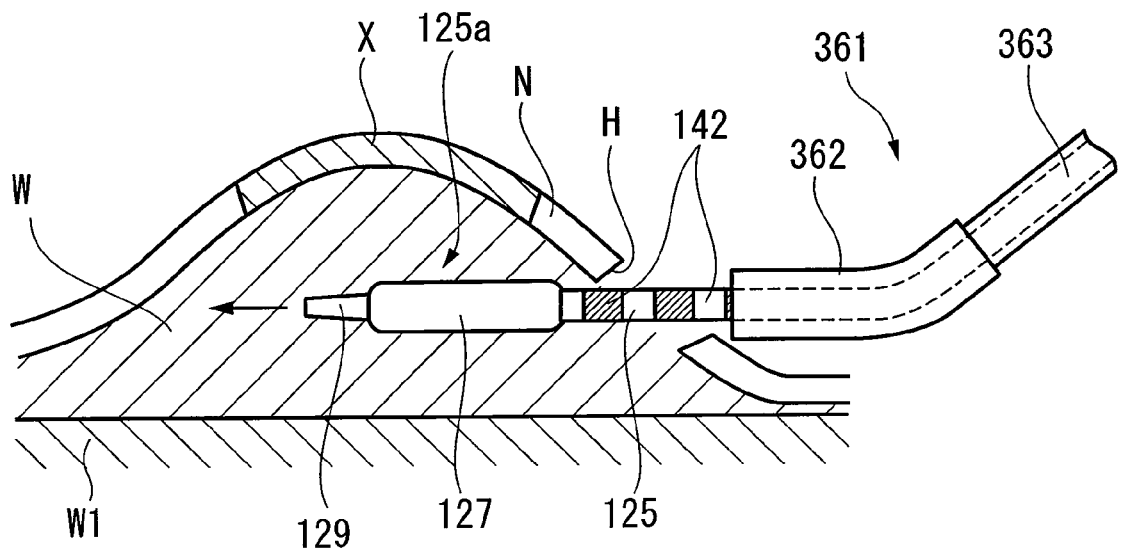
FIG. 101 is a view showing a method for mucosa separation of the tenth embodiment of the present invention, and shows a state where the balloon insertion portion pierces the submucosal layer after curving the head portion of the balloon insertion portion.

After the step of angle-adjusting, the step of length-adjusting is performed. That is, as shown in FIG. 101, while the curving portion 362 is curved, the balloon insertion portion 125 is moved along a direction being parallel to the surface of the alimentary tract, and thereby the head portion 125a of the balloon insertion portion 125 is pushed into the submucosal layer W through the aperture H, and is positioned at a predetermined position within the submucosal layer W according to the indicators 142 as guides.

Figure 102:
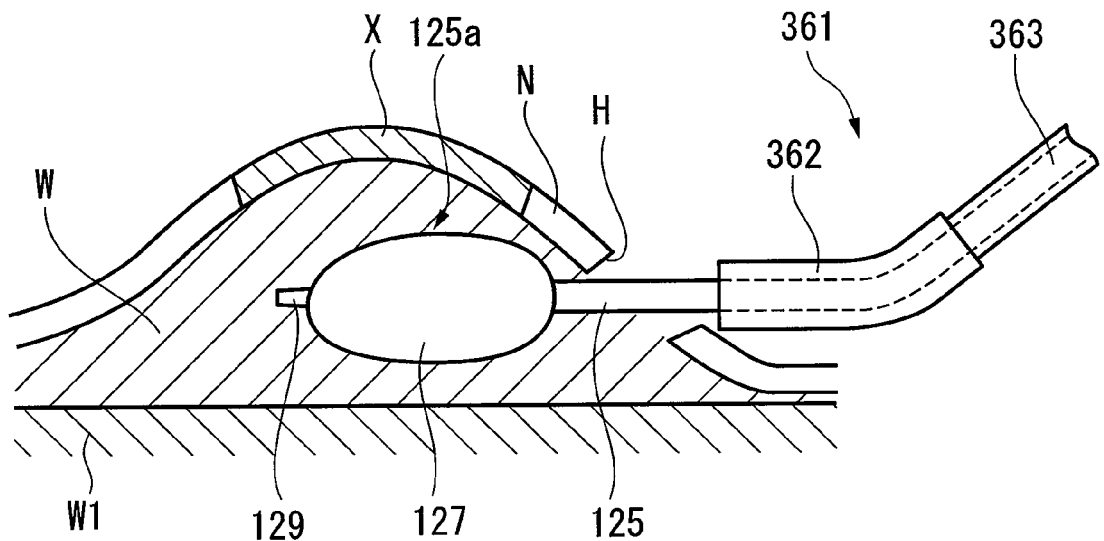
FIG. 102 is a view showing a method for mucosa separation of the tenth embodiment of the present invention, and shows a state where the balloon is expanded within the submucosal layer after piercing the submucosal layer by the balloon insertion portion.
Figure 103:
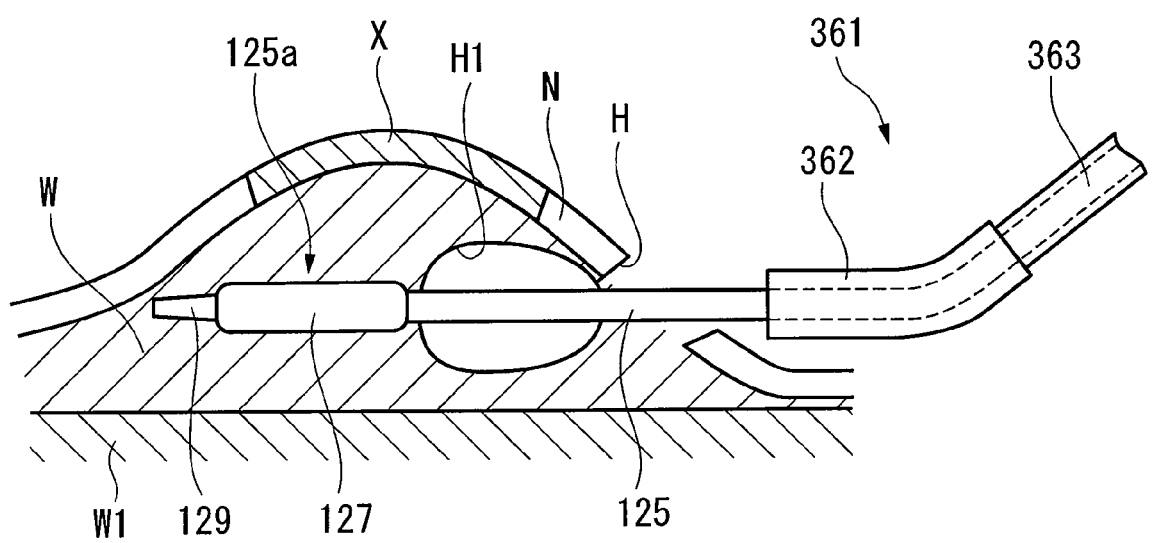
FIG. 103 is a view showing a method for mucosa separation of the tenth embodiment of the present invention, and shows a state where the balloon insertion portion further pierces the submucosal layer after incising the mucosa around the aperture.

After the step of length-adjusting, the step of separating is performed. That is, a fluid is supplied into the passage 126 through the fill port 128 using a syringe (not shown). The fluid supplied into the passage 126 is supplied to the balloon 127 through the communication hole 130, and thereby, as shown in FIG. 102, the balloon 127 is inflated. Therefore, a part of the submucosal layer W is separated from the muscularis propria W1 existing under the submucosal layer W. After that, the fluid is discharged from the balloon 127 through the fill port 128, and thereby the balloon 127 deflates to its original shape. As a result, a cavity H1 is formed between the muscularis propria W1 and the submucosal layer W separated from the muscularis propria W1 (refer to FIG. 103).

After the step of separating, the step of incising is performed. That is, while the knife portion 29 is moved around the diseased part X, the mucosa N around the aperture H is incised using the knife portion 29. After the mucosa N has been incised with a certain measure of width, supplying of high-frequency current is stopped, and the knife portion 29 is retracted into the operation tube 21.

If it is impossible to separate the mucosa N including the diseased part X from the submucosal layer W by only the cavity H1 because the diseased part X is so large, the steps of length-adjusting, separating and incising are repeated. That is, the balloon insertion portion 125 is re-inserted into the submucosal layer W located at back of the cavity H1 through the aperture H according to the indicators 142 as guides. Then, the balloon 127 is inflated, and thereby the submucosal layer W which has not been separated from the muscularis propria W1 in the first step of separating is separated from the muscularis propria W1, and thereby a new cavity H2 is formed. After that, the step of incising is performed again (refer to FIG. 53).

As mentioned above, the steps of length-adjusting, separating and incising are repeated in accordance with the size of the diseased part X. Therefore, the submucosal layer W including the diseased part X is removed from the alimentary tract (refer to FIG. 25).

According to the mucosa separation apparatus and the method for mucosa separation of this embodiment, the support portion 363 is inserted into the channel 2 of the endoscope 4, and thereby the insertion support instrument 361 is easily supported by the insertion portion 3. Further, the insertion support instrument 361 is inserted into the channel 2 of the insertion portion 3 with the separation balloon insertion device 108, rather than the outside of the insertion portion 3, and thereby the outside surface of the insertion portion 3 is not uneven but smooth. Therefore, the insertion portion 3 can be easily inserted into the body cavity.

Figure 105:
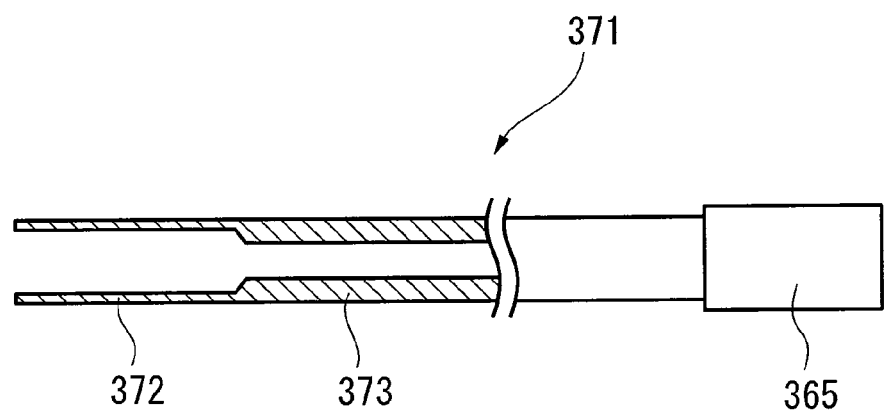
FIG. 105 is a view showing a mucosa separation apparatus of an eleventh embodiment of the present invention, and shows a partial sectional view of an insertion support instrument.

Next, an eleventh embodiment of a mucosa separation apparatus and a method for mucosa separation of the present invention will be explained with reference to FIG. 105 and FIG. 107. Note that, the same descriptive symbols are used for component elements that are the same as those used in the first embodiment and a description thereof is omitted.

The eleventh embodiment is different from the tenth embodiment in the below respects. That is, as shown in FIG. 105, a curving portion 372 of an insertion support instrument 371 of this embodiment is formed so as to be integrated with a support portion 373. The thickness of a tubular wall of the support portion 373 is thicker than that of a tubular wall of the curving portion 372. Therefore, the rigidity of the support portion 373 is greater than that of the curving portion 372.

The method for mucosa separation for removing a diseased part X developing inside an alimentary tract from a submucosal layer W using the insertion support instrument 371 as mentioned above will be explained.

Figure 106:
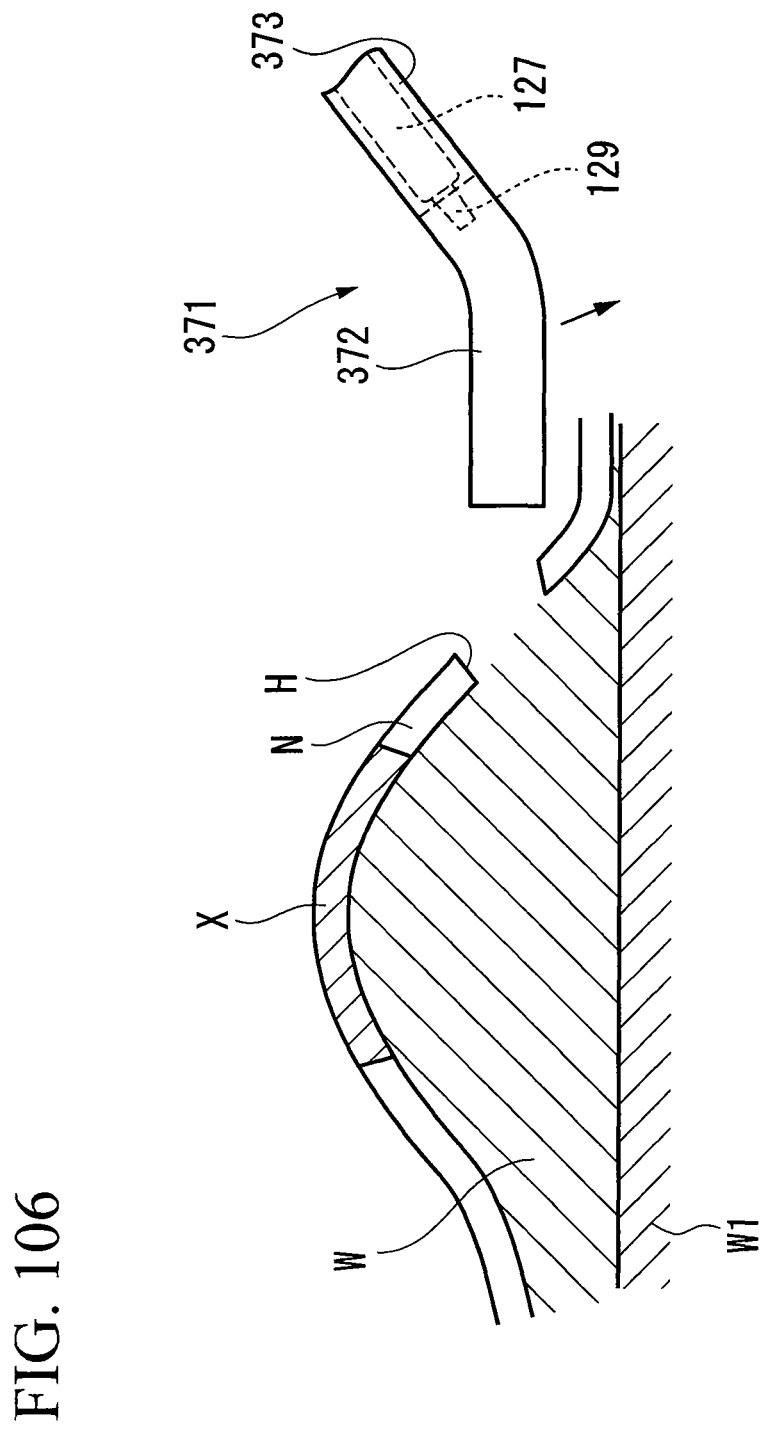
FIG. 106 is a view showing a method for mucosa separation of the eleventh embodiment of the present invention, and shows a state where the curving portion is curved by pushing the curving portion onto the wall surface of the alimentary tract after forming the aperture in the mucosa.

In the method for mucosa separation of this embodiment, differently from the tenth embodiment, after the step of aperture-forming, the step of angle-adjusting is performed, and then the step of inserting is performed. That is, in the step of angle-adjusting, the curving portion 372 of the insertion support instrument 371 contacts the wall surface of the alimentary tract in the vicinity of the aperture H. Therefore, as shown in FIG. 106, the curving portion 362 is bent along the wall surface of the alimentary tract.

Figure 107:
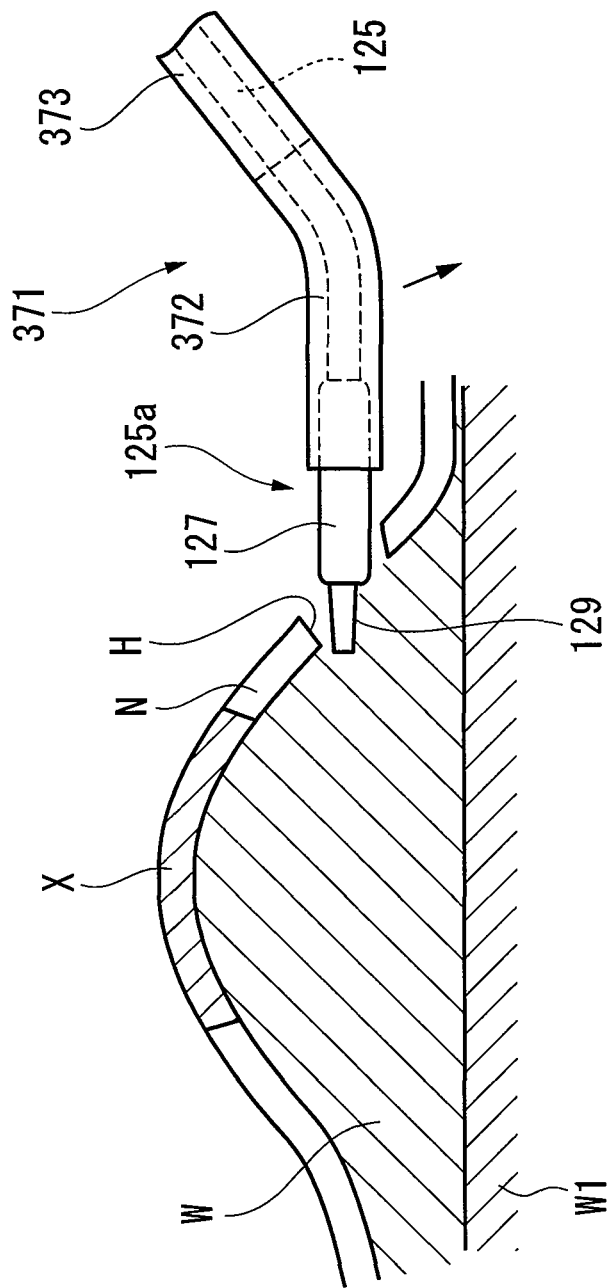
FIG. 107 is a view showing a method for mucosa separation of the eleventh embodiment of the present invention, and shows a state where the tip of the balloon insertion portion is inserted into the aperture after curving the curving portion.

After that, as shown in FIG. 107, the balloon insertion portion 125 is protruded from the tip of the insertion support instrument 371, and then only the top end 129 of the balloon insertion portion 125 is inserted into the aperture H.

The other steps are performed as with the tenth embodiment. Therefore, effects similar to the tenth embodiment can be obtained by the mucosa separation apparatus and the method for mucosa separation of the present embodiment.

In addition, since the curving portion 372 is formed so as to be integrated with the support portion 373, production costs for the apparatus can be saved.

Figure 108:
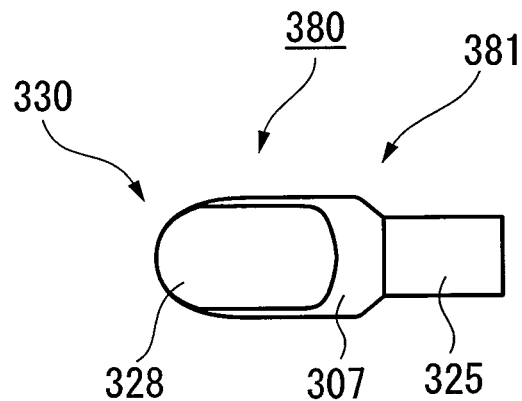
FIG. 108 is a schematic view showing a modification of the insertion support instrument being included in the mucosa separation apparatus of the present invention.
Figure 109:
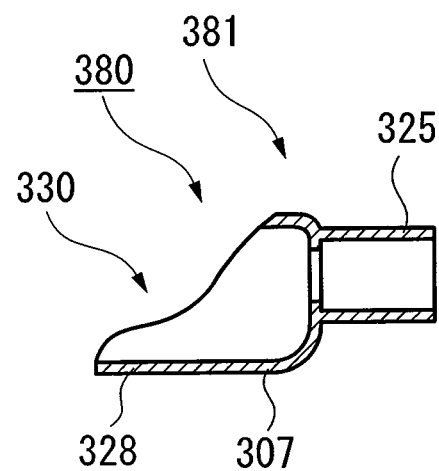
FIG. 109 is a sectional view showing the insertion support instrument in FIG. 108.

In the seventh embodiment, the insertion support instrument 308 includes the external channel 326. However, as shown in FIG. 108 and FIG. 109, an insertion support instrument 380 may be configured with only a cap 381 covered with the tip of the insertion portion 3. The cap 381 includes the curving portion 307 which makes the head portion 125a of the balloon insertion portion 125 of the separation balloon insertion device 108 inserted into the channel 2 of the insertion portion 3 of the endoscope 4 to curve, and the connecting portion 325 into which the insertion portion 3 is inserted. In this case, the separation balloon insertion device 108 is inserted into the channel 2. Therefore, effects similar to the seventh embodiment can be obtained.

Figure 110:
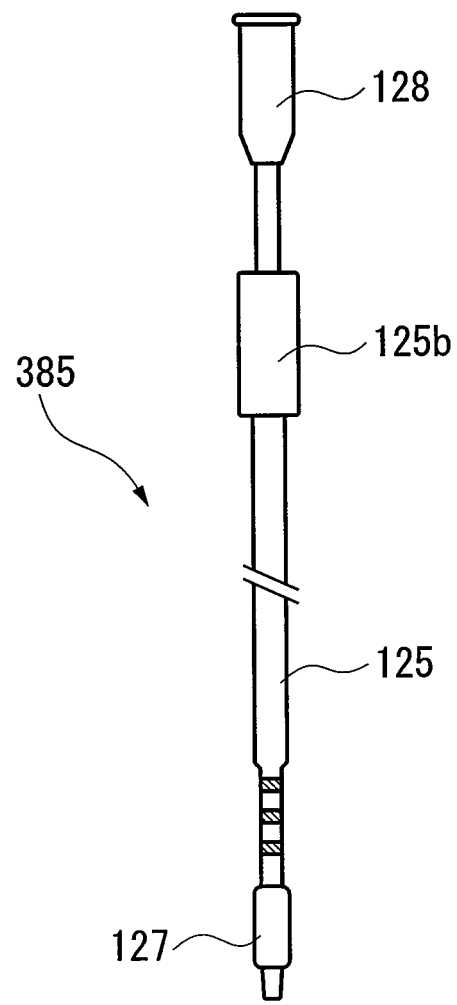
FIG. 110 is a schematic view showing a modification of the separation balloon insertion device being included in the mucosa separation apparatus of the present invention.

In addition, in the embodiment as mentioned above, the separation balloon insertion device 108 including the high-frequency knife 16 is used. However, as shown in FIG. 110, a separation balloon insertion device 385 not including a high-frequency cutting instrument such as a high-frequency knife may be used with a popular high-frequency cutting instrument. Further, in the ninth embodiment, the endoscope 4 of which the insertion portion 3 is provided with the channels 2A and 2B is used. In the eleventh embodiment, this endoscope 4 may be used to smoothly perform the procedure using the grasping forceps 351.

Figure 121:
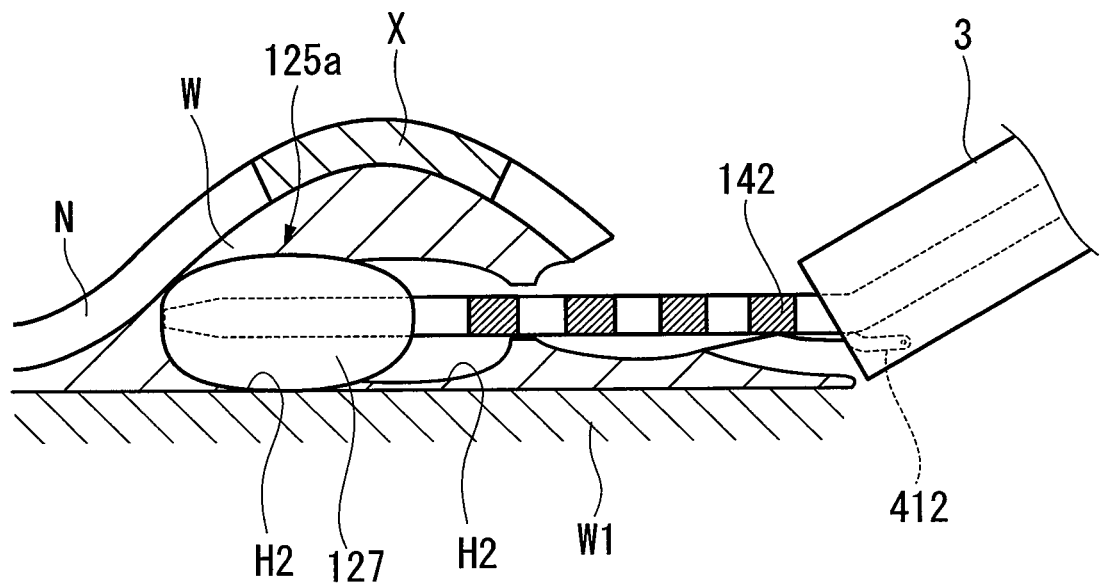

A twelfth embodiment of a mucosa separation apparatus and a method for mucosa separation of the present invention will be explained with reference to FIG. 111 and FIG. 121. Note that, the same descriptive symbols are used for component elements that are the same as those used in the first embodiment and a description thereof is omitted.

Figure 111:
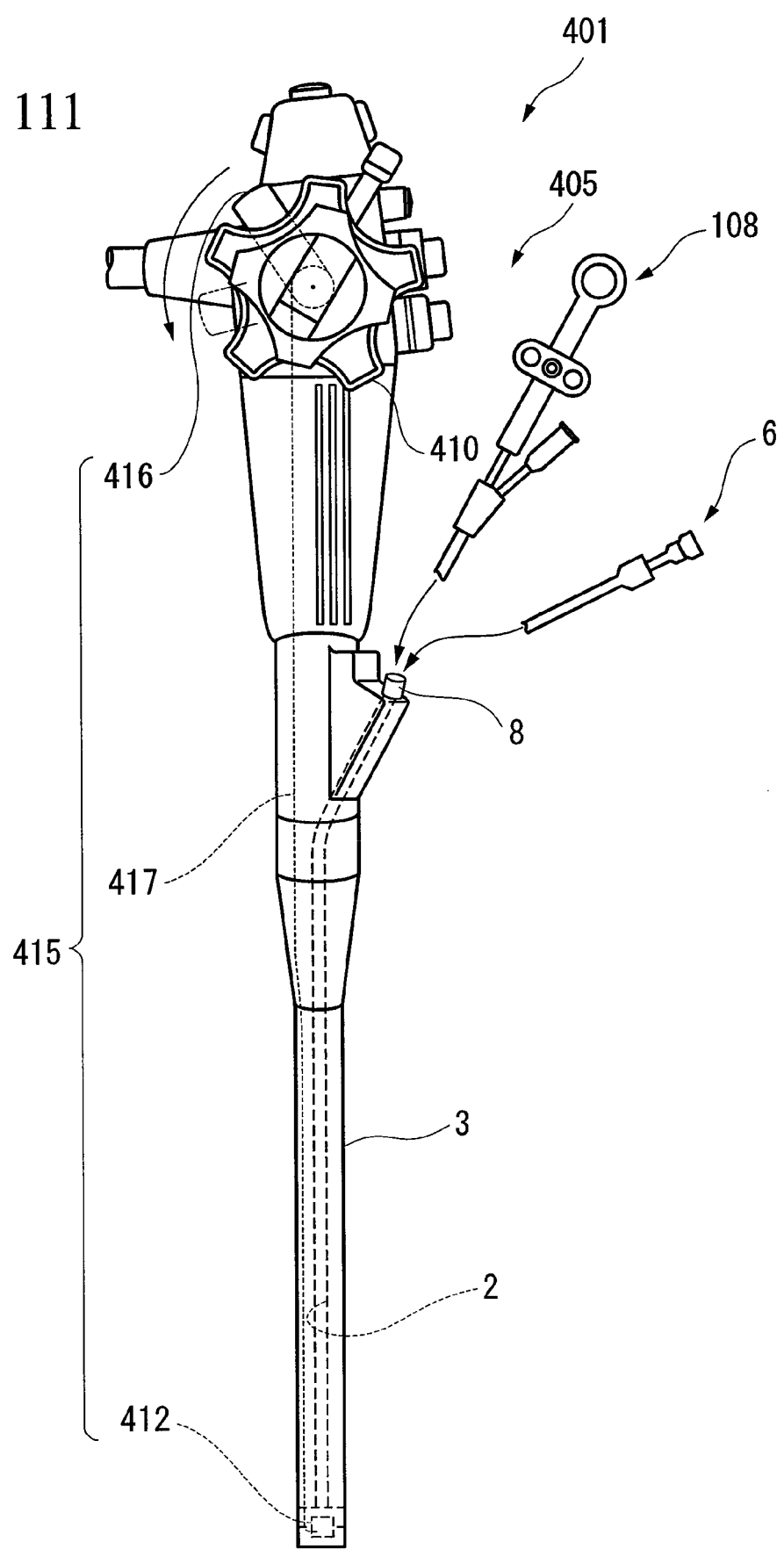
FIG. 111 is a view showing a mucosa separation apparatus of a twelfth embodiment of the present invention, and shows a schematic view of a mucosa separation system including the endoscope, the separation balloon insertion device, and the submucosal local injection needle.

As shown in FIG. 111, an endoscope system (mucosa separation apparatus) 401 of the present invention includes an endoscope 405, the separation balloon insertion device 108 and the submucosal local injection needle 6. The separation balloon insertion device 108 or the submucosal local injection needle 6 is inserted into the channel 2 formed in the insertion portion 3 of the endoscope 4 as appropriate.

Figure 112:
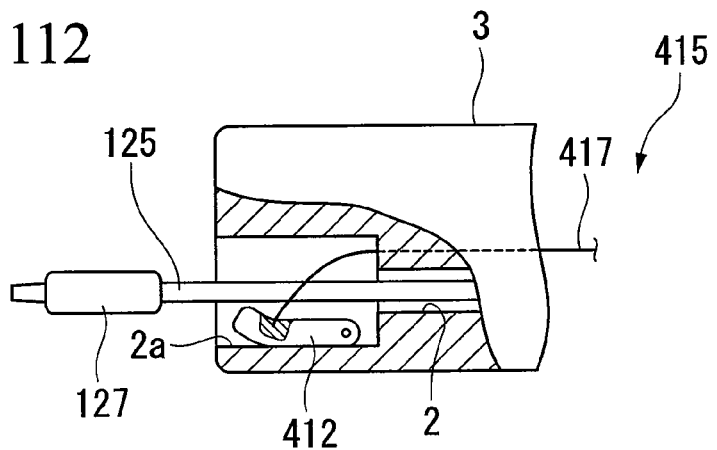
FIG. 112 is a partial sectional view showing the tip of the endoscope of the twelfth embodiment.
Figure 113:
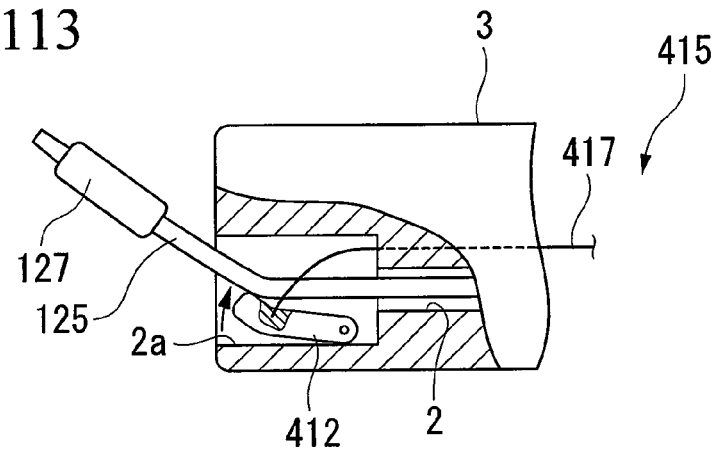
FIG. 113 is a partial sectional view showing the tip of the endoscope of the twelfth embodiment, and shows a state where the head portion of the balloon insertion portion is curved.

An aperture of the channel located at the tip of the insertion portion 3 faces forwards. That is, the endoscope 405 is a straight sight type endoscope. An operation section 410 for operating to curve the tip of the insertion portion 3 is disposed on the terminal portion of the endoscope 405. The endoscope 405 includes a forceps raising mechanism (curving portion) 415 for turning of the head portion 125a of the balloon insertion portion 125 of the separation balloon insertion device 108 which is protruded from an aperture 2a on the tip of the channel 2. As shown in FIG. 112 and FIG. 113, a forceps raising block 412 which is disposed at the aperture 2a is pushed onto the head portion 125a of the balloon insertion portion 125 which is inserted into the channel 2, and thereby the forceps raising mechanism 415 turns of the head portion 125a of the balloon insertion portion 125 which is protruded from the tip of the insertion portion 3.

The forceps raising mechanism 415 includes the forceps raising block 412 which is swingably moved, a forceps raising block operation section 416 for operating the forceps raising block 412 and an operation wire 417 which connects the forceps raising block 412 with the forceps raising block operation section 416. The forceps raising block 412 is disposed at the tip of the insertion portion 3 in the vicinity of the aperture 2a of the channel 2. When the forceps raising block operation section 416 is rotated in one rotation direction, a pulling force acts on the operation wire 417, and then the pulling force is transmitted to the forceps raising block 412 through the operation wire 417. Therefore, the forceps raising block 412 swings towards the center axis of the insertion portion 3. Otherwise, when the forceps raising block operation section 416 is rotated in the other rotation direction, a pushing force acts on the operation wire 417, and then the pushing force is transmitted to the forceps raising block 412 through the operation wire 417. Therefore, the forceps raising block 412 swings towards the outer side of the insertion portion 3 to retract.

Figure 114:
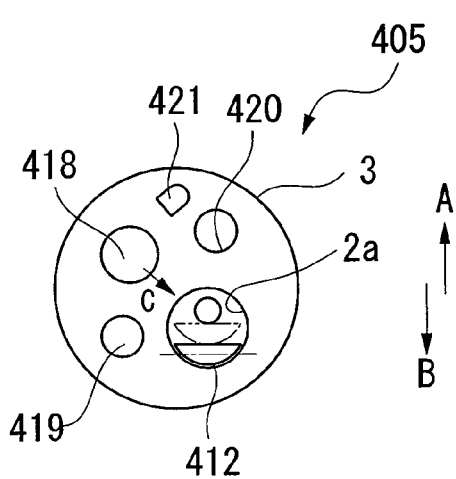
FIG. 114 is a plan view showing the top end surface of the insertion portion of the endoscope of the twelfth embodiment.

As shown in FIG. 114, the insertion portion 3 of the endoscope 405 is provided with an objective lens 418, a right side light guide 419, a left side light guide 420 and a cleaning fluid nozzle 421 which discharges a cleaning fluid to clean the objective lens 418. Note that, a direction A shown in FIG. 114 corresponds with the upward direction of the view field in the endoscope, and a direction B shown in FIG. 114 corresponds with the downward direction of the view field in the endoscope. Further, right and left directions in FIG. 114 come into the right and left directions of the view field in the endoscope.

The method for mucosa separation for removing a diseased part X developing inside an alimentary tract from a submucosal layer W using the mucosa separation system 401 as mentioned above will be explained.

The method for mucosa separation of this embodiment includes the steps of inflating, aperture-forming, inserting, angle-adjusting, length-adjusting, separating and incising. Each of the steps will be explained.

Figure 115:
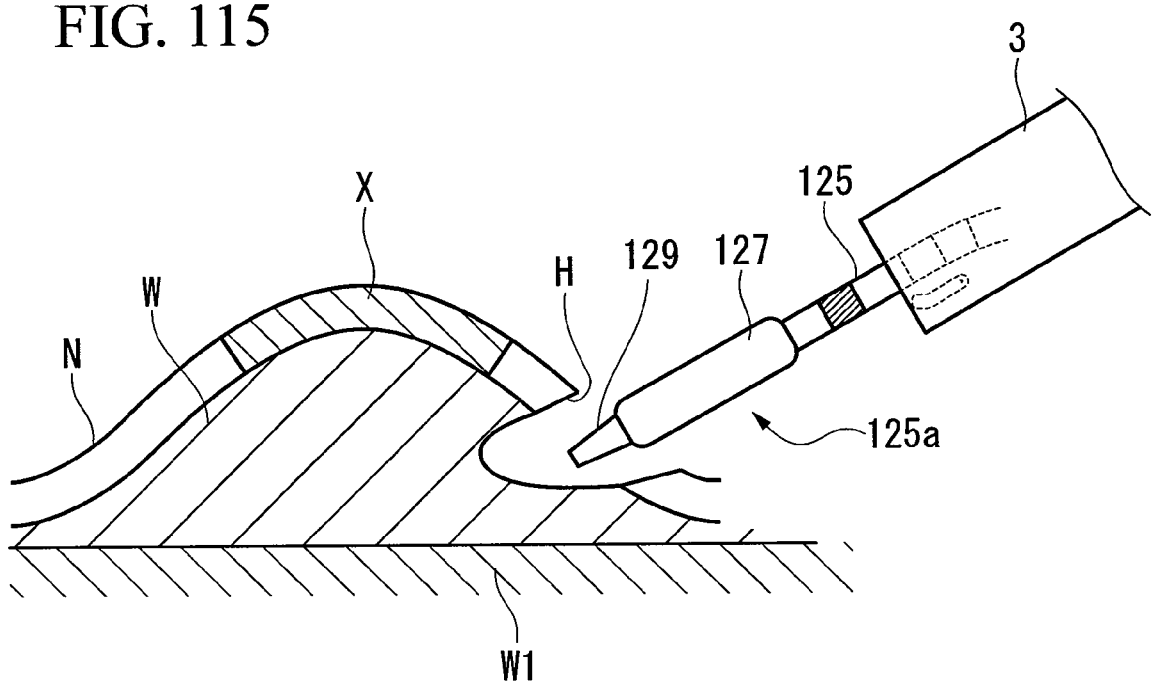
FIG. 115 is a view showing a method for mucosa separation of the twelfth embodiment of the present invention, and shows a state where the tip of the balloon insertion portion is inserted into the aperture after forming the aperture in the mucosa.
Figure 116:
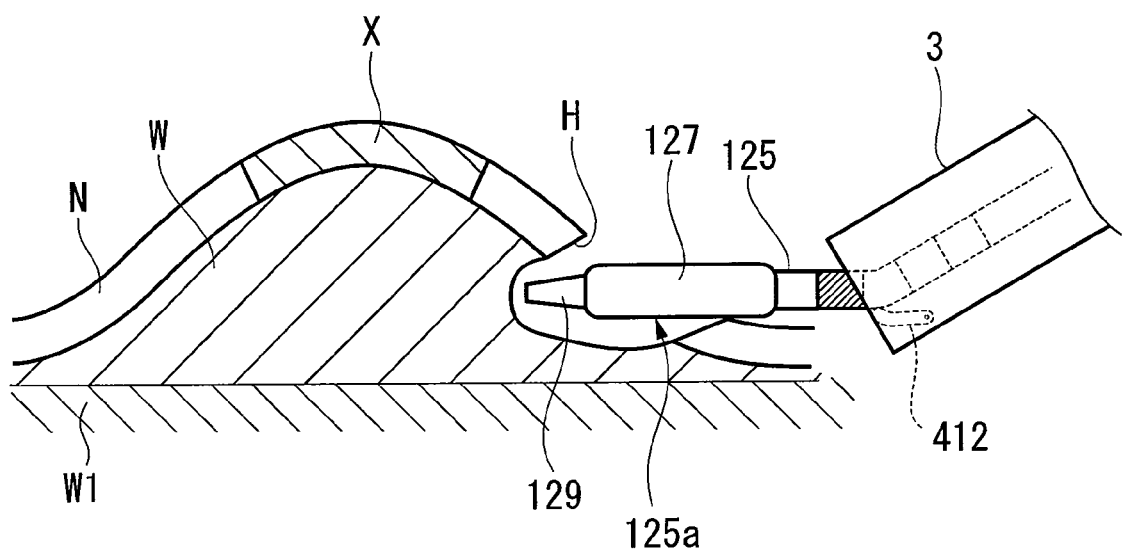
FIG. 116 is a view showing a method for mucosa separation of the twelfth embodiment of the present invention, and shows a state where the head portion of the balloon insertion portion is curved after inserting the head portion of the support device insertion portion into the aperture.

First, similar to the third embodiment, the steps of inflating and aperture-forming are performed. After that, the step of inserting is performed. That is, as shown in FIG. 115, the top end 129 of the balloon insertion portion 125 is inserted into the submocosa W through the aperture H.

After the step of inserting, the step of angle-adjusting is performed. In the step of inserting, the head portion 125a of the balloon insertion portion 125 is located so as to intersect with respect to the submocosa W (to be exact, the mucosa N before inflating) of the alimentary tract by a predetermined angle. However, in a case where the head portion 125a of the balloon insertion portion 125 is inserted into the inside of the submocosa W to separate the submocosa W from the muscularis propria W1, in order to prevent the top end 129 from approaching the muscularis propria W1, an insertion angle of the head portion 125a of the balloon insertion portion 125 with respect to the submocosa W must be varied so that the head portion 125a is substantially parallel to the muscularis propria W1 under the submucosal layer W.

The tip of the insertion portion 3 of the endoscope 405 is positioned in the vicinity of the diseased part X which is inflated, and the forceps raising block operation section 416 is operated to stand up the forceps raising block 412. Then, the tip of the forceps raising block 412 being stood up is pushed onto the head portion 125a of the balloon insertion portion 125, and thereby the direction of the head portion 125a of the balloon insertion portion 125 which is protruded from the channel 2 is adjusted so that the head portion 125a is substantially parallel to the muscularis propria W1. At this time, the direction of the head portion 125a which is protruded from the channel 2 is varied in the upward direction of the view field in the endoscope. Therefore, the head portion 125a of the balloon insertion portion 125 can be observed from obliquely above in the view field in the endoscope. As a result, the insertion angle of the head portion 125a of the balloon insertion portion 125 with respect to the submocosa W can be acknowledged accurately.

Incidentally, in a case where the direction of the head portion 125a of the balloon insertion portion 125 which is protruded from the channel 2 is adjusted to not the upward in a direction of the view field but a radial direction of the insertion portion 3, a curving portion of the head portion 125a of the balloon insertion portion 125 is observed in a curving direction of the head portion 125a in the view field of the endoscope. Therefore, the curving angle of the head portion 125a can hardly be acknowledged.

In this embodiment, the step of angle-adjusting is performed after the step of inserting. However, the angle-adjusting may be previously performed, and thereafter the step of inserting is performed. The step of inserting may be simultaneously performed with the step of angle-adjusting.

Figure 117:
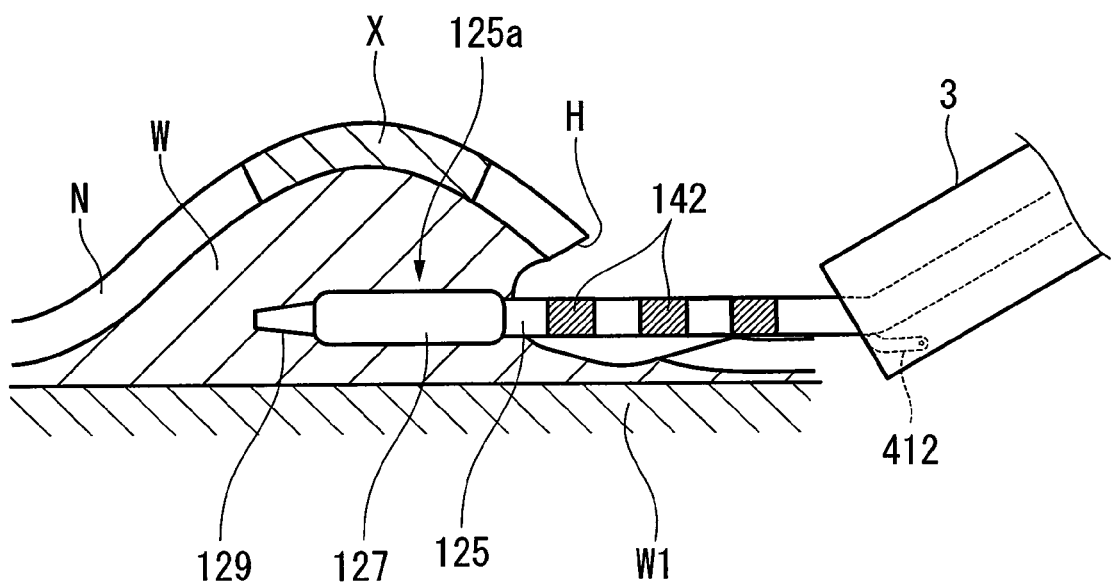
FIG. 117 is a view showing a method for mucosa separation of the twelfth embodiment of the present invention, and shows a state where the balloon insertion portion pierces the submucosal layer after curving the head portion of the balloon insertion portion.

After the step of angle-adjusting, the step of length-adjusting is performed. That is, as shown in FIG. 117, the balloon insertion portion 125 is moved along a direction being parallel to the surface of the alimentary tract, and thereby the head portion 125a of the balloon insertion portion 125 is pushed into the submucosal layer W through the aperture H, and is positioned at a predetermined position within the submucosal layer W according to the indicators 142 as guides.

Figure 118:
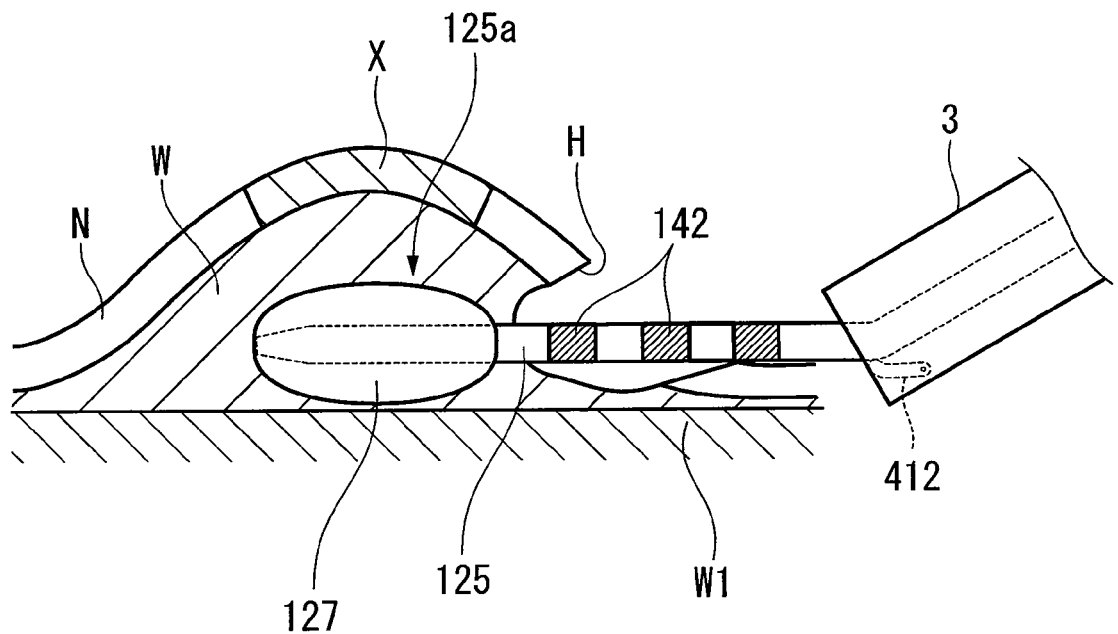
FIG. 118 is a view showing a method for mucosa separation of the twelfth embodiment of the present invention, and shows a state where the balloon is expanded within the submucosal layer after piercing the submucosal layer by the balloon insertion portion.

After the step of length-adjusting, the step of separating is performed. That is, a fluid is supplied into the passage 126 through the fill port 128 using a syringe (not shown). The fluid supplied into the passage 126 is supplied to the balloon 127 through the communication hole 130, and thereby the balloon 127 is inflated (shown in FIG. 118). Therefore, a part of the submucosal layer W is separated from the muscularis propria W1 existing under the submucosal layer W. Then, the fluid is discharged from the balloon 127 through the fill port 128, and thereby the balloon 127 deflates to its original shape. As a result, a cavity H1 is formed between the muscularis propria W1 and the submucosal layer W separated from the muscularis propria W1.

Figure 119:
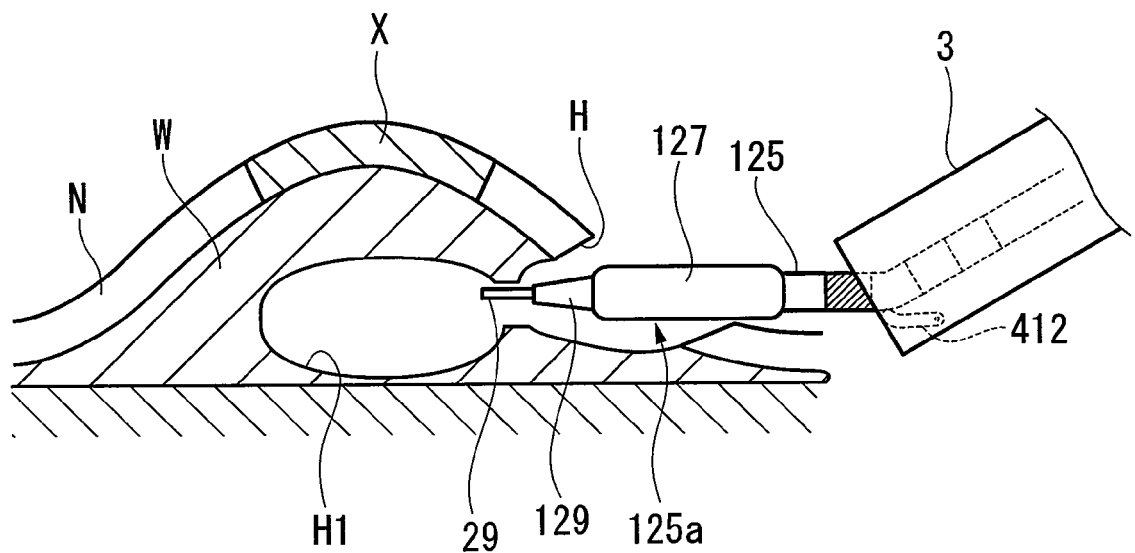
FIG. 119 is a view showing a method for mucosa separation of the twelfth embodiment of the present invention, and shows a state where the balloon insertion portion is retracted from the submucosal layer with the contracted balloon after expanding the balloon within the submucosal layer.

After the step of separating, the step of incising is performed. That is, the balloon insertion portion 125 is pulled back from the submucosal layer W until the outside of the aperture H. Then, similar to the step of aperture-forming, the knife portion 29 is protruded from the top end 129 of the balloon insertion portion 125, and is inserted into the aperture H (refer to FIG. 119). While the condition is held, high-frequency current is supplied to the knife portion 29, and the knife portion 29 is moved around the diseased part X. Therefore, the mucosa N around the aperture H is incised (refer to FIG. 49). After the mucosa N has been incised with a certain measure of width, supplying of high-frequency current is stopped, and the knife portion 29 is retracted into the operation tube 21.

Figure 120:
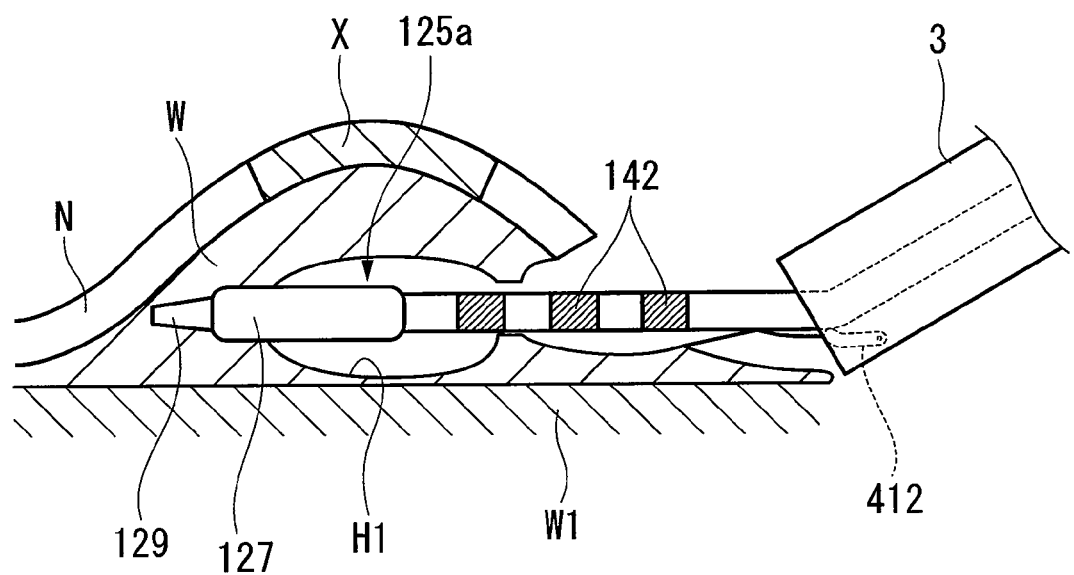

If it is impossible to separate the mucosa N including the diseased part X from the submucosal layer W by only the cavity H1 because the diseased part X is so large, the steps of length-adjusting, separating and incising are repeated. That is, as shown in FIG. 120, the balloon insertion portion 125 is re-inserted into the submucosal layer W located at the back of the cavity H1 through the aperture H according to the indicators 142 as guides. Then, the balloon 127 is inflated, and thereby the submucosal layer W which has not been separated from the muscularis propria W1 in the first step of separating is separated form the muscularis propria W1, and thereby a new cavity H2 is formed. After that, the step of incising is performed again (refer to FIG. 53).

As mentioned above, the steps of length-adjusting, separating and incising are repeated in accordance with the size of the diseased part X. Therefore, the submucosal layer W including the diseased part X is removed from the alimentary tract (refer to FIG. 25).

According to the mucosa separation apparatus and the method for mucosa separation of this embodiment, when the head portion 125a of the balloon insertion portion 125 is protruded from the aperture 2a of the channel 2, the forceps raising block 412 is pushed onto the head portion 125a of the balloon insertion portion 125, and thereby the direction of the head portion 125a can be varied upward in the direction of the view field in the endoscope. Therefore, in the case where the head portion 125a of the balloon insertion portion 125 is protruded from the tip of the insertion portion 3 along with the insertion portion 3 of the endoscope is located so as to intersect with respect to the submocosa W of the alimentary tract by a predetermined angle, the head portion 125a of the balloon insertion portion 125 is turned so as to be substantially parallel to the muscularis propria W1 under the submucosal layer W, and thereafter the head portion 125a can be inserted in the submucosal layer W. As a result, it is possible to prevent the head portion 125a of the balloon insertion portion 125 from inserting into the submucosal layer W more than a predetermined depth without a particular mechanism for the separation balloon insertion device 108.

The forceps raising mechanism 415 includes the forceps raising block 412, the forceps raising block operation section 416 and the operation wire 417. Therefore, the insertion angle of the head portion 125a of the balloon insertion portion 125 can be adjusted in accordance with the rotation operation of the forceps raising block operation section 416 even with the simple structure of the endoscope.

Since only one channel 2 is formed in the insertion portion 3 of the endoscope 405, it is possible to downsize the external diameter of the insertion portion 3. Therefore, the insertion portion 3 can be easily inserted into the body cavity. In addition, since a wide gap between the insertion portion 3 and the mucosa N within the alimentary tract can be achieved, it is possible to improve the operability of the endoscope 405 such as the angle operation and the rotational operation thereof.

When bleeding occurs while the mucosa N is separated, or when bleeding occurs with incising of the knife portion 29, the head portion 125a of the balloon insertion portion 125 is close to the bleeding part, and then the balloon 127 is inflated to press the bleeding part. Therefore, the arrest of bleeding can be performed. Further, the knife portion 29 is put onto the bleeding part, and high-frequency current is conducted. Therefore, the arrest of bleeding can be performed by blood clotting.

Next, a thirteenth embodiment of a mucosa separation apparatus and a method for mucosa separation of the present invention will be explained with reference to FIG. 122 through FIG. 129. Note that, the same descriptive symbols are used for component elements that are the same as those used in the first embodiment and a description thereof is omitted.

Figure 122:
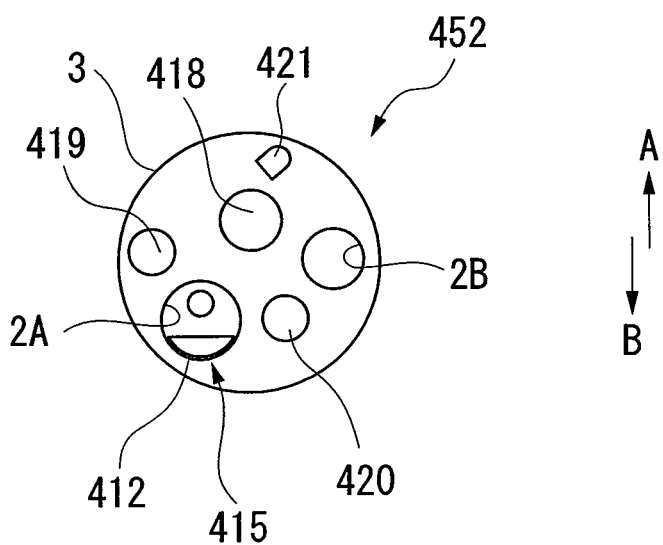

The thirteenth embodiment is different from the twelfth embodiment in the below respects. That is, as shown in FIG. 122, two channels 2A and 2B are formed in the insertion portion 3 of an endoscope 452. The forceps raising mechanism 415 is disposed at the aperture of the channel 2A.

The channel 2A is offset from the channel 2B in the curving direction of the head portion 125a of the balloon insertion portion 125 which curves by pushing the head portion 125a onto the forceps raising block 412. That is, as shown in FIG. 122, the channels 2A and 2B are formed so that the channel 2A separates from the channel 2B in the upward direction (direction A) or the downward direction (direction B) of the view field in the endoscope, and separates from the channel 2B across the objective lens 418. The balloon insertion portion 125 is inserted into the channel 2A, and a grasping forceps 453 is inserted into the channel 2B.

The method for mucosa separation for removing a diseased part X developing inside an alimentary tract from a submucosal layer W using the endoscope 452 as mentioned above will be explained.

The method for mucosa separation of this embodiment includes the steps of inflating, aperture-forming, angle-adjusting, inserting, length-adjusting, separating and incising. Each of the steps will be explained.

Figure 123:
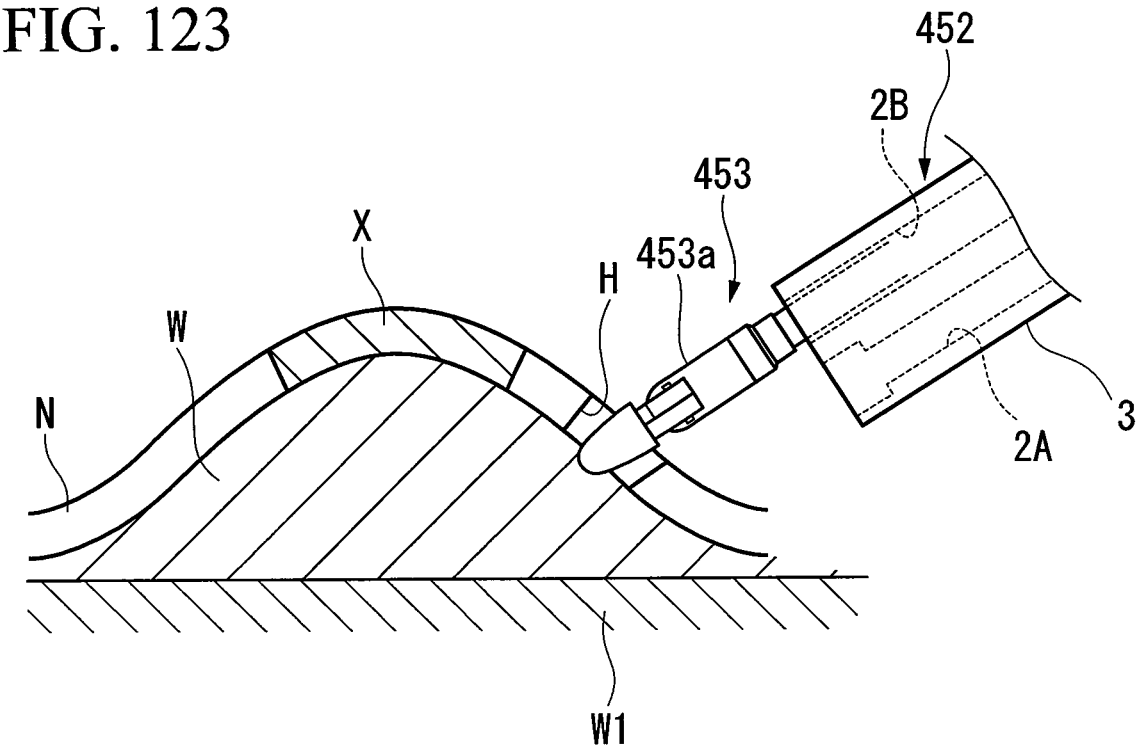
Figure 124:
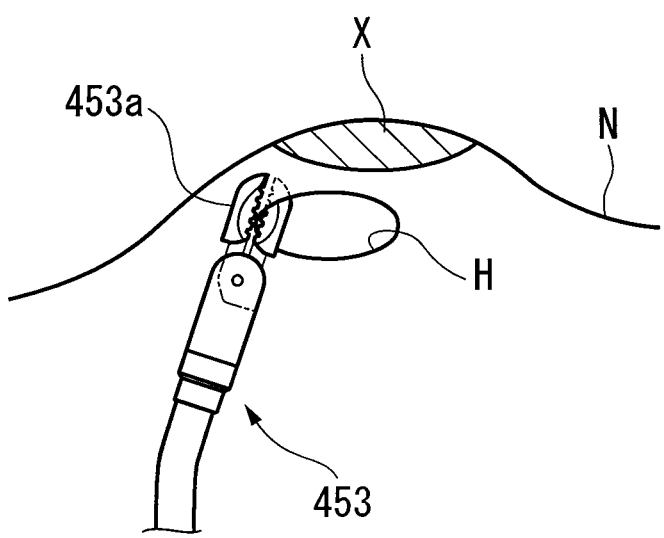

First, similar to the third embodiment, the steps of inflating and aperture-forming are performed. After that, as shown in FIG. 123 and FIG. 124, the grasping forceps 453 is inserted into the channel 2B which is positioned at the upside of the view field of the endoscope, and then an instrument 453a which is provided at the tip of the grasping forceps 453 is protruded from the aperture of the channel 2B. The mucosa N and the submucosal layer W in the vicinity of the diseased part X are grasped by the instrument 453a. While the condition is held, the step of angle-adjusting is performed. That is, the forceps raising block operation section 416 is operated to previously raise the forceps raising block 412. Then, the head portion 125a of the balloon insertion portion 125 is pushed onto the tip of the forceps raising block 412 which is previously raised, and then the angle of the head portion 125a which is protruded from the channel 2 is adjusted so that the head portion 125a of the balloon insertion portion 125 becomes to be substantially parallel to the muscularis propria W1.

Figure 125:
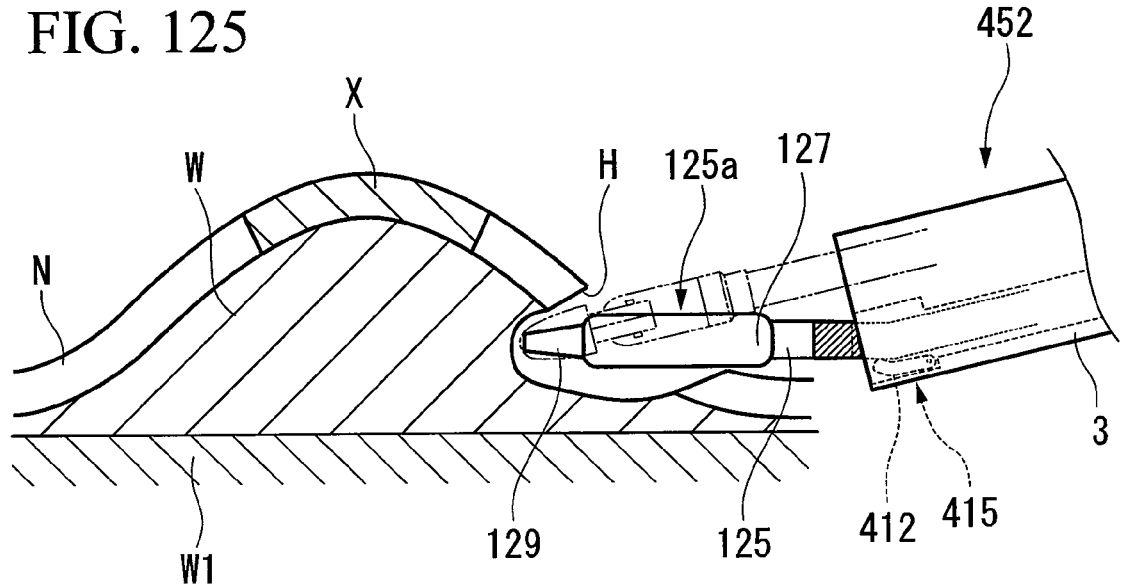

After the step of angle-adjusting, the step of inserting is performed. That is, as shown in FIG. 125, while the mucosa N and the submucosal layer W in the vicinity of the diseased part X are grasped by the grasping forceps 453, the top end 129 of the balloon insertion portion 125 is inserted into the submucosal layer W through the aperture H.

Figure 126:
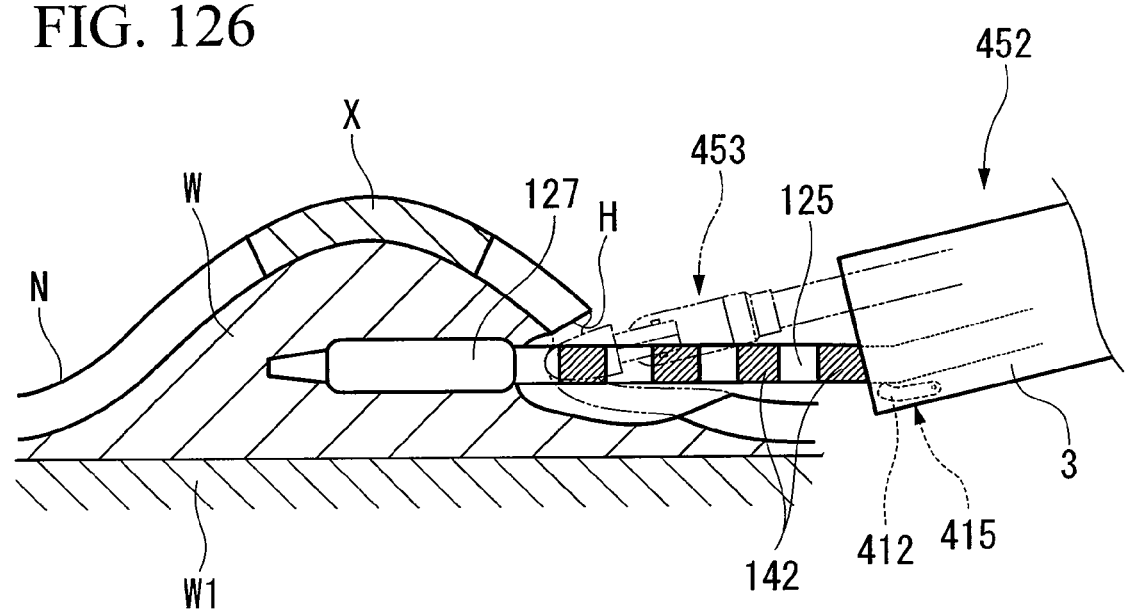

After the step of inserting, the step of length-adjusting is performed. That is, as shown in FIG. 126, the balloon insertion portion 125 is moved along a direction being parallel to the surface of the alimentary tract, and thereby the head portion 125a of the balloon insertion portion 125 is pushed into the submucosal layer W through the aperture H, and is positioned at a predetermined position within the submucosal layer W according to the indicators 142 as guides.

Note that, in the case where the balloon insertion portion 125 which is inserted into the channel 2A can be confirmed in the view field in the endoscope by grasping the mucosa N and the submucosal layer W in the vicinity of the diseased part X by the grasping forceps 453, the step of inserting may be simultaneously performed with the step of length-adjusting.

After the step of length-adjusting, the step of separating is performed. That is, the balloon 127 is inflated, and thereby a part of the submucosal layer W is separated from the muscularis propria W1 under the submucosal layer W. After that, the balloon 127 is deflated so as to put the shape of the balloon 127 back on, and thereby a cavity H1 is formed between the muscularis propria W1 and the submucosal layer W separated from the muscularis propria W1.

Figure 127:
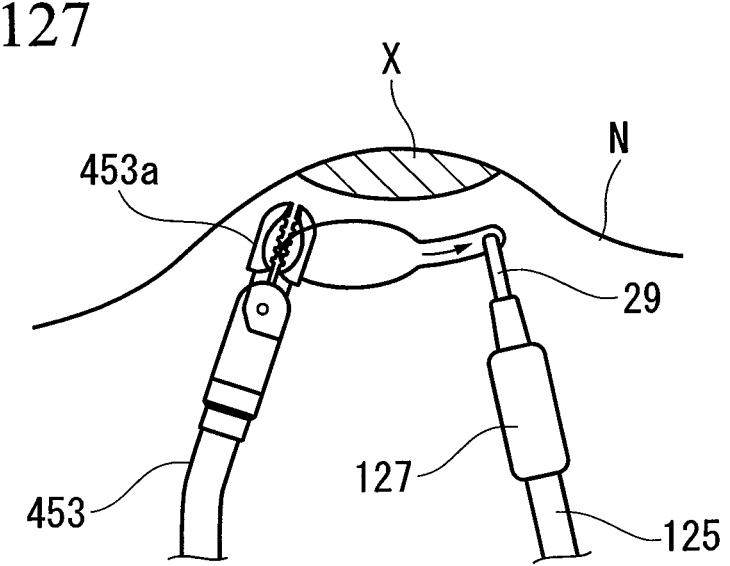

After the step of separating, the step of incising is performed. That is, while the mucosa N and the submucosal layer W in the vicinity of the diseased part X are grasped by the grasping forceps 453, the balloon insertion portion 125 is pulled back from the submucosal layer W until the outside of the aperture H. Then, as shown in FIG. 127, the knife portion 29 is protruded from the top end 129 of the balloon insertion portion 125, and is inserted into the aperture H. While the condition is held, high-frequency current is supplied to the knife portion 29, and the knife portion 29 is moved around the diseased part X. Therefore, the mucosa N around the aperture H is incised. After the mucosa N has been incised with a certain measure of width, supplying of high-frequency current is stopped, and the knife portion 29 is retracted into the operation tube 21.

Note that, the steps of angle-adjusting, inserting, length-adjusting, separating and incising may be performed while the mucosa N and the submucosal layer W in the vicinity of the diseased part X are grasped by the grasping forceps 453. Of course, the mucosa N and the submucosal layer W in the vicinity of the diseased part X may be released whenever each of the steps finishes, and then next step may be performed. However, when the head portion 125a of the balloon insertion portion 125 is inserted into the submucosal layer W or the knife 129 is moved around the diseased part X, the mucosa N and the submucosal layer W in the vicinity of the diseased part X are pushed by the head portion 125a of the balloon insertion portion 125 or the knife 129, and thereby escape of the mucosa N or the submucosal layer W may be caused. Therefore, when each of the steps of inserting and incising is performed, it is preferable to previously grasp the mucosa N and the submucosal layer W in the vicinity of the diseased part X. As a result, it is possible to prevent the escape of the mucosa N or the submucosal layer W being caused.

If it is impossible to separate the mucosa N including the diseased part X from the submucosal layer W by only the cavity H1 because the diseased part X is so large, the steps of length-adjusting, separating and incising are repeated. As mentioned above, the steps of sticking, length-adjusting, separating and incising are repeated in accordance with the size of the diseased part X. Therefore, the submucosal layer W including the diseased part X is removed from the alimentary tract.

According to the mucosa separation apparatus and the method for mucosa separation of this embodiment, the balloon insertion portion 125 is inserted into the channel 2A, and the grasping forceps 351 is inserted into the channel 2B. Then, the separation balloon insertion device 108 is used while the mucosa N and the submucosal layer W are grasped by the grasping forceps 351. Thereby, the time for the operations can be shortened. Further, the mucosa N can be reliably incised. Furthermore, since the number of times of replacing instruments decreases, the burden of a patient can be reduced.

Figure 128:
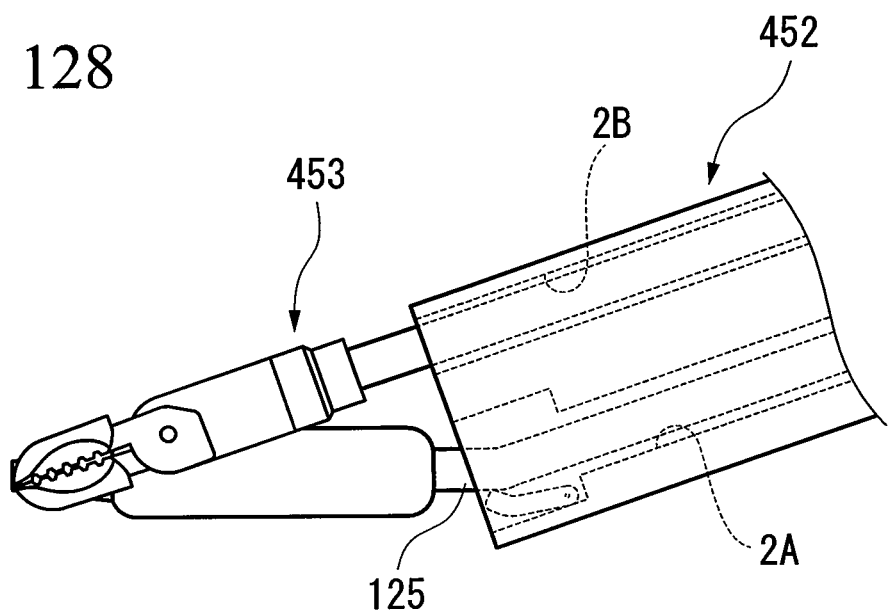

Note that, in this embodiment, as shown in FIG. 128, the position in the direction A or in the direction B (shown in FIG. 122) of the channel 2A is different from the position in the direction A or in the direction B of the channel 2B. Since the position of the channel 2A is different from the position of the channel 2B, when the head portion 125a of the balloon insertion portion 125 which is protruded from the channel 2A is curved, the position in the direction A or in the direction B (shown in FIG. 122) of the head portion 125a of the balloon insertion portion 125 corresponds with the position in the direction A or in the direction B of the tip of the grasping forceps 453 which is protruded from the channel 2B. Therefore, each of the processes as described above can be smoothly performed using the grasping forceps 453.

Figure 129:
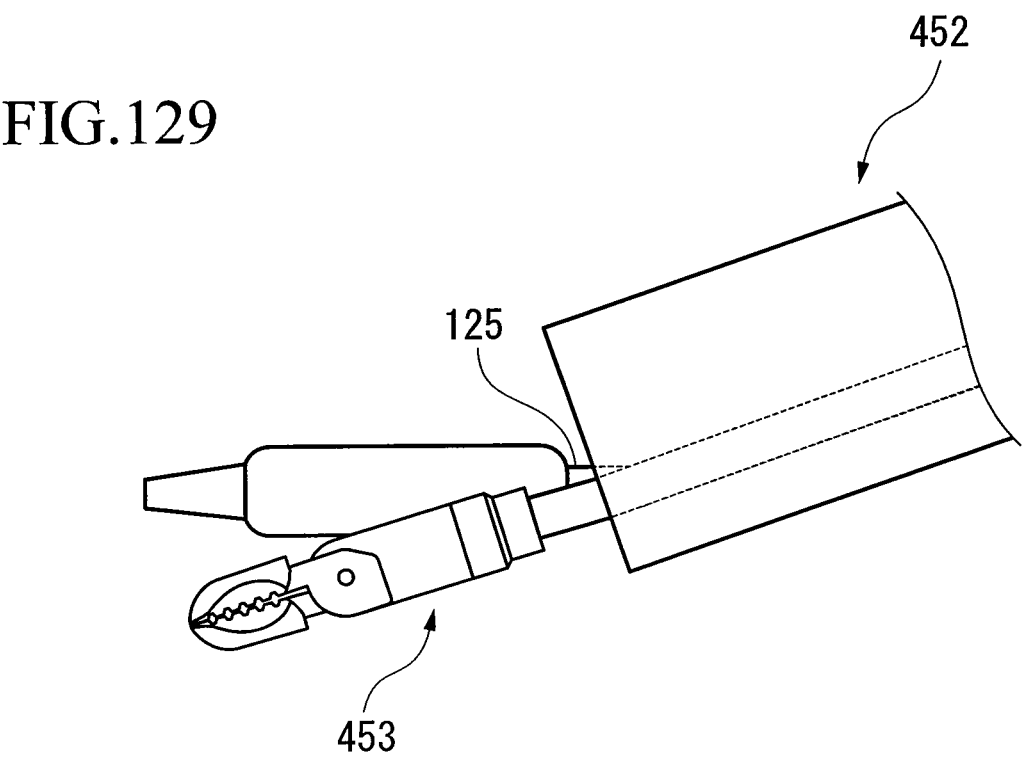

Incidentally, in the case where the position in the direction A or in the direction B (shown in FIG. 122) of the channel 2A corresponds with the position in the direction A or in the direction B of the channel 2B, as shown in FIG. 129, the position in the direction A or in the direction B (shown in FIG. 122) of the head portion 125a of the balloon insertion portion 125 is different from the position in the direction A or in the direction B of the tip of the grasping forceps 453 which is protruded from the channel 2B. Therewith, it is difficult to perform each of the processes as described above while the mucosa N and the submucosal layer W are grasped using the grasping forceps 453.

Further, the channels 2A and 2B are formed so that the channel 2A separates from the channel 2B in a direction being different from the curving direction of the head portion 125a of the balloon insertion portion 125. Therefore, if the head portion 125a of the balloon insertion portion 125 inserted into the channel 2A is curved, the head portion 125a does not interfere with the instrument inserted into the channel 2B. In contrast, when the channels 2A and 2B are formed so that the channel 2A separates from the channel 2B in the curving direction of the head portion 125a of the balloon insertion portion 125, if the head portion 125a of the balloon insertion portion 125 inserted into the channel 2A is curved, the head portion 125a may interfere with the instrument inserted into the channel 2B.

Figure 130:
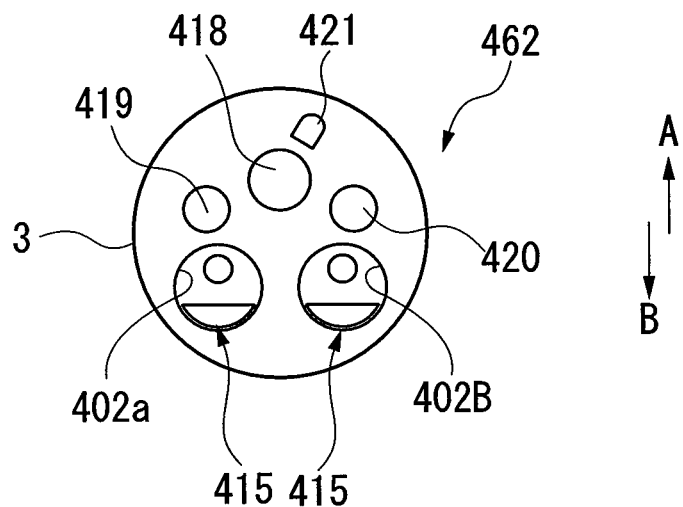
Figure 131:
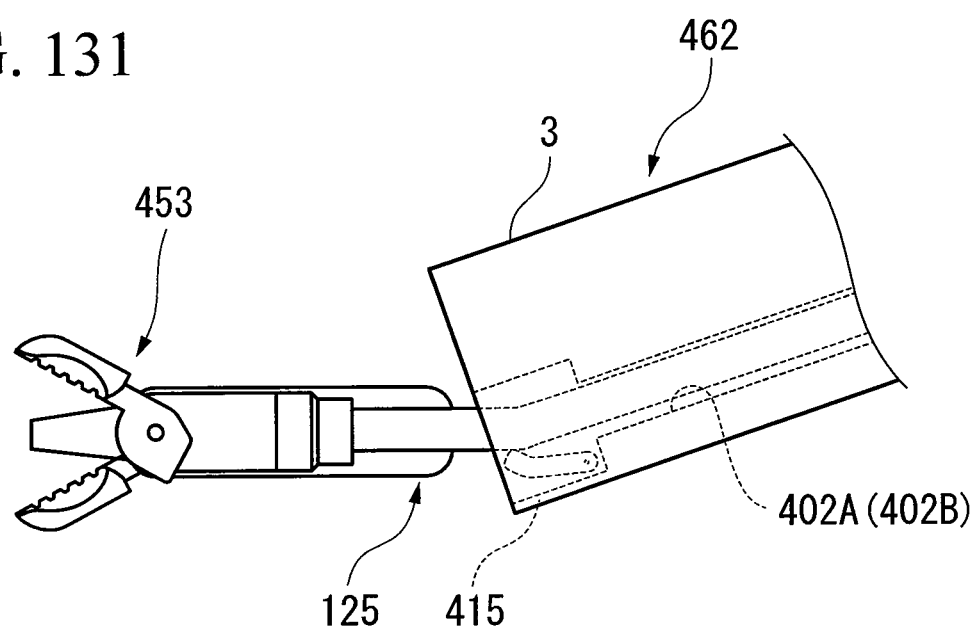

Next, a fourteenth embodiment of a mucosa separation apparatus and a method for mucosa separation of the present invention will be explained with reference to FIG. 130 and FIG. 131. Note that, the same descriptive symbols are used for component elements that are the same as those used in the first embodiment and a description thereof is omitted.

The fourteenth embodiment is different from the thirteen embodiment in the below respects. That is, as shown in FIG. 130, two channels 402A and 402B are formed so as to be positioned at the sides of the objective lens 418 at downside of the view field in the endoscope 462. Further, the channels 402A and 402B are formed so that the height of the channel 402A is equal to that of the channel 402B in a direction A or a direction B in FIG. 130. Each of the channels 402A and 402B is provided with the forceps raising mechanism 415.

The method for mucosa separation which is performed using the endoscope 462 as mentioned above is the same as the thirteenth embodiment. Therefore, a description thereof is omitted.

According to the mucosa separation apparatus and the method for mucosa separation of this embodiment, the height in the direction A or in the direction B (shown in FIG. 130) of the instrument which is inserted into the channel 402A can be equal to the height in the direction A or in the direction B (shown in FIG. 130) of the instrument which is inserted into the channel 402B. Further, the height in the direction A or in the direction B of the instrument inserted into the channel 402A can be different from the height in the direction A or in the direction B of the instrument inserted into the channel 402B. Therefore, the instrument inserted into the channel 402A and the instrument inserted into the channel 402B can be widely utilized. In addition, it is possible to prevent the instrument inserted into the channel 402A from interfering with the instrument inserted into the channel 402B.

Note that, in the twelfth embodiment, the separation balloon insertion device 108 having the high-frequency knife 16 is used. However, the heretofore known separation balloon insertion device 385 which does not have a high-frequency cutting instrument such as a high-frequency knife can be used with heretofore known high-frequency cutting instruments.

The insertion portion may be provided with three or more channels. The point is only that at least one of the channels is provided with the forceps raising mechanism. The forceps raising mechanism is not limited to include the forceps raising block, the forceps raising block operation section and the operation wire. For example, the forceps raising block may be driven by an actuator such as motor.

It should be understood that the scope of the present invention is not limited to the embodiments as described above. Various modifications can be made without departing from the scope of the present invention.

For example, operations which are performed using the mucosa separation system as described above are not limited to the operations as described above. Only a certain process may be performed.

What is claimed is:

1. A mucosa separation apparatus configured for performing mucosa separation, comprising:
    a first insertion portion inserted into an interior of a subject comprising a first channel, a second channel, and a third channel;
    an expansion portion disposed on a head portion of the first insertion portion, and which expands by infusion of a fluid;
    the first channel being configured to supply the fluid to the expansion portion;
    a high-frequency incision tool inserted within the second channel such that the high-frequency incision tool is capable of advancing to and retracting from a position at a head side beyond the expansion portion;
    an operation wire inserted within the first channel, the operation wire configured to curve the head portion of the first insertion portion that includes the expansion portion and the high-frequency incision tool with respect to a part of the first insertion portion which is closer to a base portion of the first insertion portion than the head portion thereof; and
    a first curving support member comprising a plate member inserted within the third channel, the first curving support member configured to curve the head portion of the first insertion portion in a particular direction, wherein
    the expansion portion is configured to be expanded in a state that the first curving support member is inserted into an incision portion such that a longitudinal axis of the first curving support member has a predetermined angle to a face of the incision portion,
    a plurality of holes are formed in the first channel to communicate from the first channel to an inside of the expansion portion so as to supply a medium for expansion to the expansion portion,
    the plurality of holes is provided in line on a plane including the particular direction in which the first insertion portion curves, the plurality of holes being positioned and configured so as to form a flexible portion, which is more flexible than the base portion of the first insertion portion in the particular direction,
    the flexible portion is positioned within a range where the expansion portion of the first insertion portion is provided,
    an external diameter of the high-frequency incision tool is smaller than an external diameter of the expansion portion in a deflated state,
    the first curving support member is eccentrically inserted into an inside of the first insertion portion relative to an external diameter direction,
    the high-frequency incision tool is inserted into the second channel at an opposite radial side of the first curving support member, and
    the plurality of the holes which form the flexible portion is provided on an opposite radial side to which the first curving support member is eccentric.

2. The mucosa separation apparatus according to claim 1, wherein
    a head end of the operation wire is connected to the head portion of the first insertion portion within the first channel and a base end of the operation wire is connected with an operation section disposed on a base portion of the first insertion portion; and further wherein
    the head portion of the first insertion portion is curved by moving the operation section.

3. The mucosa separation apparatus according to claim 2, wherein
    the first curving support member is arranged so as to bring said one direction into line with the direction in which the head portion of the first insertion portion is allowed to curve.

* * * * *